(12) United States Patent
Thomson et al.

(10) Patent No.: US 11,286,226 B2
(45) Date of Patent: Mar. 29, 2022

(54) POLYCYCLIC CARBOGENIC MOLECULES AND USES THEREOF AS ANTI-CANCER AGENTS

(71) Applicant: Northwestern University, Evanston, IL (US)

(72) Inventors: Regan James Thomson, Chicago, IL (US); Emily E. Robinson, Chicago, IL (US)

(73) Assignee: Northwestern University, Evanston, IL (US)

( * ) Notice: Subject to any disclaimer, the term of this patent is extended or adjusted under 35 U.S.C. 154(b) by 187 days.

(21) Appl. No.: 16/137,994

(22) Filed: Sep. 21, 2018

(65) Prior Publication Data

US 2019/0127306 A1     May 2, 2019

Related U.S. Application Data

(60) Provisional application No. 62/561,464, filed on Sep. 21, 2017.

(51) Int. Cl.

| | | |
|---|---|---|
| C07C 49/617 | (2006.01) |
| C07C 49/788 | (2006.01) |
| C07C 45/67 | (2006.01) |
| C07C 49/792 | (2006.01) |
| C07D 303/32 | (2006.01) |
| C07D 313/10 | (2006.01) |
| C07C 49/453 | (2006.01) |
| C07C 49/757 | (2006.01) |
| C07C 49/643 | (2006.01) |

(52) U.S. Cl.
CPC .......... *C07C 49/788* (2013.01); *C07C 45/673* (2013.01); *C07C 49/453* (2013.01); *C07C 49/643* (2013.01); *C07C 49/757* (2013.01); *C07C 49/792* (2013.01); *C07D 303/32* (2013.01); *C07D 313/10* (2013.01); *C07B 2200/07* (2013.01); *C07C 2603/26* (2017.05); *C07C 2603/32* (2017.05); *C07C 2603/36* (2017.05); *C07C 2603/50* (2017.05); *C07C 2603/94* (2017.05)

(58) Field of Classification Search
CPC .................................................. C07C 49/617
See application file for complete search history.

(56) References Cited

PUBLICATIONS

American Chemical Society. Chemical Abstract Service. RN #: 2171455-64-2. First public availability date/entry into STN on Jan. 30, 2018. (Year: 2018).*
Robinson, E., et al. "A Strategy for the Convergent and Stereoselective Assembly of Polycyclic Molecules." J. Am. Chem. Soc. (2018), vol. 140, pp. 1956-1965. (Year: 2018).*
Robinson, et al., "A Strategy for the Convergent and Stereoselective Assembly of Polycyclic Molecules", Journal of the American Chemical Society, 2018, 140, 1956-1965, 10 pages.

* cited by examiner

*Primary Examiner* — John S Kenyon
(74) *Attorney, Agent, or Firm* — Quarles & Brady LLP

(57) ABSTRACT

Disclosed are new polycyclic carbogenic molecules and their methods of synthesis. The new polycyclic carbogenic molecules may be utilized in anti-cancer therapies. In particular, the polycyclic carbogenic molecules may be formulated as pharmaceutical compositions that comprise the small molecules, which compositions may be administered in methods of treating and/or preventing cell proliferative diseases and disorders such as cancer. The new polycyclic carbogenic molecules may be prepared from vinyl- or allyl-substituted cyclohexenone precursors via preparation of a silyl bis-enol ether intermediate.

15 Claims, 7 Drawing Sheets

| | PC3 cell line (prostate) | | | MDA-MB-231 cell line (breast) | | |
|---|---|---|---|---|---|---|
| | conc. (uM) | | | conc. (uM) | | |
| | 40 | 5 | 0.625 | 40 | 5 | 0.625 |
| | 0.51 | 0.93 | 0.92 | 0.18 | 0.82 | 0.92 |

Compound 18

| | PC3 cell line (prostate) | | | MDA-MB-231 cell line (breast) | | |
|---|---|---|---|---|---|---|
| | conc. (uM) | | | conc. (uM) | | |
| | 40 | 5 | 0.625 | 40 | 5 | 0.625 |
| | 0.19 | 0.85 | 0.9 | 0.06 | 0.6 | 0.93 |

Compound 24

POLYCYCLIC CARBOGENIC MOLECULES AND USES THEREOF AS ANTI-CANCER AGENTS

CROSS-REFERENCE TO RELATED PATENT APPLICATIONS

The present application claims the benefit of priority under 35 U.S.C. § 119(e) to U.S. Provisional Application No. 62/561,464, filed on Sep. 21, 2017, the content of which is incorporated herein by reference in its entirety.

BACKGROUND

The field of the invention relates to new small molecules and uses of the new small molecules as anti-cancer agents. The new small molecules are polycyclic carbogenic molecules that are potent to a variety of cancer cells.

While treatment options have improved in recent years, cancer remains the second leading cause of death in the United States. Many cancers lack effective treatments and have poor long-term prognoses. In particular, multiple myeloma is the second most prevalent hematological malignancy and kills over 10,000 people annually. The median survival from this type of cancer is approximately 5-7 years. Even with the advent of several new chemotherapies, only 25-35% of patients respond to these drugs. Additional treatment options are necessary for patients who fail to respond to current therapies and for those who develop resistance to current therapies.

Here, as part of an effort to discover and evaluate new small molecules that have the potential for treating human cancer, we have identified a series of polycyclic carbogenic molecules that display potent in vitro cytotoxicity against cancer cells. These compounds are complex sp3-rich polycyclic compound having unique substitution patterns that impart on them activity against a variety of human cancer cell lines. Compound analogs have been synthesized and tested to generate robust structure-activity relationships based on multiple sites of diversification. These new compounds therefore hold promise as new potential treatments for cancer and other proliferative diseases.

SUMMARY

Disclosed are new polycyclic carbogenic molecules and their methods of synthesis. The new polycyclic carbogenic molecules may be utilized in anti-cancer therapies. In particular, the polycyclic carbogenic molecules may be formulated as pharmaceutical compositions that comprise the small molecules, which compositions may be administered in methods of treating and/or preventing cell proliferative diseases and disorders such as cancer.

In some embodiments, the disclosed polycyclic molecules are tricyclic molecules having Formula I, or salts, solvates, epoxides, or spirocyclic derivatives thereof:

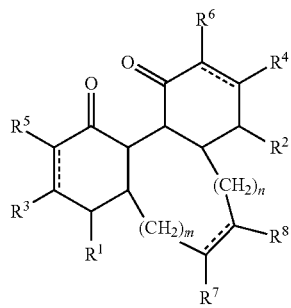

I wherein:

m and n are selected from 0 or 1; and each occurrence of $R^1$, $R^2$, $R^3$, $R^4$, $R^5$, $R^6$, $R^7$, and $R^8$ is independently selected from hydrogen, alkyl, dialkyl (e.g., dimethyl), hydroxyl (including a protected hydroxyl), hydroxyl-alkyl (including a protected alcohol), alkoxy, alkyl-alkoxy (including a masked aldehyde), alkyl-dialkoxy (e.g., methyl-dimethoxy), and acetyl;

or $R^3$ and $R^5$ together form an epoxide;

or $R^4$ and $R^6$ together from an epoxide;

or $R^7$ and $R^8$ together from an epoxide.

In some embodiments, an epoxide of Formula I may have a Formula II or III:

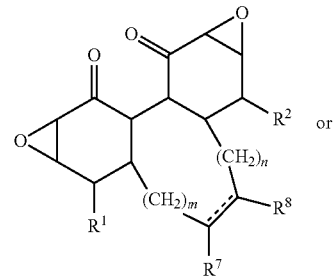

II or

III

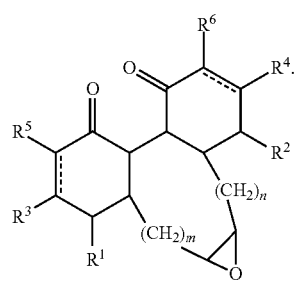

The disclosed polycylic molecules may include spirocyclic derivatives of the compounds of Formula I having a Formula IV or epoxides thereof having Formula V or VI:

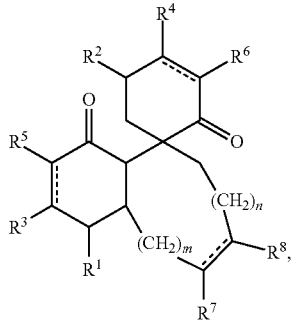

IV

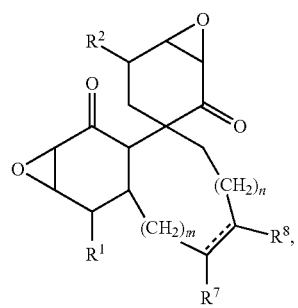

V

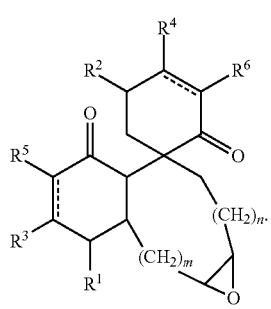

VI

In some embodiments, the disclosed polycyclic molecules are bicyclic molecules having Formula VII, or salts, solvates, epoxides, or spirocyclic derivatives thereof:

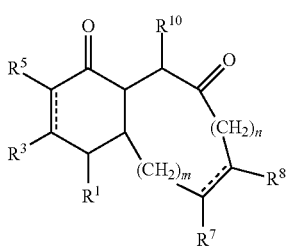

VII wherein:
m and n are selected from 0 or 1; and
each occurrence of $R^1$, $R^3$, $R^5$, $R^7$, $R^8$, and $R^{10}$ is independently selected from hydrogen, alkyl, dialkyl (e.g., dimethyl), hydroxyl (including a protected alcohol), alkoxy, alkyl-alkoxy (including a masked aldehyde), alkyl-dialkoxy (e.g., methyl-dimethoxy), and acetyl;
or $R^3$ and $R^5$ together form an epoxide;
or $R^7$ and $R^8$ together from an epoxide.

The disclosed polycyclic molecules may include tricyclic molecules having Formula VIII, or salts, solvates, epoxides, or spirocyclic derivatives thereof:

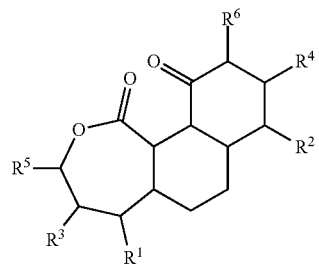

VIII wherein:
m and n are selected from 0 or 1; and
each occurrence of $R^1$, $R^2$, $R^3$, $R^4$, $R^5$, and $R^6$ is independently selected from hydrogen, alkyl, and dialkyl.

The disclosed polycyclic molecules may include tricyclic molecules having Formula IX, or salts, solvates, epoxides, or spirocyclic derivatives thereof:

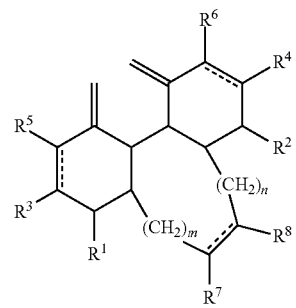

IX wherein:
m and n are selected from 0 or 1; and
each occurrence of $R^1$, $R^2$, $R^3$, $R^4$, $R^5$, $R^6$, $R^7$, and $R^8$ is independently selected from hydrogen, alkyl, and dialkyl;
or $R^5$ from a keto group with the ring carbon to which it is attached;
or $R^6$ forms a keto group with the ring carbon to which it is attached.

In some embodiments, where the polycyclic molecules are tricyclic molecules having Formula VII and where $R^5$ from a keto group with the ring carbon to which it is attached and/or $R^6$ forms a keto group with the ring carbon to which it is attached, the polycyclic molecule may have a Formula X:

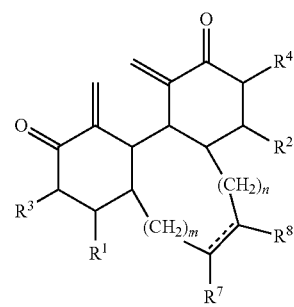

X

The disclosed polycyclic molecules may include tetracyclic molecules having Formula XI, or salts, solvates, epoxides, or spirocyclic derivatives thereof:

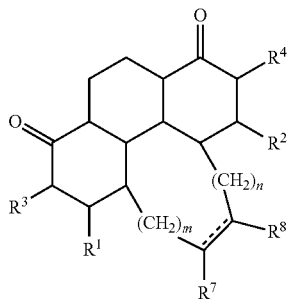

XI wherein:
m and n are selected from 0 or 1; and
each occurrence of $R^1$, $R^2$, $R^3$, $R^4$, $R^7$, and $R^8$ is independently selected from hydrogen, alkyl, and dialkyl.

The disclosed polycyclic molecules may be prepared by reacting precursors that include: cyclohexanone derivative precursors having vinyl and/or allyl group substitutions at the 5-position or 6-position and/or alkyl vinyl ketones. The precursors are combined through the formation of symmetrical or unsymmetrical silyl bis-enol ethers via reaction with a dialkyl silyl dihalide (e.g., $iPr_2SiCl_2$), followed by sequential oxidative coupling and ring-closing metathesis of the symmetrical or unsymmetrical silyl bis-enol ethers to provide the polycyclic molecules.

Also disclosed are pharmaceutical compositions that comprise the disclosed compounds together with a carrier, diluent, or excipient. The pharmaceutical compositions may comprise an effective amount of the compounds (or salts, solvates, or epoxides thereof) for treating and/or preventing a disease, disorder, or condition which may include cell proliferation diseases, disorders, or conditions, such as cancer.

Also disclosed are methods of treating cancer that include administering the disclosed compounds, for example, where the compounds are formulated as a pharmaceutical composition and administered to a patient having cancer or suspected of having cancer. Cancers treated by the disclosed methods may include, but are not limited to multiple myeloma, leukemia, non-small cell lung cancer, colon cancer, cancer of the central nervous system, melanoma, ovarian cancer, renal cancer, prostate cancer, breast cancer including metastatic breast cancer, and cervical cancer.

DETAILED DESCRIPTION

Figure 1:
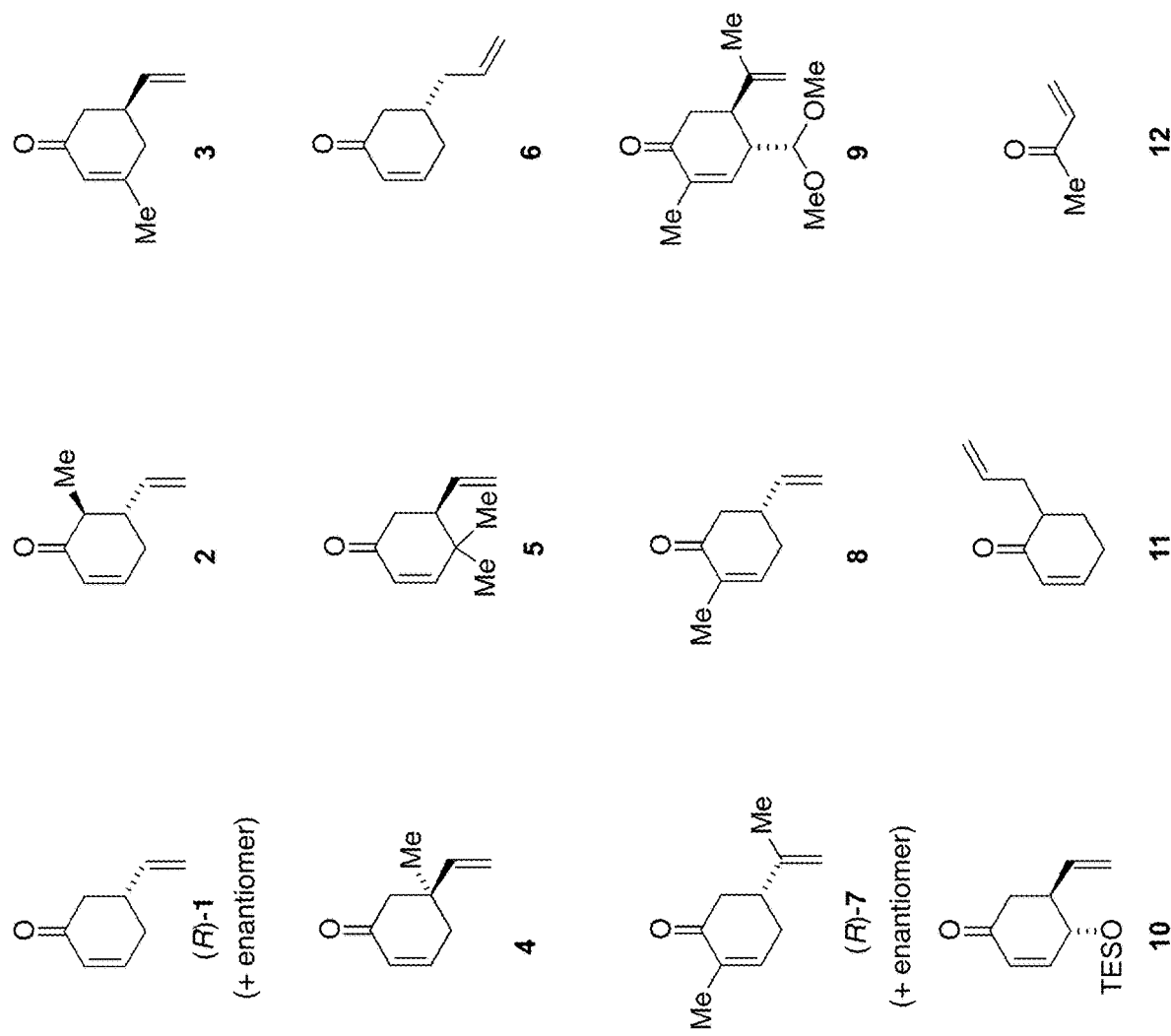
FIG. 1. Enone building blocks selected for exploration of the oxidative coupling/ring-closing metathesis strategy for accessing polycyclic compounds.

The disclosed subject matter further may be described utilizing terms as defined below.

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

As used herein, an asterick "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of an alkyl group. An exemplary alkylene group is —$CH_2CH_2$—.

The term "haloalkyl" refers to an alkyl group that is substituted with at least one halogen. For example, —$CH_2F$, —$CHF_2$, —$CF_3$, —$CH_2CF_3$, —$CF_2CF_3$, and the like The term "heteroalkyl" as used herein refers to an "alkyl" group in which at least one carbon atom has been replaced with a heteroatom (e.g., an O, N, or S atom). One type of heteroalkyl group is an "alkoxyl" group The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloalkylene" refers to a diradical of a cycloalkyl group.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3-to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines, wherein substituents may include, for example, alkyl, cycloalkyl, heterocyclyl, alkenyl, and aryl.

The terms "alkoxyl" or "alkoxy" are art-recognized and refer to an alkyl group, as defined above, having an oxygen radical attached thereto. Representative alkoxyl groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

An "epoxide" is a cyclic ether with a three-atom ring typically that includes two carbon atoms and whose shape approximates an isosceles triangle. Epoxides can be formed by oxidation of a double bound where the carbon atoms of the double bond form an epoxide with an oxygen atom.

The term "carbonyl" as used herein refers to the radical —C(O)—.

The term "carboxamido" as used herein refers to the radical —C(O)NRR', where R and R' may be the same or different. R and R' may be independently alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" as used herein refers to a radical of the form —R$^1$C(O)N(R$^2$)—, —R$^1$C(O)N(R$^2$)R$^3$—, —C(O)N R$^2$ R$^3$, or —C(O)NH$_2$, wherein R$^1$, R$^2$ and R$^3$ are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereo isomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. In addition, spirocyclic derivatives of the disclosed polycyclic compounds are contemplated herein. Compositions comprising substantially purified stereoisomers, epimers, enantiomers, analogs or derivatives thereof are contemplated herein (e.g., a composition comprising at least about 90%, 95%, or 99% pure stereoisomer, epimer, enantiomer, analog, or derivative.)

As used herein, the term "modulate" means decreasing or inhibiting activity and/or increasing or augmenting activity. For example, modulating cell growth activity means decreasing or inhibiting cell growth. Modulating cell growth may include killing cells.

As used herein, a "subject" may be interchangeable with "patient" or "individual" and means an animal, which may be a human or non-human animal, in need of treatment. A "subject in need of treatment" may include a subject having a disease, disorder, or condition that is responsive to therapy with the polycyclic compounds disclosed herein. For example, a "subject in need of treatment" may include a subject having a cell proliferative disease, disorder, or condition such as cancer (e.g., cancers such as multiple myeloma, leukemia, non-small cell lung cancer, colon cancer, cancer of the central nervous system, melanoma, ovarian cancer, renal cancer, prostate cancer, breast cancer including metastatic breast cancer, and cervical cancer).

The disclosed compounds may be effective in inhibiting cell proliferation of cancer cells. For example, the disclosed compound may be effective in inhibiting cell proliferation of one or more types of cancer cells including: multiple myeloma cells, such as MM.1S cells; leukemia cells, such as CCRF-CEM, HL-60(TB), MOLT-4, RPMI-8226 and SR; non-small lung cancer cells, such as A549/ATCC, EKVX, HOP-62, HOP-92, NCI-H226, NCI-H23, NCI-H322M, NCI-H460 and NCI-H522; colon cancer cells, such as COLO 205, HCC-2998, HCT-116, HCT-15, HT29, KM12 and SW-620; CNS: SF-268, SF-295, SF-539, SNB-19, SNB-75 and U251; melanoma cancer cells, such as LOX IMVI, MALME-3M, M14, MDA-MB-435, SK-MEL-2, SK-MEL-28, SK-MEL-5, UACC-257 and UACC-62; ovarian cancer cells, such as IGR-OV1, OVCAR-3, OVCAR-4, OVCAR-5, OVCAR-8, NCI/ADR-RES and SK-OV-3; renal cancer cells, such as 786-0, A498, ACHN, CAKI-1, RXF 393, SN12C, TK-10 and UO-31; prostate cancer cells, such as DU-145 and PC-3; and breast cancer cells, such as MCF7, MDA-MB-231/ATCC, MDA-MB-468, HS 578T, BT-549 and T-47D. Cell proliferation and inhibition thereof by the presently disclosed compounds may be assessed by cell viability methods disclosed in the art including but not limited to colorimetric assays that utilize dyes such as MTT, XTT, and MTS to assess cell viability.

Preferably, the disclosed compounds are effective in inhibiting cell proliferation of cancer cells. Preferably, the disclosed compounds are effective in inhibiting cell proliferation of cancer cells and have an IC50 of less than about 10 μM, 5 μM, 1 μM, 0.5 μM, 0.1 μM, 0.05 μM, 0.01 μM or lower in the selected assay (or have an IC50 within a range bounded by any of these values, such as 0.1-0.01 μM).

Preferably, the disclosed compounds do not inhibit cell proliferation of normal cells. If the disclosed compounds inhibit cell proliferation of normal cells, preferably, the disclosed compounds have an IC50 that is greater than about 1 μM, 5 μM, 10 μM, 50 μM, 100 μM, 500 μM, 1000 μM, or higher in the selected assay.

Preferably, the disclosed compounds are effective in inhibiting cell proliferation of cancer cells selectively relative to normal cells. For example, the disclosed compound may have an IC50 for inhibiting cell proliferation of cancer cell ($IC50_{cancer}$) that is greater an IC 50 for inhibiting cell proliferation of normal cells ($IC50_{normal}$). In some embodiments, the ratio $IC50_{normal}/IC50_{cancer}$ is greater than about 10, 50, 100, 500, 1000, 5000, 10000, or higher.

The compounds utilized in the methods disclosed herein may be formulated as pharmaceutical compositions that include: (a) a therapeutically effective amount of one or more compounds as disclosed herein; and (b) one or more pharmaceutically acceptable carriers, excipients, or diluents. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to 100 mg/kg body weight (preferably about 0.5 to 20 mg/kg body weight, more preferably about 0.1 to 10 mg/kg body weight). In some embodiments, after the pharmaceutical composition is administered to a patient (e.g., after about 1, 2, 3, 4, 5, or 6 hours post-administration), the concentration of the compound at the site of action is about 2 to 10 μM.

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™). Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The compounds utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules.

The compounds utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the compounds may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

For applications to the eye or other external tissues, for example the mouth and skin, the pharmaceutical compositions are preferably applied as a topical ointment or cream. When formulated in an ointment, the compound may be employed with either a paraffinic or a water-miscible ointment base. Alternatively, the compound may be formulated in a cream with an oil-in-water cream base or a water-in-oil base. Pharmaceutical compositions adapted for topical administration to the eye include eye drops where the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or enemas.

Pharmaceutical compositions adapted for nasal administration where the carrier is a solid include a coarse powder having a particle size (e.g., in the range 20 to 500 microns) which is administered in the manner in which snuff is taken (i.e., by rapid inhalation through the nasal passage from a container of the powder held close up to the nose). Suitable formulations where the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurized aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

The compounds for use according to the methods of disclosed herein may be administered as a single compound or a combination of compounds. For example, a compound that treats cancer activity may be administered as a single compound or in combination with another compound that treats cancer or that has a different pharmacological activity.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-.1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, alpha-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

The pharmaceutical compositions may be utilized in methods of treating a disease or disorder associated with aberrant cell proliferation such as cancer. As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating a cell proliferative disease or disorder.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

EXAMPLES

The following Examples are illustrative only and are not intended to limit the scope of the claimed subject matter.

Example 1

Title—a Strategy for the Convergent and Stereoselective Assembly of Polycyclic Molecules Reference is made to Emily E. Robinson and Regan J. Thomson, "A Strategy for the Convergent and Stereoselective Assembly of Polycyclic Molecules," J. Am. Chem. Soc. 2018, 140, 1956-1965, published Jan. 8, 2018, and Correction to "A Strategy for the Convergent and Stereoselective Assembly of Polycyclic Molecules," J. Am. Chem. Soc. 2018, 140, 7043-7043, published May 21, 2018, the contents of which are incorporated herein by reference in their entireties.

Abstract

The stereoselective oxidative coupling of cyclic ketones via silyl bis-enol ethers followed by ring-closing metathesis is shown to be a general and powerful reaction sequence for the preparation of diverse polycyclic scaffolds from simple precursors. The modular strategy successfully constructs substructures prevalent in numerous bioactive natural product families, varying in substitution and carbocyclic composition. Several of the prepared compounds were shown to possess potent cytotoxic activity against a panel of tumor cell lines. The utility of this strategy was further demonstrated by a concise and highly convergent 17-step formal synthesis of the complex antimalarial marine diterpene, (+)-7,20-diisocyanoadociane.

Introduction

The success of many synthetic routes towards complex molecules is usually highly dependent upon developing a convergent strategy that allows for the efficient assembly of molecular fragments in a reliable manner. During retrosynthetic planning,[1] application of transforms that allow for the disconnection of the target into two or more pieces with the simultaneous clearance of complicating stereogenic elements leads to a powerfully simplifying approach. Execution of these general concepts is often straightforward for the synthesis of acyclic compounds where convergency is readily obtained, but can be significantly more problematic when designing synthesis plans for polycyclic molecules. These compounds do not lend themselves to immediate disconnection into similarly sized fragments and they often necessitate bond-forming reactions within sterically hindered and strained environments. These challenges may be one reason why complex sp[3]-rich polycyclic species have been underrepresented in many drug discovery efforts.[2] Instead, much effort has focused on the synthesis of diverse sp[2]-rich molecules, despite the recognition that such compounds often possess undesirable properties that limit clinical success.[3] Lovering and coworkers speculated that this situation arose because methods such as transition metal cross-coupling are so reliable at generating large libraries of compounds, thereby biasing efforts at the bench.[3] The development of comparable reactions and strategies to access stereochemically complex polycyclic scaffolds,[4-10] therefore, represents an important area for continued development in order to address these issues.

Within this context, oxidative enolate coupling has emerged as a powerful tool for accessing complex molecular architectures,[11-12] as highlighted by a number of recent total syntheses employing the reaction.[13-21] While the earliest example of oxidative enolate coupling dates back to 1935,[22] the 1970s saw the advent of synthetically useful variants due to the pioneering contributions from the labs of both Rathke[23] and Saegusa.[24-25] Recent years have seen a reinvigoration of interest in methods for achieving oxidative enolate coupling. For example, in 2006, Baran and DeMartino introduced new methods for the oxidative cross-coupling of amide- and ketone-derived enolates.[15, 26] Flowers and Casey studied the oxidative cross-coupling of two ketone-derived lithium enolates and concluded that efficient cross-coupling resulted from favorable formation of heteroaggregates in solution.[27] In 2007, MacMillan and coworkers reported an enantioselective method for oxidative coupling of aldehydes using enamine catalysis,[28-31] while Daugulis and coworkers reported an oxidative coupling process catalytic in metal oxidant.[32] Moeller's group has devised a number of related electrochemically-induced bond forming processes.[33]

Our interest in this class of reactions stemmed from an initial desire to expand the use of silyl bis-enol ethers, first reported by Schmittel and coworkers in 1998,[34] for the generation of quaternary stereocenters and linked bicyclic 1,4-diketones.[35-37] Subsequent work from our lab demonstrated the utility of oxidative coupling for the synthesis of several natural products.[38-41] These syntheses took advantage of the crucial oxidative coupling event to generate concise and convergent approaches to specific carbocyclic (and heterocyclic) skeletons associated with the natural products of interest. During the course of these target-directed studies, we recognized that oxidative coupling might be an enabling reaction upon which to establish a general approach for accessing diverse carbocyclic skeletons from a common set of simple precursors. More specifically, we wished to devise a convergent strategy for accessing a range of stereochemically-rich polycyclic compounds that would enable the rapid disconnection of rings and clearance of stereocenters during retrosynthetic planning. The scaffolds thus prepared comprise the core structures of many bioactive natural product families, and as such, efficient access to these compounds may facilitate the discovery of novel small molecules for further biological investigation. Inclusion of such scaffolds in drug discovery programs may enhance the degree of chemical space that can be probed during biological screens.[2-3] Herein, we report the development of such a strategy to access a suite of carbocyclic compounds from a set of common precursors.

The general outline of our approach, which is based on the sequential use of oxidative coupling and ring-closing metathesis, is shown in Scheme 1. We envisioned that relatively simple, optically-enriched cyclohexenone derivatives substituted at the 5-position with an appropriate vinyl or allyl group (i.e., generic structures I and II, respectively) would form the basis of our strategy. The use of enantioenriched starting materials was essential in order to avoid the generation of intractable mixtures of diastereomers resulting from the union of racemic precursors. The choice of enones as starting materials would allow for complete regiocontrol during silyl bis-enol ether formation, ensuring that subsequent oxidative carbon-carbon bond formation would occur in the desired manner. Thus, the enone building blocks could be united in any desired combination through the formation of symmetrical or unsymmetrical silyl bis-enol ethers (i.e., III), which would then undergo sequential oxidative coupling and ring-closing metathesis, to deliver tricyclic compounds (i.e., VII-IX) containing four contiguous stereocenters with various ring structures. Elaboration of the carbocyclic products formed through this sequence by manipulation of the embedded alkene and carbonyl functionality would serve as a means for further diversification and processing.

Scheme 1. General strategy for accessing diverse polycyclic scaffolds from a simple set of common precursors through an oxidative coupling and ring-closing metathesis sequence. The use of silyl bis-enol ethers allows the controlled coupling of enones I and II in any combination to generate tricyclic products whose central ring varies in size.

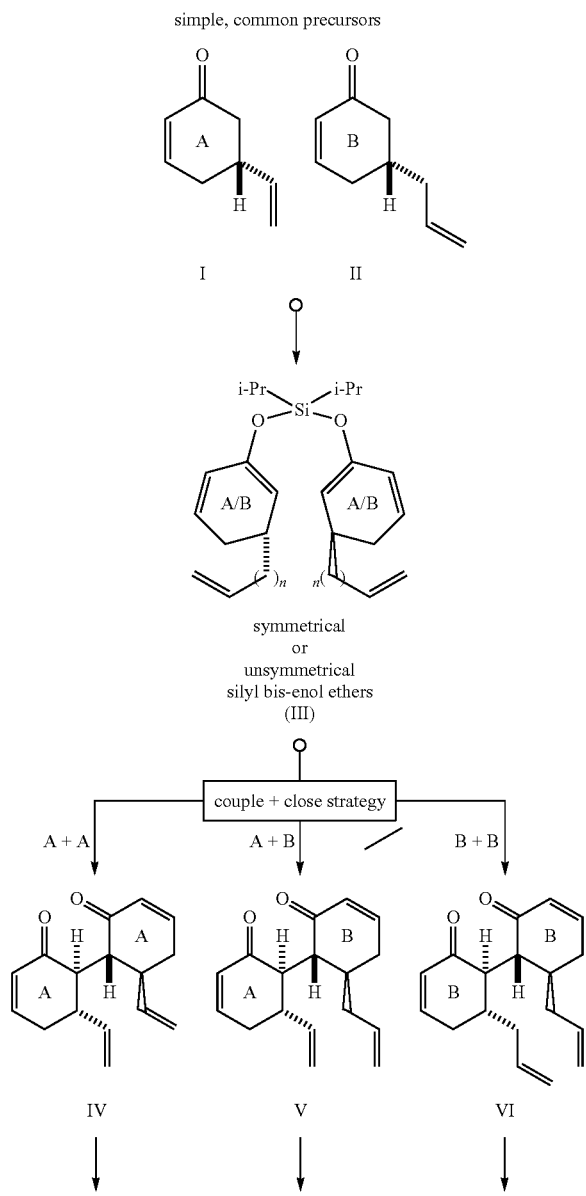

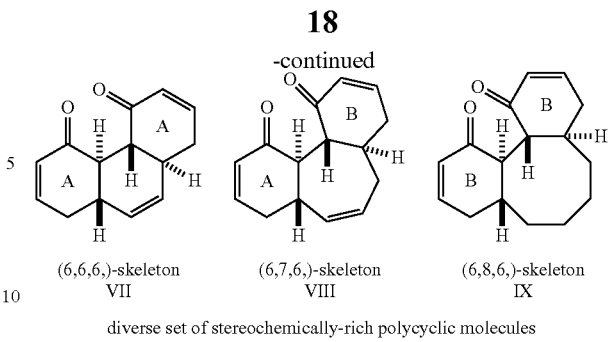

diverse set of stereochemically-rich polycyclic molecules

Results and Discussion

Development of a Couple & Close Strategy to Access Diverse Ring Systems.

We selected twelve enones to begin our initial investigation (i.e., 1-12 in FIG. 1). The choice of these particular enones was predicated on a combination of their accessibility in optically pure form (where appropriate), their commercial availability or ease of synthesis, and because the products formed after oxidative coupling and ring-closure mapped onto substructures of interest to us. (R)- and (S)-carvone [(R)-7 and (S)-7] and methylvinylketone (12) are commercially available, while compounds 1-6 were prepared in 99% ee from (5R)-trimethylsilylcyclohexenone as a readily available chiral synthon.[42-45] Compounds 8[46-47] and 9[48] could be easily made from (R)- or (S)-carvone, respectively. Enone 10 could be produced from commercially available (−)-quinnic acid,[49] and a simple allylation of cyclohexenone delivered enone 11.[50] Full details for the synthesis of these building blocks can be found in the Supporting Information section.

Figure 2:
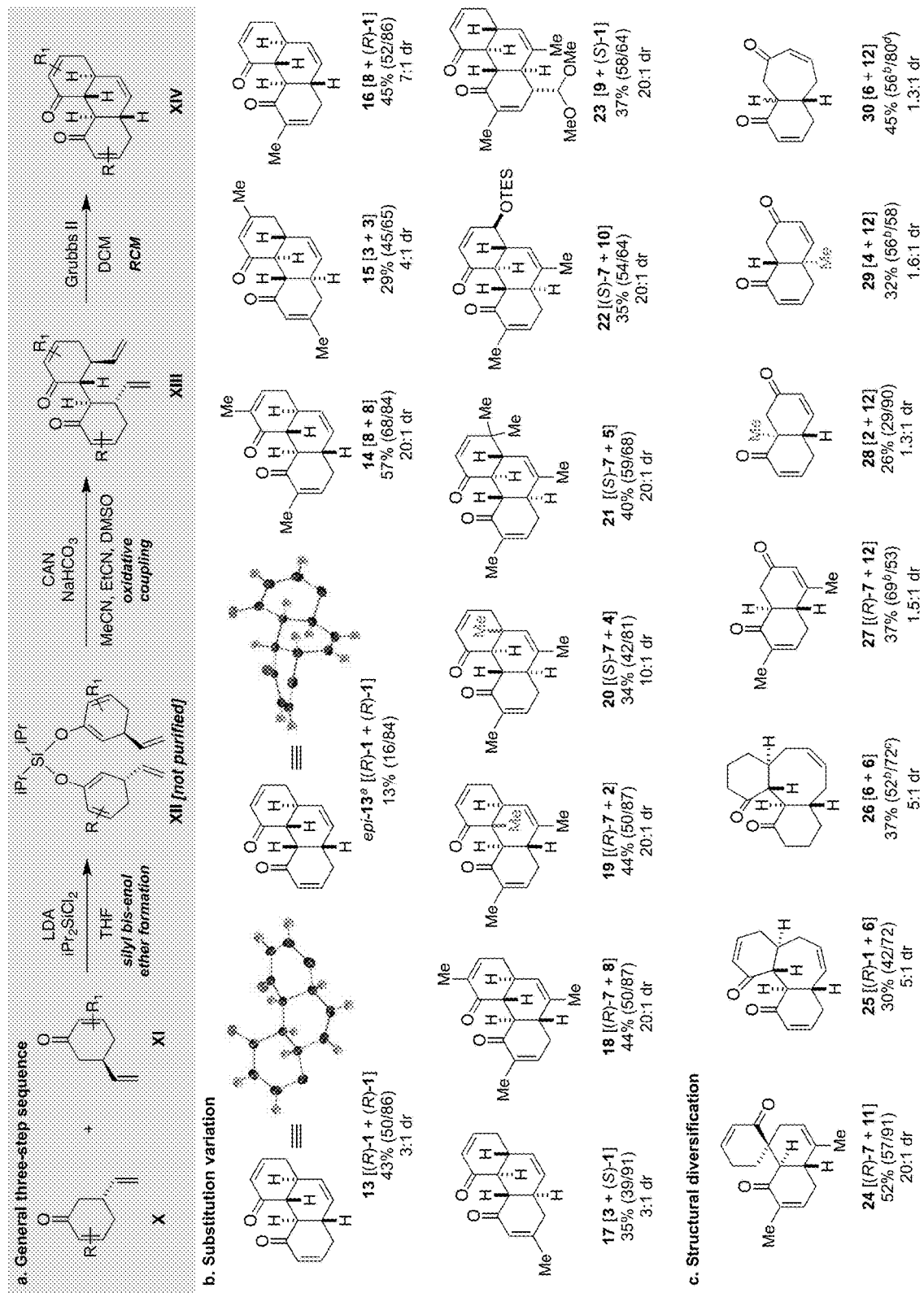
FIG. 2. Couple & close strategy employing a diastereoselective oxidative coupling and subsequent ring-closing metathesis sequence to fashion fused carbocyclic scaffolds from simple ketone building blocks. The flexible and general approach (a) enables straightforward alteration of substitution patterns (b) and structural modification (c) of the constructed carbocyclic scaffolds. Total percent yields for the major isomer obtained over three steps are shown, with yields for the combined silyl bis-enol ether formation/oxidative coupling and ring-closing metathesis shown in parentheses. Diastereoselectivities were determined by $^1$H NMR spectroscopic analysis of unpurified reaction mixtures following oxidative coupling. [a]epi-13 was prepared from the RCM of the minor diastereomer isolated from the oxidative dimerization of (R)-1. [b]Diastereomers from the oxidative coupling step were inseparable by flash chromatography. [c]Two-step yield from conjugate reduction and RCM. [d]Diastereomers were inseparable by flash chromatography after RCM.

With a suitable collection of enone building blocks in place, we began an exploration of the chemical space we could access using our proposed couple & close strategy (FIG. 2). The requisite silyl bis-enol ethers were prepared using either one of two general methods: for symmetrical systems the silyl bis-enol ethers were prepared by the addition of 0.5 equivalents of dichlorodiisopropylsilane to the lithium enolate of the desired enone monomer (X or XI), while unsymmetrical silyl bis-enol ethers were accessed by the sequential addition of each enone-derived lithium enolate to one equivalent of dichlorodiisopropylsilane. For this latter protocol, the rate of addition of the second enolate to the intermediate monochloro enol silane (not shown) is markedly slower than the initial addition, thus generation of undesired symmetrical species is minimized. Oxidative coupling of the silyl bis-enol ether species (i.e., XII) was carried out directly without purification, and was best achieved using ceric ammonium nitrate as the stoichiometric oxidant. Subsequent ring-closing metathesis of the purified 1,4-diketone adducts (i.e., XIII) was most effective when Grubbs II was utilized.[51]

All examples shown in FIG. 2 were generated using this standard three-step protocol, with yields reported for final products over the entire sequence, and individual yields for 1,4-diketone synthesis and ring-closing metathesis given in parentheses. Reported diastereoselectivities refer to the outcome of the oxidative coupling step.

Our initial experiments focused on the generation of symmetrical products derived from the dimerization of simple enone precursors (R)-1, 3 and 8. The "parent" vinyl-substituted cyclohexenone (R)-1 underwent effective oxidative coupling to generate the corresponding symmetrical 1,4-diketone in 66% yield as a separable 3:1 mixture of stereoisomers. The major isomer underwent smooth ring-closure to form tricyclic species 13 in 86% yield. Thus, in three simple operations, the stereochemically-rich dienone 13, whose structure was confirmed by single crystal X-ray analysis, was accessed in an overall yield of 43% from enone (R)-1. The minor isomer generated during oxidative coupling underwent ring-closing metathesis to deliver the isomeric tricyclic dienone epi-13, which was also amenable to X-ray analysis.

The trans-anti-trans stereochemistry of the major product 13 is consistent with a working stereochemical model whereby the newly forged carbon-carbon bond generated through oxidative coupling forms preferentially opposite both β-substituents through a conformation akin to XV (FIG. 3).[36] This favored "staggered" conformation not only avoids unfavorable interactions between the β-substituents, it also arranges each cyclohexadiene ring in an orientation that avoids destabilizing ring-to-ring eclipsing interactions that are present within alternative conformer XVI. The "eclipsed" conformer XVI, which leads to the formation of the minor stereoisomer XIX (and then to epi-13), whereby the new bond is generated syn to one of the β-substituents is, however, still lower in energy than the alternative "staggered" conformer XVII. We never observed products arising from this highly disfavored arrangement that necessitates forming a carbon-carbon bond syn to both β-substituents.

Figure 3:
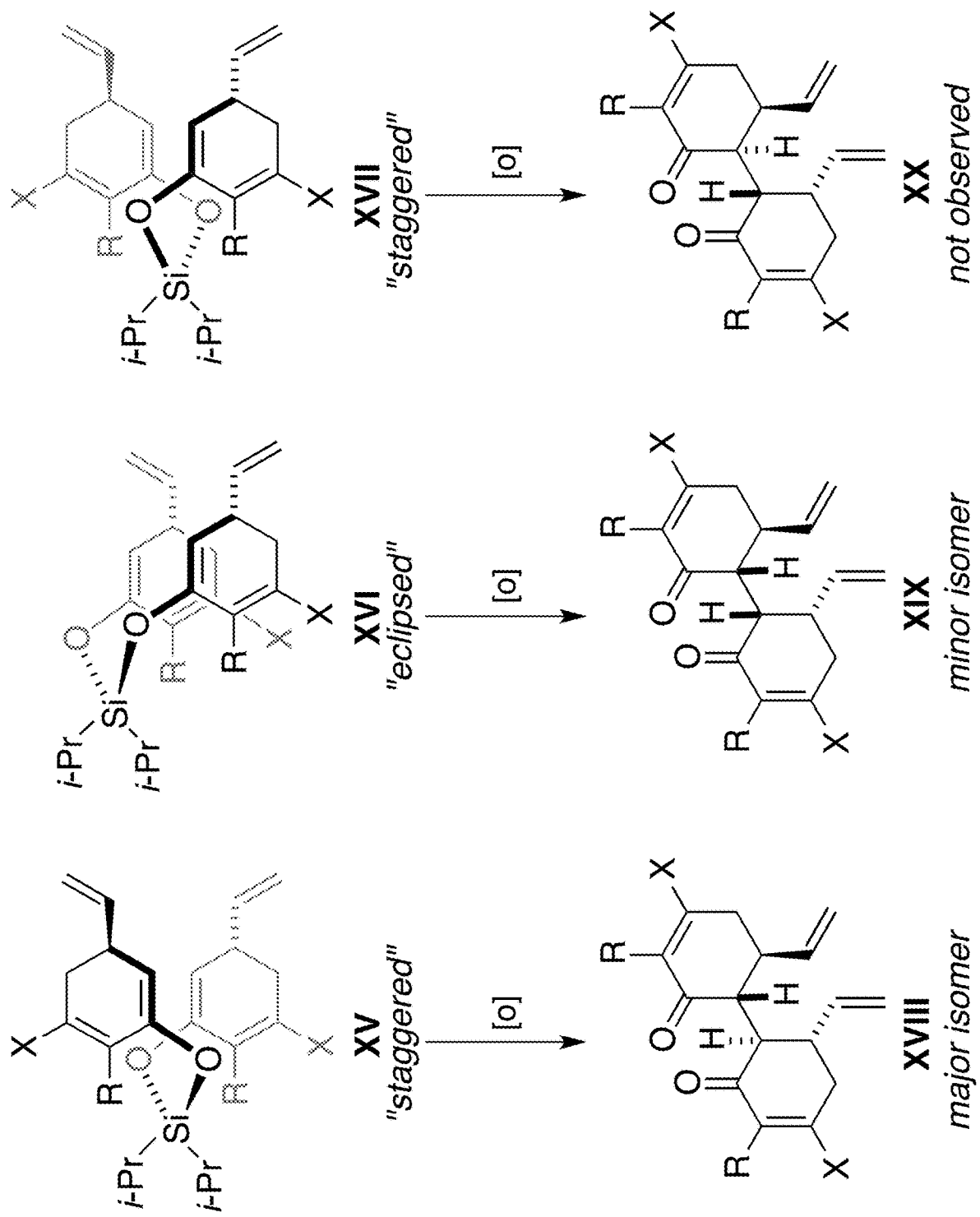
FIG. 3. Stereochemical model for oxidative coupling.

Experiments probing substituent effects on coupling selectivity revealed a marked enhancement in observed diastereoselectivity for substrates bearing substitution at the 2-position of the enone. For example, the oxidative dimerization and ring-closing metathesis of enone 8 gave rise to scaffold 14 in 57% yield with a 20:1 dr. As shown in FIG. 3, the observed enhancement of selectivity when R=Me vs. R=H is most likely attributed to greater destabilizing interactions between the 2-methyl substituents in the "eclipsed" conformer XVI relative to "staggered" conformer XV. On the other hand, substitution at the 3-position as in enone 3 delivered the desired tricyclic product 15 as a 4:1 mixture of stereoisomers, an outcome difficult to rationalize using simple models. One possible explanation is that because the 3-substituents (i.e., when X=Me in FIG. 3) are located further from the site of bond formation they are subject to reduced destabilizing steric interactions within minor conformer XVI during bond formation. Alternatively, substituents located at the 3-position are unlikely to interact with the diisopropyl groups on silicon, meaning that the observed diastereoselectivity is determined primarily due to contributions from the β-substituents.

The impact of the silicon tether for the dimerization of β-substituted cyclohexenones was definitively established through its ability to augment coupling diastereoselectivity relative to non-tethered reactions. For example, dimerization of enone 8 by treating its lithium enolate with FeCl$_3$ under conditions developed for ketone dimerization by Frazier and Harlow,[52] provided a 3:1 mixture of diastereomers, whereas the silicon-templated approach delivered the product with an enhanced a 20:1 diastereoselectivity. The capacity of the silicon tether to both enhance diastereoselectivity and control the cross-coupling of ketones allowed us to generate a suite of more complex phenathrene-type products (i.e., 16-23). Use of (R)-carvone [(R)-7] and enone 8 allowed for the efficient synthesis of dienone 18, demonstrating that the strategy can be used successfully to access products containing trisubstituted olefins. In this instance, the initial oxidative coupling step afforded the 1,4-diketone in 50% yield and with 20:1 diastereoselectivity, while attempted FeCl$_3$-mediated oxidative coupling of a 1:1 mixture of lithium enolates derived from (R)-7 and enone 8 delivered a complex the mixture of dimeric and cross-coupled products, further highlighting the value of this silicon-templated strategy. We were particularly interested in providing convergent routes to compounds possessing quaternary centers, since these structural motifs are present within a myriad of terpene natural products. The coupling of enone 2 with (R)-7 allowed for the synthesis of tricyclic species 19 as a 20:1 ratio of diastereomers in 44% yield. The ability to form quaternary stereocenters during the convergent oxidative coupling step of the sequence highlights the potential utility of this method for installing the angular methyl group common among numerous terpenes. The reaction sequence also tolerated the presence of pre-existing quaternary centers within the starting materials, such that enone 4 and (S)-carvone [(S)-7] underwent oxidative coupling and ring-closure to produce dienone 20 in 34% yield (10:1 dr). Enones possessing several different substituents at the 4-position (i.e., 5, 9 and 10) also provided the desired tricyclic frameworks with good overall yields and high levels of stereocontrol. For example, gem-dimethyl-containing enone 5 underwent smooth coupling with (S)-7 to deliver dione 21 in 40% yield (20:1 dr), further highlighting the tolerance of the protocol towards the presence of sterically congested groups. The preparation of tricyclic species 22 and 23, derived from functionalized monomeric enones 10 and 9, respectively, allowed for the rapid synthesis of products containing useful functional groups (i.e., a protected alcohol and a masked aldehyde) that could be revealed in high yield (see Supporting Information). While the strategy was tolerant of a variety of substitution patterns and functional groups, oxidative coupling to produce very sterically-demanding substrates proved challenging. We had hoped, for example, to use our method for the diastereoselective formation vicinal quaternary centers. However, explorations on the dimerization of enone 2 yielded only aromatized monomers, and none of the desired 1,4-diketone.

In an effort to diversify the carbocyclic scaffolds generated through this method, we targeted structures departing from the phenanthrene-type core (FIG. 2c). Use of α-allylcyclohexanone 11 provided an opportunity to investigate the impact of changing the position of the tethered alkene group that would undergo ring-closing metathesis. Thus, the oxidative coupling of enone 11 and (R)-carvone [(R)-7] afforded an intermediate 1,4-diketone (20:1 dr), which underwent smooth cyclization to yield the spirofused tricyclic species 24 in 52% yield over the three steps. Confirmation of the structural assignment of 24 was established through 2D NMR spectroscopy and correlation to the X-ray crystal structure of the intermediate 1,4-diketone (see Supporting Information for full details). Moving the allyl substituent to the 5-position of the starting enone, as in substrate 6, opened the prospect of generating tricyclic products where the central ring formed through metathesis contained seven or eight carbons rather than six. The oxidative cross-coupling and ring-closure of enones (R)-1 and 6 generated the 6,7,6-tricyclic dienone 25 in 30% yield with 5:1 diastereoselectivity for the trans-anti-trans-configuration. Initial efforts to construct the corresponding 6,8,6-ring system through the dimerization and ring-closing metathesis of enone 6 were unsuccessful. While the oxidative dimerization of 6 proceeded with satisfactory yields (52%, 5:1 dr), subsequent ring-closing metathesis delivered the 7-membered ring product 25 rather than the anticipated 8-membered ring product; a consequence of alkene isomerization prior to ring-closure. Related alkene isomerizations have been observed previously during attempted ring-closing metatheses. Mechanistic and structural investigations by Grubbs and coworkers established the identity of the ruthenium hydride species responsible for these isomerizations, and showed that additives such as 1,4-benzoquinone suppressed its formation and led to effective metathesis without competing alkene migration.[53-54] In our system, although inclusion of 1,4-benzoquinone as an additive did indeed inhibit alkene isomerization, we did not observe ring-closing metathesis, instead only unchanged starting material was recovered. We hypothesized that the desired cyclooctene product was disfavored energetically due to conformational strain imparted by the presence of so many $sp^2$-hybridized atoms in the fused ring system. In support of this hypothesis, conjugate reduction of the enones prior to ring-closing metathesis allowed for the synthesis of the desired 6,8,6-ring system 26 in 37% yield (over four steps from 6) without any observable products derived from alkene isomerization.

While our focus was primarily on the formation of tricyclic species derived from cyclic enone starting materials (i.e., 1-11), we also wished to demonstrate that the strategy could be utilized to access bicyclic products. To this end, we engaged methylvinyl ketone (12) as a coupling partner with several cyclohexenones. When paired with (R)-carvone [(R)-7] the trans-fused decalin adduct 27 was formed in good yield (37% over three steps), but with disappointingly low levels of diastereocontrol. In a similar fashion, the use of methylvinyl ketone (12) with enones 2 and 4, respectively, resulted in the preparation of bicyclic products bearing quaternary centers in the α- and β-positions (28 and 29). Likewise, the 6,7-ring-expanded bicyclic species (30) was achieved by coupling methylvinyl ketone (12) with enone 6.

Substrate Manipulations.

The products obtained from this couple & close strategy may be manipulated through a number of chemoselective transformations to deliver a variety of new functional groups and modified scaffolds (Scheme 2).

Scheme 2. Chemo- and stereoselective transformations of dienones.

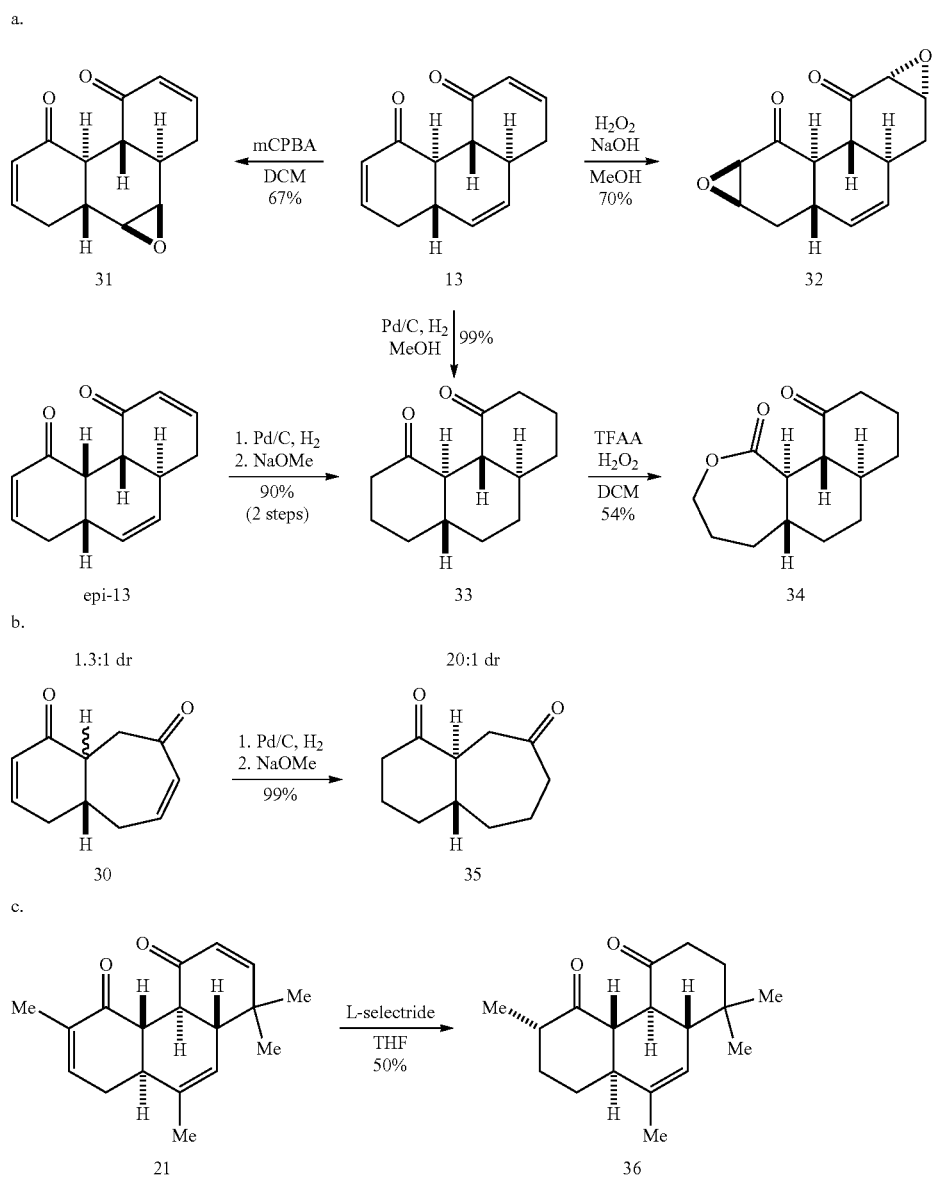

For example, the simplest variant of the methodology (i.e., 13) was converted to monoepoxide 31 by selective oxidation of the isolated alkene with mCPBA (Scheme 2a). On the other hand, treatment of 13 with hydrogen peroxide and sodium hydroxide allowed for nucleophilic epoxidation of the enone groups to deliver bis-epoxide 32 as a single diastereomer. Global hydrogenation of 13 generated saturated diketone 33 in quantitative yield, which allowed for the synthesis of lactone 34 by a Baeyer-Villiger reaction on one of the ketone groups. The minor stereoisomer obtained from the oxidative dimerization and ring-closing metathesis of enone (R)-1 (i.e., epi-13) could be converted to the all trans-adduct 33 after initial reduction followed by base-induced epimerization. Similarly, bicyclic enone 30, which was formed with low levels of diastereocontrol during the oxidative coupling step, could be converted to the more stable trans-isomer 35 (Scheme 2b). These results indicate that for certain systems where poor control is observed during oxidative coupling, subsequent epimerization can lead to efficient conversion of the mixture to the most thermodynamically favored isomer. Lastly, we showed that reduction of the enone functionality could be conducted without reduction of the isolated alkene (Scheme 2c). In this example, reduction of bis-enone 21 with L-selectride delivered dione 36 in 50% yield with selective introduction of a new stereogenic center.

Biological Evaluation of Selected Scaffolds.

Figure 4:
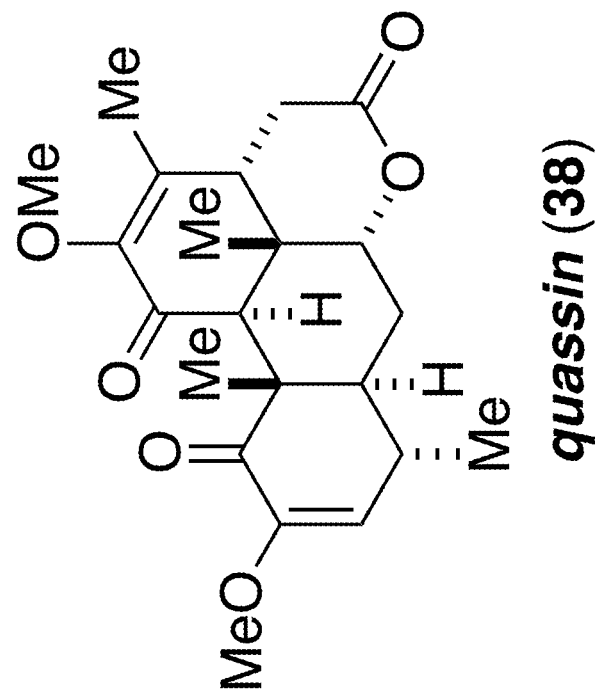
FIG. 4. Bioactive enone-containing polycyclic molecules.
Figure 4:
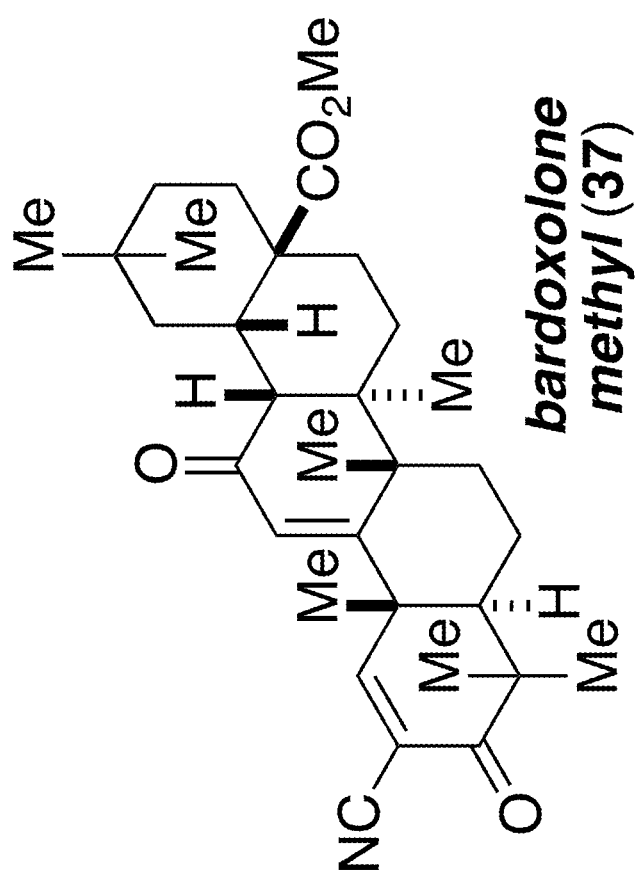
Figure 5:
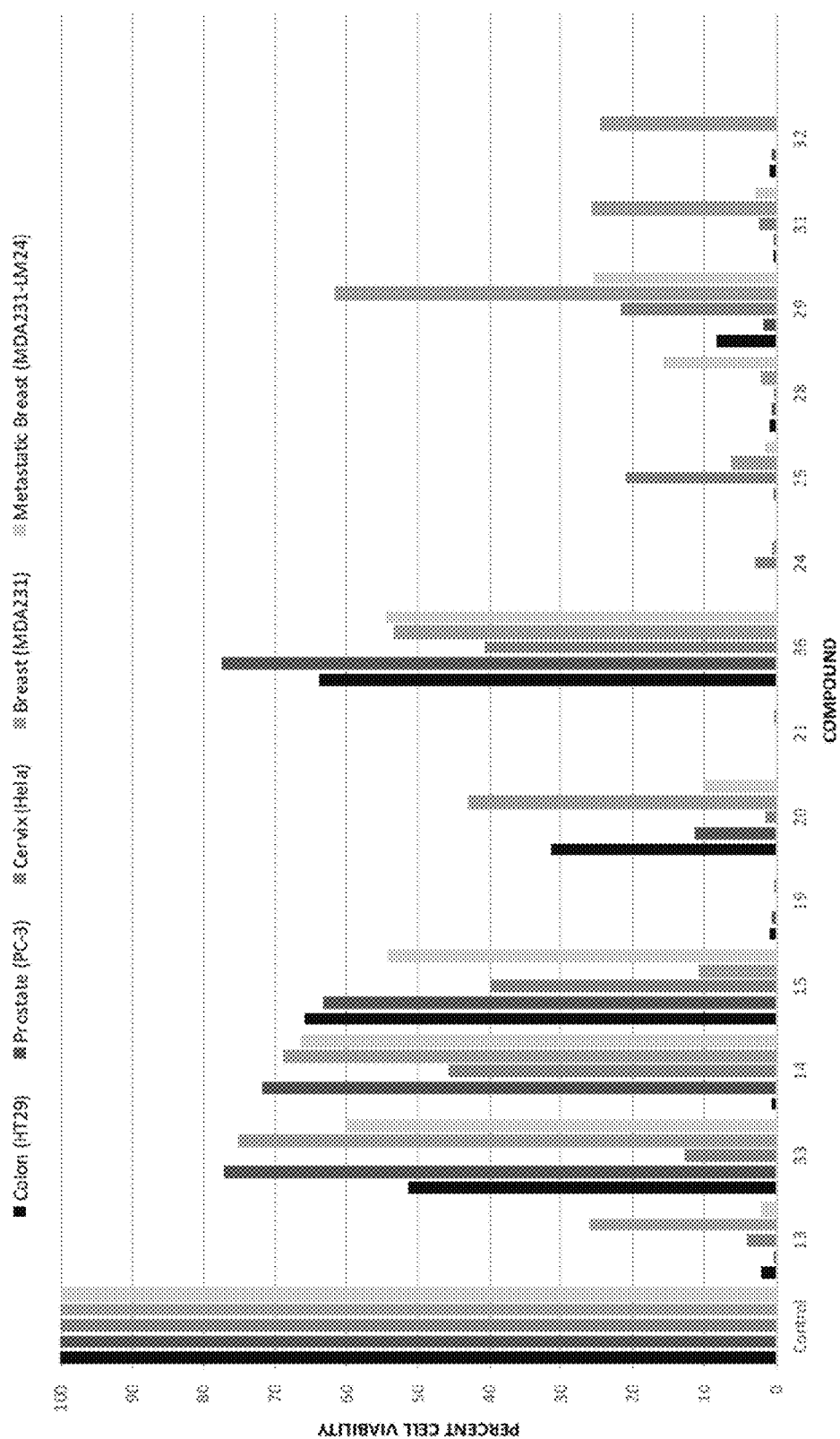
FIG. 5. Percent cell viability of a selection of tumor ell lines when treated with mM prepared compound in DMSO (Colon: HT29, Prostate: PC-3, Cervix: Hela, Breast: MDA-MB-231, Metastatic breast: MDA-MB-231-LM24).
Figure 6:
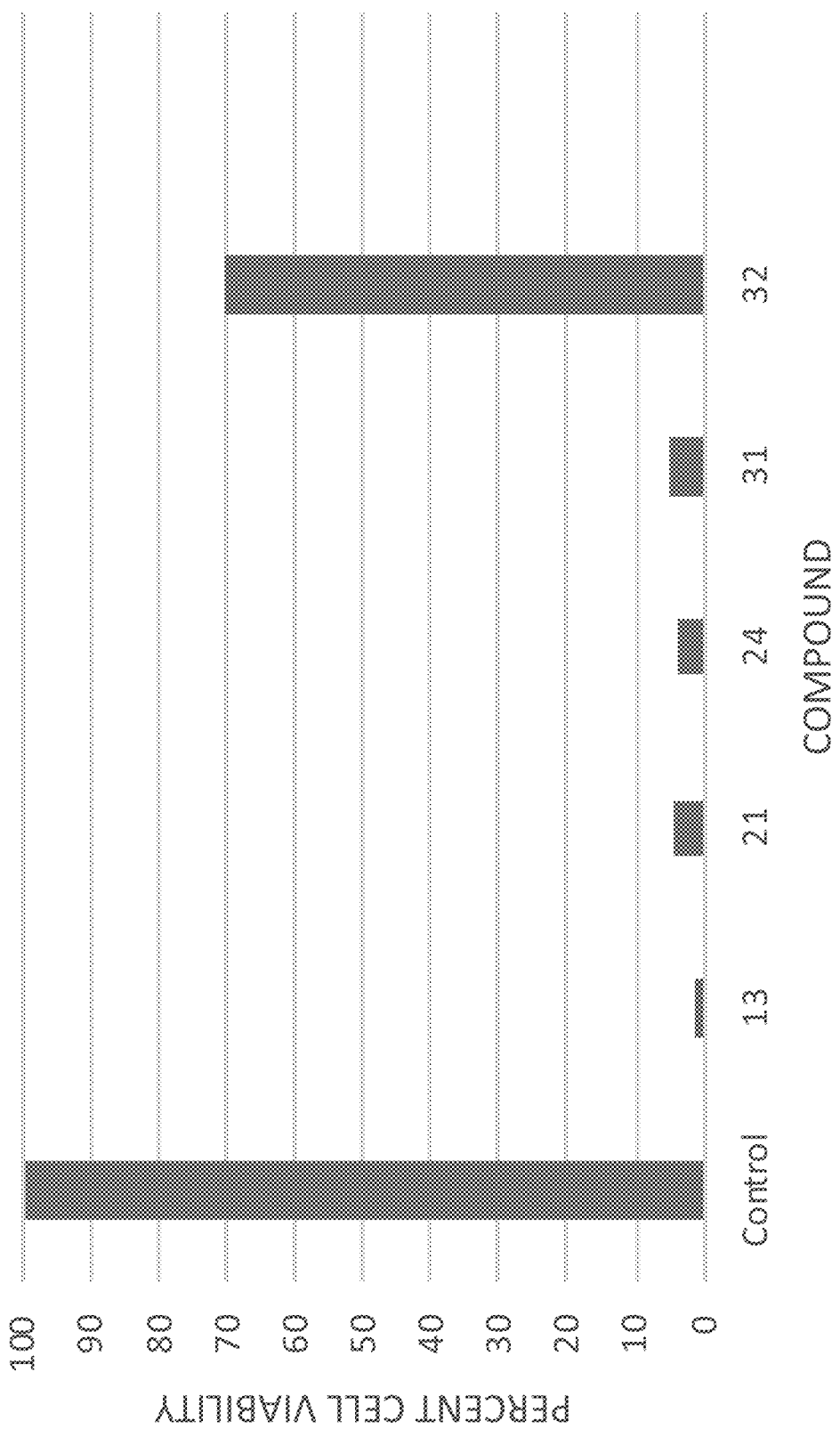
FIG. 6. Percent cell viability of normal breast cells (MCF10A) when treated with 1 mM selected compounds in DMSO.
Figure 7:
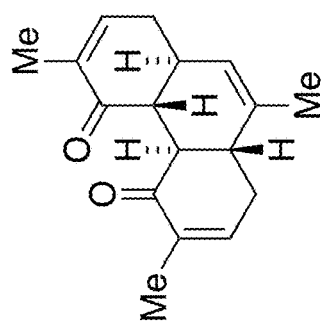
FIG. 7. Compound 18 and compound 24 were tested in cell viability assays against PC3 (prostate) and MDA-MB-231 (breast) cancer cell lines and found to possess promising activity. Shown below in the two tables are the cell viability data obtained at three different concentrations
Figure 7:
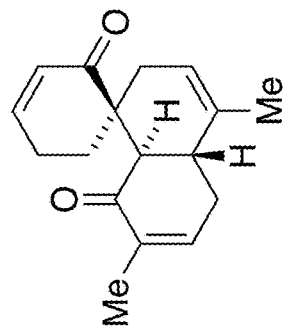

Access to the suite of compounds described above provided us with an opportunity to evaluate their possible biological activity. The presence of enone functionality within the initial products of the couple & close sequence is reminiscent of barboxolone methyl (37), an oleanolic acid-derived semi-synthetic triterpenoid that underwent a Phase 1 clinical trial for the treatment of solid tumors and lymphomas,[55-56] and to the quassinoid family of anti-neoplastic natural products as represented by quassin (38, FIG. 4).[57]

Given these structural similarities, we examined a selection of our scaffolds for cytotoxicity assays against a panel of five tumor cell lines and one non-tumorigenic cell line. As shown in Table 1, preliminary results show that these compounds exhibited potency against a variety of cancer cell lines at 1.0 mM: colon (HT29), prostate (PC-3), cervix (HeLa), breast (MDA-MB-231), and metastatic breast (MDA-MB-231-LM24).

TABLE 1

Preliminary evaluation of cytotoxicity of selected scaffolds at 1.0 mM in DMSO against a panel of cancer cell lines. HT29 (colon), PC-3 (prostate), HeLa (cervix), MDA-MB-231 (breast), MDA-MB-231-LM24 (metastatic breast) and MCF10A ("normal" breast) were used. DMSO was used as a negative control.

| Compound | Percent Cell Viability of Treated Cell Lines at 1.0 mM | | | | | |
|---|---|---|---|---|---|---|
| | HT29 | PC-3 | HeLa | MDA-MB-231 | MDA-MB-231-LM24 | MCF10A |
| 13 | 2 | 0 | 4 | 26 | 2 | 1 |
| 33 | 51 | 77 | 13 | 75 | 60 | ND |
| 14 | 1 | 72 | 46 | 69 | 67 | ND |
| 15 | 66 | 63 | 40 | 11 | 54 | ND |
| 19 | 1 | 1 | 0 | 0 | 0 | ND |
| 20 | 31 | 11 | 2 | 43 | 10 | ND |
| 21 | 0 | 0 | 0 | 0 | 0 | 4 |
| 36 | 64 | 77 | 41 | 53 | 55 | ND |
| 24 | 0 | 0 | 3 | 1 | 0 | 4 |
| 25 | 0 | 0 | 21 | 6 | 1 | ND |
| 28 | 0 | 1 | 0 | 2 | 16 | ND |
| 29 | 8 | 2 | 22 | 62 | 26 | ND |
| 31 | 0 | 0 | 2 | 26 | 3 | 5 |
| 32 | 1 | 1 | 0 | 25 | 0 | 70 |
| DMSO | 100 | 100 | 100 | 100 | 100 | 100 |

ND = not determined.

For example, the parent tricyclic compound 13 led to low percent cell viability in all five cell lines examined. As anticipated, the viability of each cell line was greatly increased for saturated analog 33, demonstrating the activity dependence on unsaturation. Further supporting this dependence, scaffold 15, which possesses methyl substitution at the β-position of both enones exhibited a much lower general potency against the cell lines. An examination of the tricyclic scaffolds containing quaternary centers showed α-methyl analog 19 to be one of the most potent compounds studied, demonstrating high activity across the panel. On the other hand, compound 20, containing the β-methyl stereocenter showed a general decrease in potency compared to 19 (although we note here that 19 and 20 have enantiomeric stereochemical configurations). The most active compound (i.e., 21) possessed the 4,4-gem-dimethyl motif that is a prevalent feature of numerous natural product families. Selective removal of the enone unsaturation of 21 to diketone 36 enabled a direct examination of the enone effect on activity. The evident increase in cell viability across all cell lines when treated with compound 36 further established the likely role of the enone for activity.

Compounds possessing structural variations away from the phenanthrene core also demonstrated preserved levels of potency. For instance, spirocyclic compound 24 exhibited activity across all cancer cell lines tested, while the ring-expanded analog 25 showed activity comparable to parent tricyclic species 13. Similarly, bicyclic compound 28, containing an α-quaternary center, showed general potency across the panel. In further accordance with the tricyclic analog data (c.f., 19 vs 20), bicyclic scaffold 29 with a quaternary center in the β-position, showed a marked decrease in activity compared to its α-substituted equivalent 28. Interestingly, both epoxide-containing compounds (i.e., 31 and 32) presented potency against all cell lines. Both compounds showed the weakest activity against the breast tumor line MDA-MB-231, but activity against the aggressive metastatic breast cancer cell line, MDA-MB-231-LM24. The lack of enone functionality within bis-epoxide 32 was especially noteworthy, given that reduction of the enones within 13 led to a loss of activity. The α-keto epoxide motif within bis-epoxide 32 does, however, bear some semblance to the pharmacophore of the natural product epoxomicin[58] and the FDA approved anti-cancer drug, carfilzomib.[59]

While many of the enone-containing compounds possessed cell killing activity against cancer cells, we were concerned that these compounds were most likely indiscriminate cytotoxic agents. This concern was borne out when we tested a selection of the most potent enones against the "normal" non-tumorigenic breast epithelial cell line, MCF10A. Compounds 13, 21, 24 and 31 were all highly active against this cell line, showing no selectivity for killing cancer cells over "normal" cells. On the other hand, bis-epoxide 32 was substantially less cytotoxic against the MCF10A cell line, with a cell viability of 70% at 1.0 mM. To follow-up on this last result, we determined the $IC_{50}$ value of bis-epoxide 32 to be 0.2 mM against MDA-MB-231-LM24 and 3.1 mM against MCF10A. This 15-times selectivity between cancer versus "normal" cell lines indicates that bis-epoxide 32 might represent a potentially useful scaffold for further modification and development, but more work will be required in the future to make this determination. The flexible nature of our developed strategy for accessing this type of structure means that such an exercise should be possible.

Application to the Formal Total Synthesis of 7,20-Diisocyanoadociane.

One long-term goal motivating our development of the couple & close strategy is to provide new approaches for the convergent assembly of stereochemically dense polycyclic natural products. Within this context, we were particularly inspired by the marine sponge-derived diterpene, (+)-7,20-diisocyanoadociane (39, Scheme 3a). First isolated in 1976 from a species within the Amphimedon family, and later from *Cymbastela hooperi* in 1996, this natural product contains ten contiguous stereogenic centers distributed amongst a tetracyclic backbone possessing two unusual tertiary isonitrile groups. Biological evaluation of 39 showed that it displays potent activity against the malaria parasite *Plasmodium falciparum* with a reported $IC_{50}$ value of 4.7 nM, while remaining inert against normal human cells.[60] This combination of promising biological activity and complex structure has made 39, and related isocyanoterpenes, popular targets for total synthesis.[61-62] The inaugural synthesis of 39, completed by Corey and Magriotis in 1987, served to fully establish the absolute and relative stereochemistry of the compound.[63] Their approach accessed tetracyclic intermediate 40 (Scheme 3a) in 26 steps through a strategy highlighting the strategic power and versatility of intramolecular Diels-Alder reactions. Late-stage dione 40 (now often referred to as the Corey dione) was converted to the natural product through a three-step sequence involving conversion of the ketones to the corresponding tertiary trifluoroacetates, which underwent non-stereoselective displacement with TMSCN in the presence of titanium tetrachloride to furnish 39 along with several isomeric isonitriles. Dione 40 has been the target for two subsequent formal syntheses by the Miyaoka[64] and Vanderwal groups[65] in 2011 and 2016, respectively. While Miyaoka and coworkers converged on 40 in 29 steps, Vanderwal and Roosen devised a clever strategy that delivered 40 in a reduced count of 21 steps. Two groups have provided routes to 7,20-diisocyanoadociane that install the isonitrile groups with high levels of diastereocontrol. The first of these routes, reported by Mander and Fairweather in 2006, established the requisite stereochemical relationships at C7 and C20 through creative application of the Curtius rearrangement to complete a 42-step formal synthesis of racemic 39.[66] The second route, reported by Shenvi and coworkers in 2016,[67] introduced the isonitriles in a controlled manner through application of their previously reported stereoinvertive displacement of tertiary trifluoroacetates.[68] This elegant strategy afforded (+)-diisocyanoadociane (39) in only 17 steps and stimulated further biological studies of this general class of isonitrile-containing compounds.

Collectively, the past endeavors targeting the unique architecture of 7,20-diisocyanoadociane (39) serve to illustrate how natural product synthesis can stimulate and test novel chemical methodologies and strategies. We considered 7,20-diisocyanoadociane (39) to be an excellent target to further explore the potential of our couple & close strategy. The all trans-perhydropyrene carbocyclic core of 39 maps suggestively onto the all trans-phenanthrene structures that are readily accessed using our methodology (see FIG. 2). We desired to take advantage of the pseudo $C_2$-symmetry embedded within 39, which led to us targeting the Corey dione 40 as the formal endpoint of our synthesis (Scheme 3a). We reasoned that by utilizing symmetry we could significantly reduce the step count required to access this late-stage intermediate. Our retrosynthetic analysis thus targeted disconnection of 40 along the central axis defined by the C9-C10, C12-C13 and C2-C3 bonds highlighted in red. Informed by the above considerations, substructure analysis of dione 40 led naturally to tricyclic dienone 41 as the initial subgoal of our planned synthesis. This species would be accessed in a highly convergent manner from the two monocyclic enones 42 and 3 by oxidative cross-coupling and ring-closing metathesis.

Scheme 3. a) The final stages of the Corey and Magriotis synthesis of (+)-7,20-diisocyanoadociane, 39, from tetracyclic diketone 40; Our strategy, targeting the Corey intermediate 40 with the implementation of the developed strategy; b) Completed synthesis of the Corey dione 40.

a.

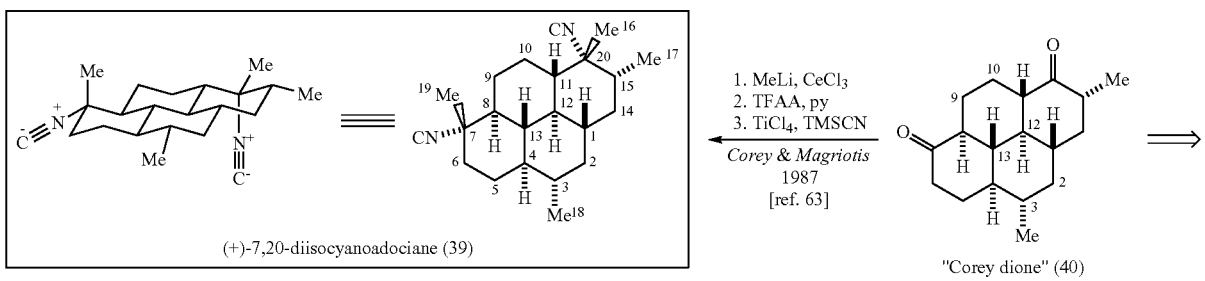

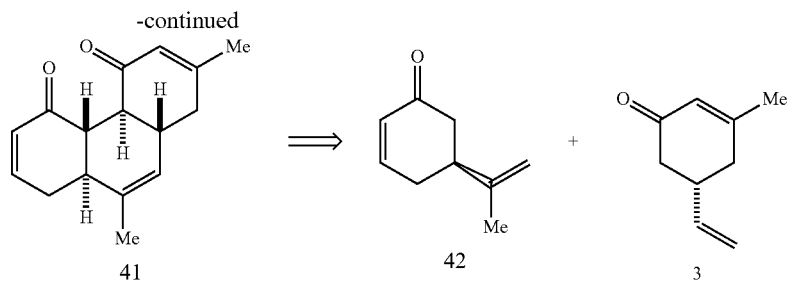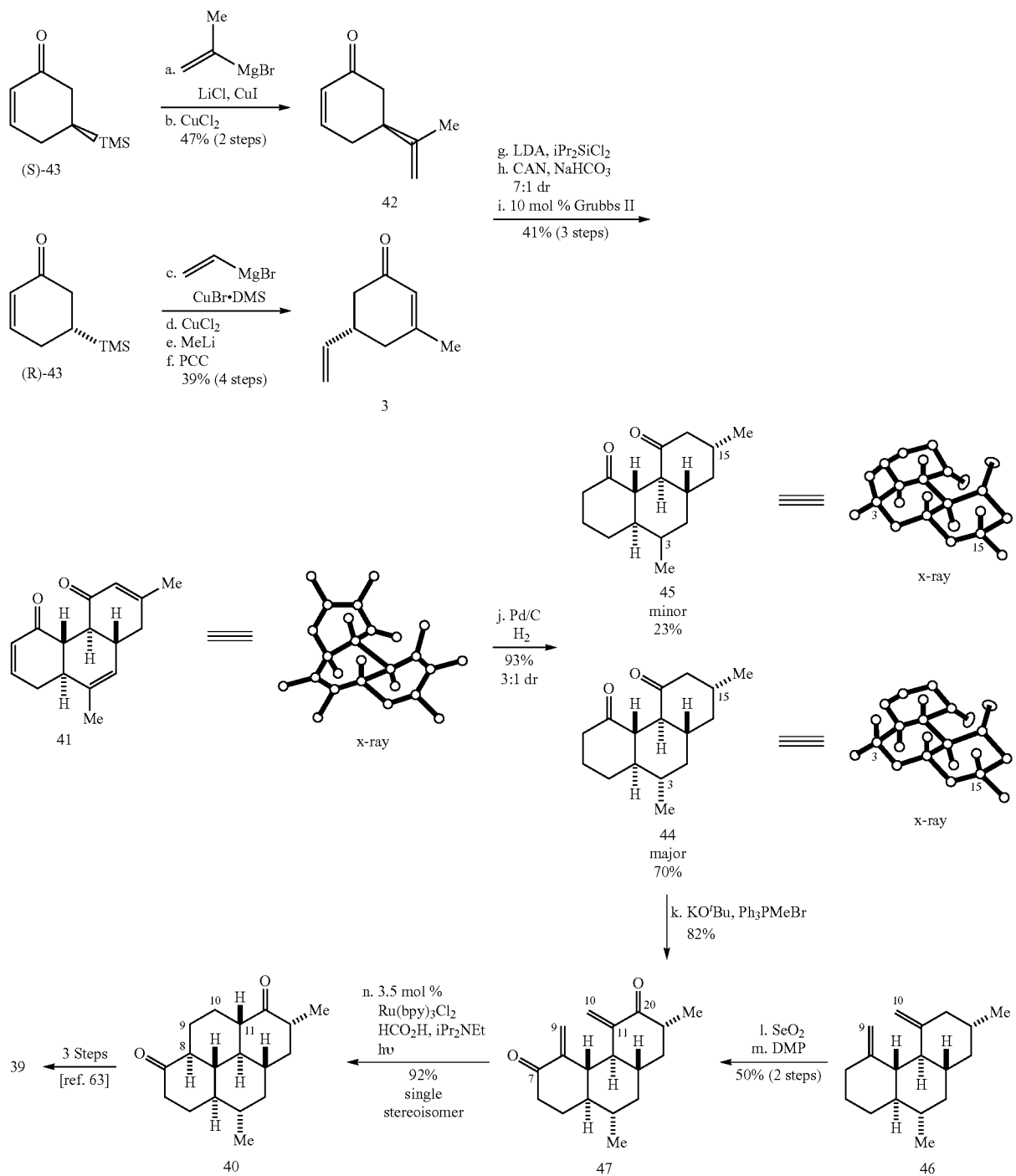

Reagents and Conditions for Scheme 3.

a) isopropenylmagnesium bromide, LiCl, CuI, TMSCl, 0° C., 65%; b) CuCl$_2$, DMF, 55° C., 72%; c) vinylmagnesium bromide, CuBr.DMS, HMPA, TMSCl, THF, −78° C., 78%; d) CuCl$_2$, DMF, 55° C., 85%; e) MeLi, THF, −78° C.; f) PCC, DCM, 59% over two steps; g) LDA, iPr$_2$SiCl$_2$, THF, −78° C.; h) CAN, NaHCO$_3$, ACN/EtCN/DMSO, −30° C., 7:1 dr; i) Grubbs II, DCM, 40° C., 41% over three steps; j) Pd/C, H$_2$, MeOH, 3:1 dr, 93%; k) KO$^t$Bu, Ph$_3$PMeBr, benzene, 80° C., 82%; l) SeO$_2$, DCM, EtOH, 78° C.; m) DMP, DCM, 50% over two steps; n) Ru(bpy)$_3$Cl$_2$.H$_2$O, HCO$_2$H, iPr$_2$NEt, ACN, hν, 92%.

Our synthesis commenced with preparation of the desired enone monomers, 42 and 3, from enantioenriched β-TMS enones (S)-43 and (R)-43, respectively (Scheme 3b). These highly versatile chiral starting materials could be prepared in 2-steps from (E)-3-(trimethylsilyl)prop-2-en-1-ol on a 10-gram scale using the organocatalytic Robinson annulation protocol devised by Jørgensen and coworkers.[42] Conjugate addition of isopropenylmagnesium bromide to (S)-43 proceeded with complete facial selectivity to deliver the requisite enone fragment 42 following oxidative elimination of the TMS substituent with CuCl$_2$ (47% over two steps).[43,45] Synthesis of enone fragment 3 involved a similar sequence of events beginning with the diastereocontrolled conjugate addition of vinylmagnesium bromide to (R)-43 and subsequent exposure of the thus formed ketone to CuCl$_2$. 1,2-Addition of methyllithium and oxidative transposition using PCC installed the necessary 3-methylsubstituent, thereby producing the desired product 3 in 39% over the four steps.

Convergent and stereoselective assembly of tricyclic dienone 41 from enones 42 and 3 was then established through the three-step couple & close strategy. Pleasingly, this initial subtarget for our planned synthesis was formed in 41% over the three steps, with the all-trans stereochemistry of the major isomer (7:1 dr) confirmed by X-ray structural analysis.

Global hydrogenation of all three alkenes within 41 using Pd/C and hydrogen proceeded in 93% yield to deliver a 3:1 mixture of stereoisomers that were not separable using standard silica gel flash chromatography. Fortunately, effective separation was achieved using preparative HPLC, affording pure crystalline samples of the products. X-ray structures were solved for both products, revealing that the major product (i.e., 44) possessed the correct bis-equatorial configuration for the two newly installed methyl stereocenters. The minor isomer (i.e., 45) possessed the correct stereochemistry at C15, but the incorrect axial configuration for the C3 methyl appendage. Attempts to improve the diastereoselectivity for this reduction process did not lead to any enhancements. At this juncture we had established three of the four rings, and six of the eight stereocenters needed to complete the synthesis of Corey dione 40. The major challenge remaining was installation of the two-carbon bridge (i.e., C8-C9-C10-C11) required to forge the final ring. A number of unsuccessful routes were investigated, such as converting diketone 44 into the corresponding bis-enol triflate in the hopes of conducting a double metal-catalyzed coupling with a suitable two-carbon linchpin. The close proximity of the two carbonyl groups within 44 made many attempted transformations challenging, due to either a lack of reactivity or a predilection for compounds to undergo unwanted rearrangements. Somewhat surprisingly, however, we were pleased to find that a double methylenation of 44 could be realized using an excess quantity of Wittig reagent in refluxing benzene. Thus, bis-alkene 46 was formed in 82% yield from 44, with the two newly installed exocyclic carbon atoms representing C9 and C10 within the ultimate target (i.e., 40). A selenium dioxide-mediated double allylic oxidation to the diol (not shown), followed by oxidation with Dess-Martin periodinane afforded bis-enone 47 in 50% over two steps from 46.

At this time, we hoped to benefit from the "enforced propinquity"[69] of C9 and C10 in order to forge the remaining s-bond within Corey dione 40. Qualitative inspection of models of 47 indicated to us that any radical character on C9 and/or C10 should lead to rapid bond formation between the two carbon atoms. In order to achieve this desired outcome we considered the use of single-electron reductants such as samarium diodide,[70] but we were especially keen to utilize the photocatalytic reductive g-coupling of enones that was reported by Yoon and coworkers in 2011.[71] In this publication a variety of bis-enones were shown to undergo effective reductive coupling upon irradiation with a simple fluorescent bulb in the presence of catalytic Ru(bpy)$_3$Cl$_2$, formic acid, and a tertiary amine. The mild reaction conditions, ease of experimental setup, and contemporary nature of photocatalysis in organic chemistry made it particularly attractive to explore in the context of natural product synthesis.[72-74] As hoped for, when bis-enone 47 was exposed to the conditions reported by Yoon and coworkers, the desired product (i.e., 40) was formed as a single stereoisomer in 92% yield. Due to the rigid nature of the all-trans backbone of 47, generation of the new C8 and C11 stereocenters within 40 by axial protonation is most likely favored kinetically due to high torsional strain generated along the corresponding equatorial trajectory; a situation reminiscent of the reactions of conformationally-locked cyclohexanones and trans-decalones.[75-76] In any event, as past synthetic efforts have shown, the all trans-configured isomer of the adociane ring system is favored thermodynamically.[63-65] Thus, we completed the synthesis of Corey dione 40 in 12-steps from (R)-43 with a total yield of 4.2% (or 2.4% from (E)-3-(trimethylsilyl)prop-2-en-1-ol, a commercially available starting material), thereby establishing a 17-step formal synthesis of (+)-7,20-diisocyanoadociane.

CONCLUSIONS

We have developed a strategy employing a diastereoselective oxidative coupling/ring-closing metathesis sequence to rapidly construct fused carbocyclic compounds from assorted ketone building blocks. The modular approach is tolerant of a wide variety of substitution patterns, as well as structural modifications of the carbocyclic scaffold produced. We have demonstrated successful selective manipulations of these compounds, and have efficiently implemented the strategy in the convergent formal synthesis of the antimalarial diterpene, (+)-7,20-diisocyanoadociane. Biological studies of the prepared compounds have shown promising anticancer activities, and efforts to further probe the mechanism of this action are underway.

REFERENCES

1. Corey, E. J.; Cheng, X.-M., The Logic of Chemical Synthesis. John Wiley & Sons: New York, 1989.
2. Walters, W. P.; Green, J.; Weiss, J. R.; Murcko, M. A., J. Med. Chem. 2011, 54, 6405-6416.
3. Lovering, F.; Bikker, J.; Humblet, C., J. Med. Chem. 2009, 52, 6752-6756.
4. Schreiber, S. L., Science 2000, 287, 1964-1969.

5. Huigens Iii, R. W.; Morrison, K. C.; Hicklin, R. W.; Flood Jr, T. A.; Richter, M. F.; Hergenrother, P. J., Nat. Chem. 2013, 5, 195.
6. Kou, K. G. M.; Kulyk, S.; Marth, C. J.; Lee, J. C.; Doering, N. A.; Li, B. X.; Gallego, G. M.; Lebold, T. P.; Sarpong, R., J. Am. Chem. Soc. 2017, 139, 13882-13896.
7. Kim, W. S.; Du, K.; Eastman, A.; Hughes, R. P.; Micalizio, G. C., Nat. Chem. 2017, 10, 70.
8. Paciaroni, N. G.; Ratnayake, R.; Matthews, J. H.; Norwood, V. M.; Arnold, A. C.; Dang, L. H.; Luesch, H.; Huigens, R. W., Chem. Eur. J. 2017, 23, 4327-4335.
9. Scott, S. K.; Grenning, A. J., Angew. Chem. Int. Ed. 2017, 56, 8125-8129.
10. Wildermuth, R.; Speck, K.; Haut, F.-L.; Mayer, P.; Karge, B.; Brönstrup, M.; Magauer, T., Nat. Commun. 2017, 8, 2083.
11. Guo, F. H.; Clift, M. D.; Thomson, R. J., Eur. J. Org. Chem. 2012, 4881-4896.
12. Csaky, A. G.; Plumet, J., Chem. Soc. Rev. 2001, 30, 313-320.
13. Baran, P. S.; Guerrero, C. A.; Ambhaikar, N. B.; Hafensteiner, B. D., Angew. Chem. Int. Ed. 2005, 44, 606-609.
14. Baran, P. S.; Hafensteiner, B. D.; Ambhaikar, N. B.; Guerrero, C. A.; Gallagher, J. D., J. Am. Chem. Soc. 2006, 128, 8678-8693.
15. DeMartino, M. P.; Chen, K.; Baran, P. S., J. Am. Chem. Soc. 2008, 130, 11546-11560.
16. Martin, C. L.; Overman, L. E.; Rohde, J. M., J. Am. Chem. Soc. 2008, 130, 7568-7569.
17. Herzon, S. B.; Lu, L.; Woo, C. M.; Gholap, S. L., J. Am. Chem. Soc. 2011, 133, 7260-7263.
18. Ekebergh, A.; Karlsson, I.; Mete, R.; Pan, Y.; Borje, A.; Martensson, J., Org. Lett. 2011, 13, 4458-4461.
19. You, L.; Liang, X.-T.; Xu, L.-M.; Wang, Y.-F.; Zhang, J.-J.; Su, Q.; Li, Y.-H.; Zhang, B.; Yang, S.-L.; Chen, J.-H.; Yang, Z., J. Am. Chem. Soc. 2015, 137, 10120-10123.
20. Ghosh, S.; Chaudhuri, S.; Bisai, A., Org. Lett. 2015, 17, 1373-1376.
21. Quesnelle, C. A.; Gill, P.; Kim, S.-H.; Chen, L.; Zhao, Y.; Fink, B. E.; Saulnier, M.; Frennesson, D.; DeMartino, M. P.; Baran, P. S.; Gavai, A. V., Synlett 2016, 27, 2254-2258.
22. Ivanoff, D.; Spasoff, A., Bull. Soc. Chim. Fr. 1935, 2, 76-78.
23. Rathke, M. W.; Lindert, A., J. Am. Chem. Soc. 1971, 93, 4605-4606.
24. Ito, Y.; Konoike, T.; Saegusa, T., J. Am. Chem. Soc. 1975, 97, 649-651.
25. Ito, Y.; Konoike, T.; Harada, T.; Saegusa, T., J. Am. Chem. Soc. 1977, 99, 1487-1493.
26. Baran, P. S.; DeMartino, M. P., Angew. Chem. Int. Ed. 2006, 45, 7083-7086.
27. Casey, B. M.; Flowers, R. A., J. Am. Chem. Soc. 2011, 133, 11492-11495.
28. Jang, H. Y.; Hong, J. B.; MacMillan, D. W. C., J. Am. Chem. Soc. 2007, 129, 7004-7005.
29. Beeson, T. D.; Mastracchio, A.; Hong, J. B.; Ashton, K.; MacMillan, D. W. C., Science 2007, 316, 582-585.
30. Graham, T. H.; Jones, C. M.; Jui, N. T.; MacMillan, D. W. C., J. Am. Chem. Soc. 2008, 130, 16494-16495.
31. Kim, H.; MacMillan, D. W. C., J. Am. Chem. Soc. 2008, 130, 398-399.
32. Do, H. Q.; Hung, T. V.; Daugulis, O., Organometallics 2012, 31, 7816-7818.
33. Moeller, K. D., Synlett 2009, 1208-1218.
34. Schmittel, M.; Burghart, A.; Malisch, W.; Reising, J.; Sollner, R., J. Org. Chem. 1998, 63, 396-400.
35. Clift, M. D.; Taylor, C. N.; Thomson, R. J., Org. Lett. 2007, 9, 4667-4669.
36. Avetta, C. T.; Konkol, L. C.; Taylor, C. N.; Dugan, K. C.; Stern, C. L.; Thomson, R. J., Org. Lett. 2008, 10, 5621-5624.
37. Konkol, L. C.; Jones, B. T.; Thomson, R. J., Org. Lett. 2009, 11, 5550-5553.
38. Clift, M. D.; Thomson, R. J., J. Am. Chem. Soc. 2009, 131, 14579-14583.
39. Konkol, L. C.; Guo, F. H.; Sarjeant, A. A.; Thomson, R. J., Angew. Chem. Int. Ed. 2011, 50, 9931-9934.
40. Jones, B. T.; Avetta, C. T.; Thomson, R. J., Chem. Sci. 2014, 5, 1794-1798.
41. Vega, M. M.; Crain, D. M.; Konkol, L. C.; Thomson, R. J., Tetrahedron Lett. 2015, 56, 3228-3230.
42. Bolze, P.; Dickmeiss, G.; Jørgensen, K. A., Org. Lett. 2008, 10, 3753-3756.
43. Sarakinos, G.; Corey, E. J., Org. Lett. 1999, 1, 811-814.
44. Asaoka, M.; Sonoda, S.; Fujii, N.; Takei, H., Tetrahedron 1990, 46, 1541-1552.
45. Asaoka, M.; Shima, K.; Takei, H., ChemComm 1988, 430-431.
46. Torosyan, S. A.; Gimalova, F. A.; Valeev, R. F.; Miftakhov, M. S., Rus. J. Org. Chem. 2011, 47, 682.
47. Furrow, M. E.; Myers, A. G., J. Am. Chem. Soc. 2004, 126, 5436-5445.
48. Asaba, T.; Katoh, Y.; Urabe, D.; Inoue, M., Angew. Chem. Int. Ed. 2015, 54, 14457-14461.
49. Barros, M. T.; Maycock, C. D.; Ventura, M. R., J. Org. Chem. 1997, 62, 3984-3988.
50. Yamamoto, E.; Gokuden, D.; Nagai, A.; Kamachi, T.; Yoshizawa, K.; Hamasaki, A.; Ishida, T.; Tokunaga, M., Org. Lett. 2012, 14, 6178-6181.
51. Scholl, M.; Ding, S.; Lee, C. W.; Grubbs, R. H., Org. Lett. 1999, 1, 953-956.
52. Frazier, R. H.; Harlow, R. L., J. Org. Chem. 1980, 45, 5408-5411.
53. Hong, S. H.; Day, M. W.; Grubbs, R. H., J. Am. Chem. Soc. 2004, 126, 7414-7415.
54. Hong, S. H.; Sanders, D. P.; Lee, C. W.; Grubbs, R. H., J. Am. Chem. Soc. 2005, 127, 17160-17161.
55. Hong, D. S.; Kurzrock, R.; Supko, J. G.; He, X.; Naing, A.; Wheler, J.; Lawrence, D.; Eder, J. P.; Meyer, C. J.; Ferguson, D. A.; Mier, J.; Konopleva, M.; Konoplev, S.; Andreeff, M.; Kufe, D.; Lazarus, H.; Shapiro, G. I.; Dezube, B. J., Clin. Cancer Res. 2012, 18, 3396-3406.
56. Sporn, M. B.; Liby, K.; Yore, M. M.; Suh, N.; Albini, A.; Honda, T.; Sundararajan, C.; Gribble, G. W., Drug. Dev. Res. 2007, 68, 174-182.
57. Guo, Z.; Vangapandu, S.; W Sindelar, R.; Walker, L.; D Sindelar, R., Curr. Med. Chem. 2005, 12, 173-190.
58. Meng, L.; Mohan, R.; Kwok, B. H. B.; Elofsson, M.; Sin, N.; Crews, C. M., Proc. Natl. Acad. Sci. USA 1999, 96, 10403-10408.
59. Moreau, P., Expert Rev. Hematol. 2014, 7, 265-290.
60. Wright, A. D.; Konig, G. M.; Angerhofer, C. K.; Greenidge, P.; Linden, A.; Desqueyroux-Faundez, R., J. Nat. Prod. 1996, 59, 710-716.
61. Schnermann, M. J.; Shenvi, R. A., Nat. Prod. Rep. 2015, 32, 543-577.
62. Daub, M. E.; Roosen, P. C.; Vanderwal, C. D., J. Org. Chem. 2017, 82, 4533-4541.
63. Corey, E. J.; Magriotis, P. A., J. Am. Chem. Soc. 1987, 109, 287-289.
64. Miyaoka, H.; Okubo, Y.; Muroi, M.; Mitome, H.; Kawashima, E., Chem. Lett. 2011, 40, 246-247.

65. Roosen, P. C.; Vanderwal, C. D., Angew. Chem. Int. Ed. 2016, 55, 7180-7183.
66. Fairweather, K. A.; Mander, L. N., Org. Lett. 2006, 8, 3395-3398.
67. Lu, H. H.; Pronin, S. V.; Antonova-Koch, Y.; Meister, S.; Winzeler, E. A.; Shenvi, R. A., J. Am. Chem. Soc. 2016, 138, 7268-7271.
68. Pronin, S. V.; Reiher, C. A.; Shenvi, R. A., Nature 2013, 501, 195-199.
69. Woodward, R. B., Pure. Appl. Chem. 1968, 17, 519-547.
70. Nicolaou, K. C.; Ellery, S. P.; Chen, J. S., Angew. Chem. Int. Ed. 2009, 48, 7140-7165.
71. Du, J. N.; Espelt, L. R.; Guzei, I. A.; Yoon, T. P., Chem. Sci. 2011, 2, 2115-2119.
72. Narayanam, J. M. R.; Stephenson, C. R. J., Chem. Soc. Rev. 2011, 40, 102-113.
73. Corrigan, N.; Shanmugam, S.; Xu, J.; Boyer, C., Chem. Soc. Rev. 2016, 45, 6165-6212.
74. Shaw, M. H.; Twilton, J.; MacMillan, D. W. C., J. Org. Chem. 2016, 81, 6898-6926.
75. Corey, E. J.; Sneen, R. A., J. Am. Chem. Soc. 1956, 78, 6269-6278.
76. Matthews, R. S.; Girgenti, S. J.; Folkers, E. A., Chem-Comm. 1970, 708-709.

Example 2

Title—Synthesis and Stereoselective Assembly of Polycyclic Molecules and Biological Testing Reference is made to the Supporting Information for Emily E. Robinson and Regan J. Thomson, "A Strategy for the Convergent and Stereoselective Assembly of Polycyclic Molecules," J. Am. Chem. Soc. 2018, 140, 1956-1965, published Jan. 8, 2018, and Correction to "A Strategy for the Convergent and Stereoselective Assembly of Polycyclic Molecules," J. Am. Chem. Soc. 2018, 140, 7043-7043, published May 21, 2018, the contents of which are incorporated herein by reference in their entireties.

1. General Information.

All reactions were carried out under a nitrogen atmosphere in flame-dried glassware with magnetic stirring unless otherwise stated. Methanol, THF, ether and DCM were purified by passage through a bed of activated alumina.[1] Reagents were purified prior to use unless otherwise stated following the guidelines of Armarego and Chai.[2] Purification of reaction products was carried out by flash chromatography using SiliCycle silica gel F60, 40-63 μm (230-400 mesh). Analytical thin layer chromatography was performed on EM Reagent 0.25 mm silica gel 60-F plates. Visualization was accomplished with UV light and p-anisaldehyde stain. Germanium ATR infrared spectra were recorded using a Bruker Tensor 37. $^1$H-NMR spectra were recorded on a Varian Inova 500 (500 MHz), Agilent DD2 (500 MHz), Agilent DD MR-400 (400 MHz), or Bruker Advance III 500 (500 MHz) spectrometer and are reported in ppm using solvent as an internal standard (CDCl$_3$ at 7.26 ppm). Data are reported as (app=apparent, obs=obscured, s=singlet, d=doublet, t=triplet, q=quartet, p=pentet, h=hextet, sep=septet, o=octet, m=multiplet, b=broad; integration; coupling constant(s) in Hz. $^{13}$C-NMR spectra were recorded on a Bruker Advance III 500 spectrometer equipped with DCH CryoProbe, and are reported in ppm using solvent as an internal standard (CDCl$_3$ at 77.16 ppm, except where noted). Mass spectra data were obtained on an Agilent 6210 Time-of-Flight LC/MS. All optical rotation measurements were obtained on a Rudolph Research Analytical Autopol IV, Serial #82239. X-ray data were collected on the Kappa Apex 2 diffractometer.

2. Starting Material Experimental Procedures and Characterization Data

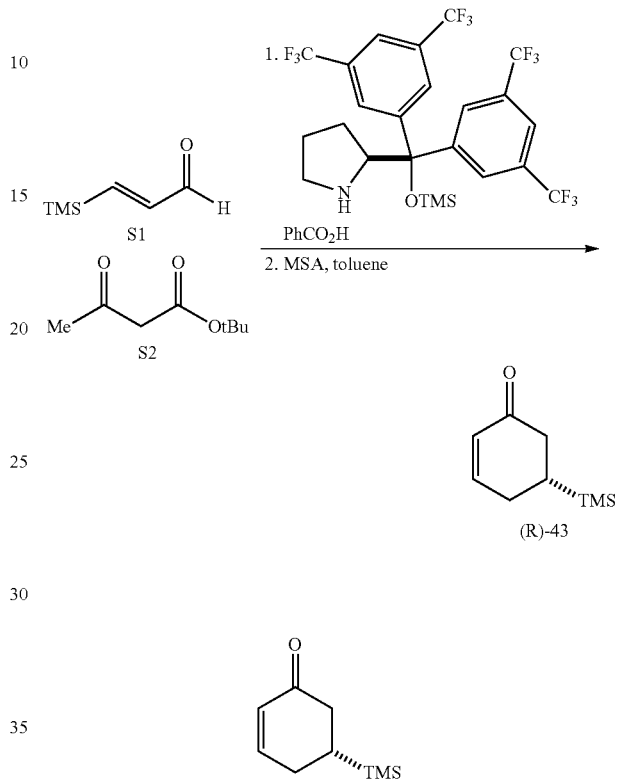

Scheme S1. Synthesis of enantioenriched silane intermediate (R)-43.

Compound (R)-43. The common enantioenriched silane intermediate was prepared as reported by Jørgensen and coworkers.[3] The proline-derived catalyst (S)-α,α-Bis[3,5-bis(trifluoromethyl)phenyl]-2-pyrrolidinemethanol trimethylsilyl ether (1.74 g, 2.92 mmol, 10 mol %), PhCO$_2$H (0.360 g, 2.92 mmol, 10 mol %), and toluene (10 mL) were added to a flame-dried 250 mL round-bottom flask. S1 (3.75 g, 29.2 mmol, 1.0 equiv.) in toluene (4 mL) was added via cannula (1 mL toluene rinse), followed by S2 (7.14 mL, 43.8 mmol, 1.5 equiv.). The yellow reaction was allowed to stir at room temperature for 20 hours, after which toluene (97 mL) and methanesulfonic acid (0.664 mL, 10.2 mmol, 35 mol %) were added and the mixture heated to 90° C. for 40 minutes. The red-orange mixture was cooled to room temperature, diluted with water, and extracted with ether. The combined organic layers were dried over MgSO$_4$ and the solvent evaporated under reduced pressure. The crude orange oil was purified by flash chromatography on silica gel using a 5% ether/pentane to 20% ether pentane gradient, yielding a yellow oil (3.40 g, 20.0 mmol, 68%). This procedure was scalable to 12.5 g S1 to provide a 59% yield. $^1$H NMR (499 MHz, Chloroform-d) δ 7.03 (ddd, J=10.1, 5.6, 2.4 Hz, 1H), 6.00 (ddt, J=10.1, 2.6, 1.1 Hz, 1H), 2.43 (ddt, J=16.5, 3.9, 1.3 Hz, 1H), 2.32 (dddt, J=19.0, 5.8, 4.7, 1.3 Hz, 1H), 2.27-2.13 (m, 2H), 1.47-1.40 (m, 1H), 0.03 (s, 9H); $^{13}$C NMR (126 MHz, CDCl$_3$) δ 200.4, 151.7, 129.5, 38.7, 26.9, 23.3, −3.6. The ee was determined by HPLC to be 99%, as reported in the literature. All spectroscopic data for this compound agrees with previously reported values.[3]

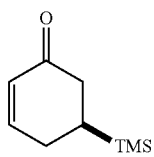 [SMILES: C[Si](C)(C)[C@H]1CC=CC(=O)C1]

5

Compound (S)-43. This compound was prepared as described for (R)-43 above, according to Jørgensen and coworkers, using the (R)-enantiomer of the catalyst. All spectroscopic data for this compound agrees with previously reported values.[3]

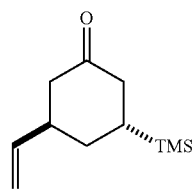

Compound (R)-S3.[4]

Freshly prepared and titrated vinyl Grignard (0.79 M, 16.5 mL, 13.0 mmol, 2.0 equiv.) and THF (38 mL) were added to a flame-dried 100 mL round-bottom flask. The mixture was cooled to −78° C., and CuBr.DMS (0.27 g, 1.3 mmol, 20 mol %) and HMPA (2.3 mL, 13.0 mmol, 2.0 equiv.) were added. After stirring at this temperature for 1 hour, (R)-43 (1.1 g, 6.5 mmol, 1.0 equiv.) in THF (1 mL) and TMS-Cl (2.5 mL, 19.5 mmol, 3.0 equiv.) was added via cannula dropwise over 10 minutes (0.5 mL THF rinse). After 40 minutes, the reaction was warmed to room temperature. Upon observed consumption of starting material (~2 hours) the black reaction was quenched with 1 M HCl, allowing the mixture to stir for 10 minutes, after which it was extracted with ether. The combined organic layers were washed with brine, dried over MgSO$_4$, and the solvent evaporated under reduced pressure. The crude material was purified by flash chromatography using silica gel with a 5% ether/pentane to 10% ether/pentane gradient, yielding a yellow oil (1.0 g, 5.1 mmol, 78%): [α]$_D$=+90.3 (c 0.088, CHCl$_3$); IR (Germanium ATR): 2954, 1710, 1249, 838 cm$^{-1}$; $^1$H NMR (500 MHz, Chloroform-d) δ 5.78 (ddd, J=17.4, 10.7, 5.5 Hz, 1H), 5.10 (dt, J=10.7, 1.5 Hz, 1H), 5.05 (dt, J=17.4, 1.5 Hz, 1H), 2.99 (dtt, J=7.7, 3.7, 1.8 Hz, 1H), 2.57-2.42 (m, 2H), 2.28 (ddt, J=14.3, 3.7, 1.8 Hz, 1H), 2.10 (td, J=14.3, 13.3, 0.9 Hz, 1H), 1.87-1.68 (m, 2H), 1.29 (ddt, J=13.3, 12.1, 4.0 Hz, 1H), −0.00 (s, 9H); $^{13}$C NMR (126 MHz, CDCl$_3$) δ 212.2, 140.5, 115.8, 45.0, 42.3, 41.0, 30.7, 21.7, −3.5; HRMS (ESI): Exact mass calc'd for C$_{11}$H$_{21}$OSi [M+H]$^+$, 197.1362. Found Scheme S2. Elaboration of common enantioenriced silane (R)-43 into varying substrates for the developed methodology

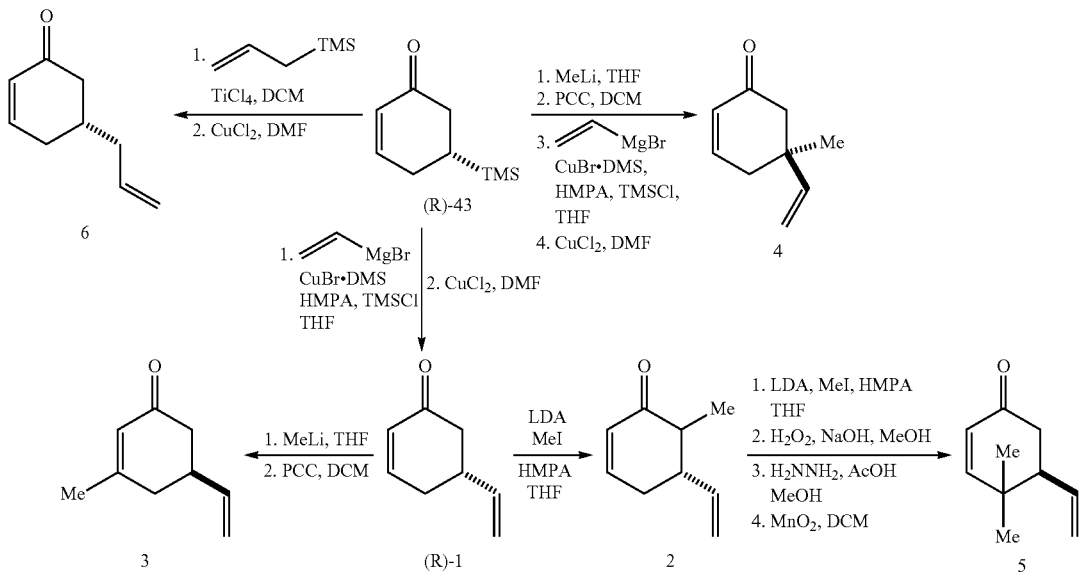

Scheme S3. Synthesis of compound (R)-1.

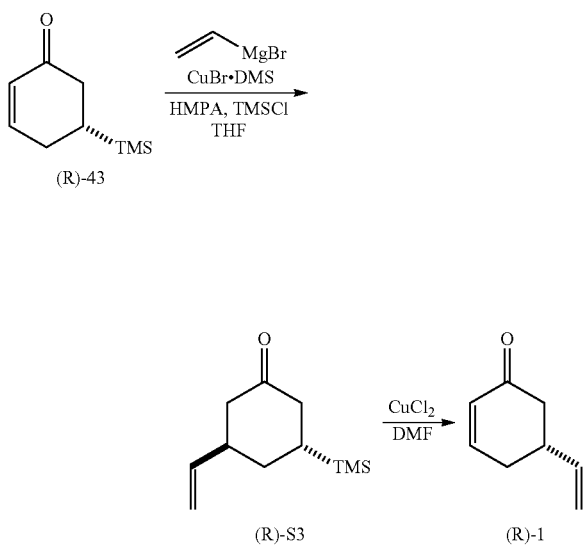

197.1355. All spectroscopic data for this compound agrees with previously reported values.[4]

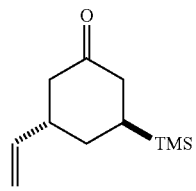

Compound (S)-S3.

This compound was prepared using the same procedure as for the preparation of (R)—S3 detailed above. (S)-43 (3.05 g, 18.1 mmol) was converted to (S)—S3 (1.93 g, 9.83 mmol, 55% yield). All NMR, IR, and HRMS data is identical to (R)—S3. $[\alpha]_D$=−83.5 (c 0.62, CHCl$_3$).

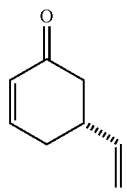

Compound (R)-1.

Copper-mediated elimination of the silane was achieved with conditions reported by Corey and coworkers.[5] CuCl$_2$ (2.1 g, 15.3 mmol, 3.0 equiv.) was added to a flame-dried 100 mL round-bottom flask outfitted with a reflux condenser. (R)—S3 (1.0 g, 5.0 mmol, 1.0 equiv.) in DMF (35 mL, with an additional 3 mL rinse) was added via cannula and the reaction was heated to 55° C. for 2 hours. The green reaction was cooled to room temperature, diluted with water, and extracted with pentane twice and 5% ether/pentane once. The combined organic layers were dried over MgSO$_4$ and the solvent removed under reduced pressure carefully due to the volatility of the product. The crude material was purified by flash chromatography with silica gel using 20% ether/pentane, yielding a yellow oil (522 mg, 4.3 mmol, 85%): $[\alpha]_D$=−47.6 (c 0.32, CHCl$_3$); IR (Germanium ATR): 3081, 2886, 1677, 1642, 1388, 918 cm$^{-1}$; $^1$H NMR (500 MHz, Chloroform-d) δ 6.97 (ddd, J=10.1, 5.5, 2.8 Hz, 1H), 6.13-5.97 (m, 1H), 5.83 (ddd, J=17.0, 10.4, 6.4 Hz, 1H), 5.15-4.98 (m, 2H), 2.81 (dddd, J=15.0, 10.3, 7.4, 4.6 Hz, 1H), 2.57 (dd, J=16.3, 4.1 Hz, 1H), 2.54-2.46 (m, 1H), 2.31 (dd, J=16.2, 12.3 Hz, 1H), 2.24 (ddt, J=18.7, 9.9, 2.7 Hz, 1H); $^{13}$C NMR (126 MHz, CDCl$_3$) δ 199.2, 149.3, 140.3, 130.0, 114.8, 43.6, 38.8, 31.8; HRMS (ESI): Exact mass calc'd for C$_8$H$_{11}$O [M+H]$^+$, 123.0810. Found 123.0801. The ee was determined to be 99% by HPLC on a Chiralpak-As-H column running 2% iPrOH in hexanes with a flow rate of 1.0 mL/min. All spectroscopic data for this compound agrees with previously reported values.[4]

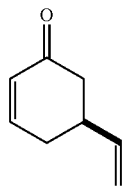

Compound (S)-1.

This compound was prepared using the same procedure as for the preparation of (R)-1. (S)—S3 (1.9 g, 9.7 mmol) was converted to (S)-1 (541.7 mg, 4.43 mmol, 46%). All NMR, IR, and HRMS data is identical to (R)-1. $[\alpha]_D$=+41.4 (c 0.38, CHCl$_3$).

Scheme S4. Synthesis of compound 2.

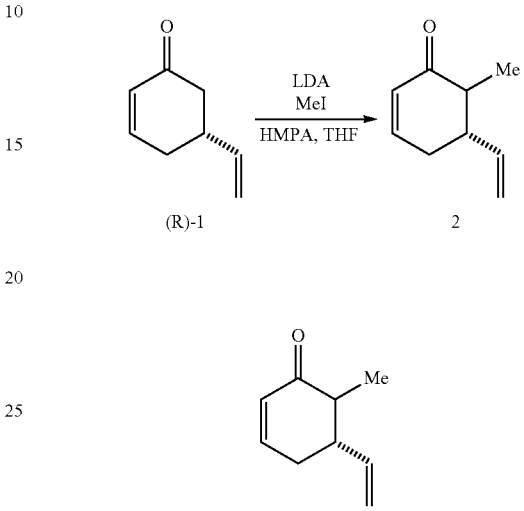

Compound 2.

A solution of LDA was prepared by adding diisopropylamine (0.169 mL, 1.2 mmol, 1.4 equiv.) and THF (4 mL) to a flame-dried 25 mL round-bottom flask. The solution was cooled to −78° C. and n-BuLi (1.9 M, 0.56 mL, 1.1 mmol, 1.3 equiv.) was added. After 10 minutes at this temperature, (R)-1 (100 mg, 0.82 mmol, 1.0 equiv.) in THF (0.8 mL) was added via cannula (0.2 mL THF rinse). This mixture stirred for 30 minutes before adding Me-I (0.10 mL, 1.6 mmol, 2.0 equiv.). This resulting mixture was allowed to stir at −78° C. for 40 minutes before adding HMPA (0.47 mL, 2.7 mmol, 3.3 equiv.). The reaction was kept at this temperature for 2 hours before warming to room temperature. Upon the observed consumption of starting material by TLC (after 1 h at room temperature), the yellow reaction was quenched with saturated NH$_4$Cl solution and extracted with ether. The combined organic layers were dried over MgSO$_4$ and the solvent evaporated under reduced pressure carefully due to volatility of the product. The crude material was purified by flash chromatography on silica gel with 15% ether/pentanes, yielding a yellow oil as a mixture of diastereomers. This lack of selectivity is insignificant for our purposes, as formation of the silyl bis-enol ether destroys the stereochemistry at that alpha position (101 mg, 0.74 mmol, 90%, the $^1$H NMR spectrum shows minor impurities from grease, but due to the volatility of the compound, it was not purified further): IR (Germanium ATR): 2928, 1678, 1389, 916 cm$^{-1}$; $^1$H NMR (499 MHz, Chloroform-d) δ 6.94-6.86 (m, 2H), 6.06-5.97 (m, 2H), 5.76 (dddd, J=21.7, 17.8, 10.3, 7.7 Hz, 2H), 5.15-5.04 (m, 4H), 2.85 (s, 1H), 2.62-2.50 (m, 2H), 2.49-2.38 (m, 3H), 2.38-2.30 (m, 1H), 2.30-2.22 (m, 1H), 1.12 (d, J=6.7 Hz, 3H), 1.05 (d, J=7.1 Hz, 3H); $^{13}$C NMR (126 MHz, CDCl$_3$) δ 202.5, 201.3, 148.1, 147.9, 140.3, 137.6, 129.5, 129.1, 116.7, 116.2, 46.8, 46.2, 45.5, 43.4, 32.4, 29.5, 12.9, 11.5; HRMS (ESI): Exact mass calc'd for C$_9$H$_{13}$O [M+H]$^+$, 137.0966. Found 137.0957.

Scheme S5. Synthesis of compound 3.

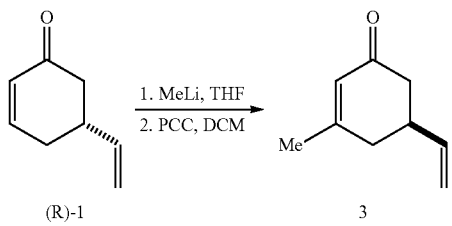

(R)-1    3

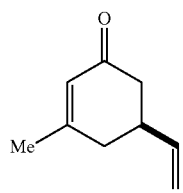

Compound 3.

(R)-1 (400 mg, 3.27 mmol, 1.0 equiv.) was diluted with THF (6.5 mL, 0.5M) in a flame-dried 25 mL round-bottom flask. The solution was cooled to −78° C. and a solution of MeLi (1.6 M, 3.1 mL, 4.90 mmol, 1.5 equiv.) was added dropwise. The reaction was warmed to 0° C. and then slowly allowed to warm to room temperature in the ice bath. After observed consumption of the starting material by TLC (2.5 hours), the yellow mixture was quenched with water, and extracted with ether. The combined organic layers were washed with brine, dried over $MgSO_4$ and the solvent evaporated under reduced pressure. The crude material was used directly in the next reaction. To a flame-dried 25 mL round-bottom flask was added PCC (1.4 g, 6.54 mmol, 2.0 equiv.), DCM (13 mL), and 0.3 g silica gel. The crude alcohol in DCM (1 mL) was added via cannula at room temperature (0.3 mL DCM rinse). The solution turned dark brown upon addition. Following the observed consumption of starting material by TLC (3 hours), the brown mixture was filtered through a mixture of Celite and silica gel with 50% ether/pentane and the solvent evaporated under reduced pressure carefully due to the volatility of the product. The crude material was purified by flash chromatography on silica gel with 10% to 15% ether/pentane to yield a slight yellow oil (264 mg, 1.94 mmol, 59% over two steps): $[\alpha]_D$=+60.7 (c 0.6, $CHCl_3$); IR (Germanium ATR): 3081, 2979, 1664, 1380, 912 $cm^{-1}$; $^1H$ NMR (400 MHz, Chloroform-d) δ 5.93-5.87 (m, 1H), 5.82 (ddd, J=17.1, 10.4, 6.4 Hz, 1H), 5.12-5.02 (m, 2H), 2.84-2.71 (m, 1H), 2.54-2.45 (m, 1H), 2.37 (dd, J=18.1, 4.8 Hz, 1H), 2.28-2.16 (m, 2H), 1.98 (d, J=1.4 Hz, 3H); $^{13}C$ NMR (126 MHz, $CDCl_3$) δ 199.1, 161.4, 140.4, 126.7, 114.7, 76.9, 42.6, 38.7, 37.0; HRMS (ESI): Exact mass calc'd for $C_9H_{13}O$ $[M+H]^+$, 137.0966. Found 137.0959.

Scheme S6. Synthesis of compound 4.

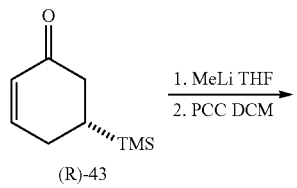

(R)-43

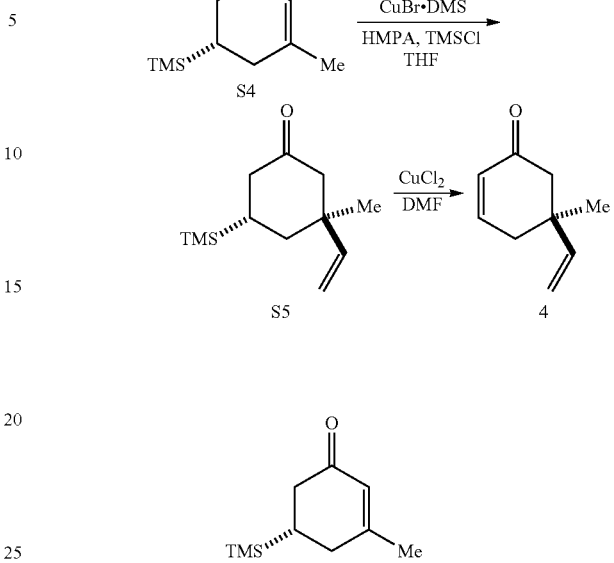

S4

S5    4

Compound S4.

(R)-43 (1.0 g, 5.9 mmol, 1.0 equiv.) and THF (12 mL, 0.5M) were added to a flame-dried 50 mL round-bottom flask. The flask was cooled to −78° C., and a solution of MeLi (1.6 M, 5.6 mL, 8.9 mmol, 1.5 equiv.) was added dropwise. The reaction was warmed to 0° C. and then slowly to room temperature. Upon observed consumption of starting material by TLC (2 h), the mixture was quenched with water and extracted with ether. The combined organic layers were dried over $MgSO_4$ and the solvent evaporated under reduced pressure. The crude material was taken on to the next reaction. To a flame-dried 50 mL round-bottom flask was added PCC (2.5 g, 11.8 mmol, 2.0 equiv.), DCM (25 mL), and 0.5 g silica gel. The crude material was diluted in DCM (2 mL) and added via cannula to the reaction flask at room temperature (0.5 mL DCM rinse). Following observed consumption of starting material by TLC (1.5 hours), the black mixture was filtered through a mixture of Celite and silica gel with 50% ether/pentane. The crude material was purified by flash chromatography with silica gel using 10% ether/pentane (0.73 g, 4.0 mmol, 68% over two steps): $[\alpha]_D$=+67.6 (c 0.054, $CHCl_3$); IR (Germanium ATR): 2952, 1668, 1630, 1251, 833 $cm^{-1}$; $^1H$ NMR (499 MHz, Chloroform-d) δ 5.86 (s, 1H), 2.40-2.32 (m, 1H), 2.17 (d, J=8.1 Hz, 2H), 2.10 (dd, J=16.3, 14.6 Hz, 1H), 1.95 (d, J=1.3 Hz, 3H), 1.44-1.33 (m, 1H), 0.03 (d, J=1.0 Hz, 9H); $^{13}C$ NMR (126 MHz, $CDCl_3$) δ 200.3, 163.5, 126.4, 37.8, 32.2, 24.4, 23.1, −3.6; HRMS (ESI): Exact mass calc'd for $C_{10}H_{19}OSi$ $[M+H]^+$, 183.1205. Found 183.1195.

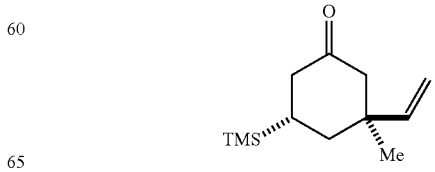

Compound S5.

LiCl (34 mg, 0.796 mmol, 20 mol %) and CuI (76 mg, 0.398 mmol, 10 mol %) were added to a flame-dried 50 mL round-bottom flask, cooled to 0° C., and S4 (0.726 g, 3.98 mmol, 1.0 equiv.) in THF (5 mL) was added (1 mL THF rinse). The solution was further diluted with THF (18 mL), and then TMS-Cl (0.56 mL, 4.38 mmol, 1.1 equiv.) was added. The mixture stirred for 20 minutes at 0° C. before adding freshly prepared and titrated vinylmagnesium bromide solution (0.93 M, 5.2 mL, 4.78 mmol, 1.2 equiv.) dropwise over 20 minutes. Upon observed consumption of the starting material by TLC (2 hours), the black reaction was quenched with saturated NH$_4$Cl, and extracted with ether. The combined organic layers were washed three times with 1M HCl before drying over MgSO$_4$ and removing the solvent under reduced pressure. The crude material was purified by flash chromatography with silica gel using 5% ether/pentane (509 mg, 2.42 mmol, 61%): [α]$_D$=−41.0 (c 0.30, CHCl$_3$); IR (Germanium ATR): 2954, 1709, 1247, 839 cm$^{-1}$; $^1$H NMR (500 MHz, Chloroform-d) δ 5.60 (dd, J=17.6, 10.9 Hz, 1H), 5.06 (d, J=10.9 Hz, 1H), 4.99 (d, J=17.6 Hz, 1H), 2.51 (dt, J=14.2, 2.5 Hz, 1H), 2.27-2.15 (m, 2H), 1.96 (t, J=14.2 Hz, 1H), 1.63 (dq, J=13.8, 2.5 Hz, 1H), 1.57-1.41 (m, 1H), 1.18 (tt, J=13.8, 3.4 Hz, 1H), 1.11 (s, 3H), −0.01 (d, J=0.8 Hz, 9H); $^{13}$C NMR (126 MHz, CDCl$_3$) δ 212.1, 144.8, 114.5, 51.2, 43.9, 41.6, 38.6, 30.5, 22.2, −3.6; HRMS (ESI): Exact mass calc'd for C$_{12}$H$_{23}$OSi [M+H]$^+$, 211.1518. Found 211.1506.

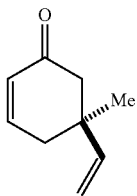

Compound 4.

CuCl$_2$ (0.60 g, 3.84 mmol, 3.0 equiv.) was added to a flame-dried 25 mL round-bottom flask. DMF (8 mL) was added to the flask. S5 (270 mg, 1.28 mmol, 1.0 equiv.) in DMF (1 mL, with an additional 0.8 mL DMF rinse) was added and the reaction heated to 65° C. overnight. The green reaction was diluted with water and extracted twice with pentane and once with 5% ether/pentane. The combined organic layers were dried over MgSO$_4$ and the solvent removed under reduced pressure carefully due to the volatility of the product. The crude material was purified by flash chromatography with silica gel using 10% ether/pentane, yielding a yellow oil (55.4 mg, 0.41 mmol, 38% unoptimized): [α]$_D$=+37.0 (c 0.60, CHCl$_3$); IR (Germanium ATR): 2924, 1680, 1388, 914 cm$^{-1}$; $^1$H NMR (400 MHz, Chloroform-d) δ 6.86 (dt, J=10.1, 4.1 Hz, 1H), 6.03 (dt, J=10.1, 2.1 Hz, 1H), 5.78 (dd, J=17.4, 10.8 Hz, 1H), 5.07-4.92 (m, 2H), 2.55-2.25 (m, 4H), 1.14 (s, 3H); $^{13}$C NMR (126 MHz, CDCl$_3$) δ 199.2, 147.8, 145.0, 129.6, 112.6, 49.3, 39.7, 38.1, 26.7; HRMS (ESI): Exact mass calc'd for C$_9$H$_{12}$ONa [M+Na]$^+$, 159.0786. Found 159.0775.

It should be noted that unreacted starting material was reisolated, as well as chlorinated products that could be converted back to starting material upon treatment with Zn and AcOH.

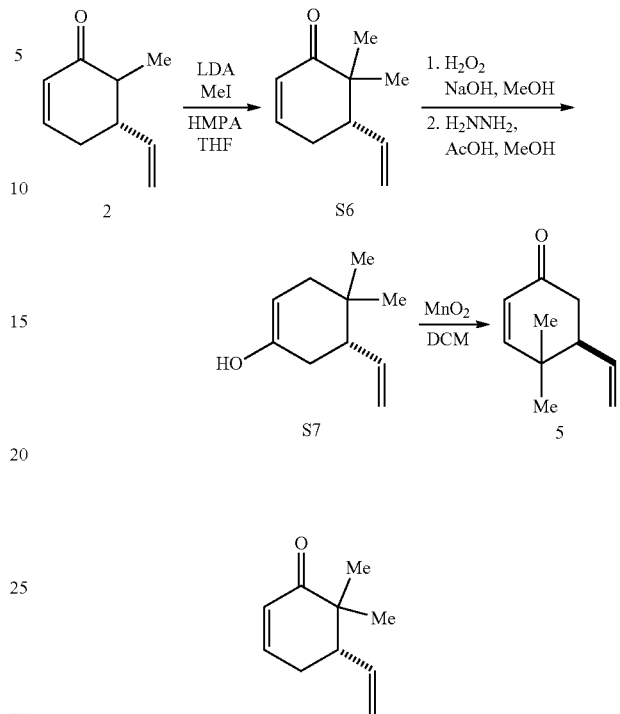

Scheme S7. Formation of compound 5.

Compound S6.

A solution of LDA was prepared by adding diisopropylamine (0.108 mL, 0.77 mmol, 1.4 equiv.) and THF (2.5 mL) to a flame-dried 10 mL round-bottom flask. The solution was cooled to −78° C. and n-BuLi (2.24 M, 0.32 mL, 0.72 mmol, 1.3 equiv.) was added. After 10 minutes at this temperature, 2 (75 mg, 0.55 mmol, 1.0 equiv.) in THF (0.5 mL) was added via cannula (0.4 mL THF rinse). This mixture stirred for 50 minutes before adding Me-I (69 μL, 1.1 mmol, 2.0 equiv.). This resulting mixture was allowed to stir at −78° C. for 40 minutes before adding HMPA (0.32 mL, 1.8 mmol, 3.3 equiv.). The reaction slowly warmed to room temperature overnight. The orange reaction was quenched with saturated NH$_4$Cl solution and extracted with ether. The combined organic layers were dried over MgSO$_4$ and the solvent evaporated under reduced pressure carefully due to volatility of the product. The crude material was purified by flash chromatography on silica gel with 5% ether/pentanes, yielding a yellow oil (49 mg, 0.33 mmol, 59%): [α]$_D$=−50.7 (c 0.70, CHCl$_3$); IR (Germanium ATR): 2969, 1707, 1676, 1388, 916 cm$^{-1}$; $^1$H NMR (500 MHz, Chloroform-d) δ 6.85 (ddd, J=10.1, 4.8, 3.2 Hz, 1H), 5.96 (ddd, J=10.1, 2.4, 1.7 Hz, 1H), 5.84 (ddd, J=16.6, 10.8, 8.5 Hz, 1H), 5.14-5.08 (m, 2H), 2.57-2.48 (m, 1H), 2.45-2.32 (m, 2H), 1.13 (s, 3H), 1.00 (s, 3H); $^{13}$C NMR (126 MHz, CDCl$_3$) δ 204.4, 147.3, 137.4, 128.3, 117.3, 49.0, 44.8, 29.6, 22.7, 19.4; HRMS (ESI): Exact mass calc'd for C$_{10}$H$_{15}$O [M+H]$^+$, 151.1123. Found 151.1115.

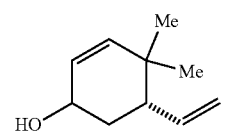

Compound S7.

S6 (327 mg, 2.17 mmol, 1.0 equiv.) was added to a 50 mL round-bottom flask and diluted with MeOH (21 mL). The solution was cooled to 0° C. and aqueous NaOH (1 M, 0.65 mL, 0.65 mmol, 0.3 equiv.) was added dropwise, followed by the slower dropwise addition of 30 wt % $H_2O_2$ (0.32 mL, 2.8 mmol, 1.3 equiv.), and the reaction slowly warmed to room temperature. Upon observed consumption of the starting material by TLC (2 hours), the reaction was poured into saturated $Na_2SO_3$ and extracted with DCM. The combined organic layers were dried over $MgSO_4$ and the solvent evaporated under reduced pressure. The crude epoxide was taken directly on to the next reaction by diluting the material with MeOH (20 mL) in a flame-dried 50 mL round-bottom flask. The solution was cooled to 0° C. and $NH_2NH_2 \cdot H_2O$ (0.21 mL, 6.7 mmol, 3.1 equiv.) was added. The reaction stirred for 15 minutes before adding AcOH (0.25 mL, 4.3 mmol, 2.0 equiv.). The reaction was warmed to room temperature. Upon observed consumption of the starting material by TLC (6 hours), the yellow reaction was poured into saturated $NaHCO_3$ and extracted with DCM. The combined organic layers were washed with brine, dried over $MgSO_4$, and the solvent evaporated under reduced pressure. The crude material was purified by flash chromatography with silica gel using a 10% ether/pentane to 30% ether/pentane solvent gradient (177 mg, 1.16 mmol, 54% over two steps): $[\alpha]_D$=+65.8 (c 0.36, $CHCl_3$); IR (Germanium ATR): 3347, 3015, 2934, 1039, 910 cm$^{-1}$; $^1$H NMR (500 MHz, Chloroform-d) δ 5.85-5.75 (m, 1H), 5.69 (ddt, J=9.9, 4.6, 1.3 Hz, 1H), 5.62 (dt, J=9.9, 1.0 Hz, 1H), 5.10-5.07 (m, 1H), 5.05 (d, J=1.3 Hz, 1H), 4.18 (dt, J=6.8, 3.4 Hz, 1H), 2.29 (ddd, J=12.0, 8.3, 3.7 Hz, 1H), 1.85-1.70 (m, 2H), 1.02 (d, J=1.0 Hz, 3H), 0.82 (d, J=1.0 Hz, 3H); $^{13}$C NMR (126 MHz, $CDCl_3$) δ 142.8, 139.4, 125.1, 115.8, 64.1, 43.6, 35.0, 33.9, 28.6, 22.0; HRMS (EI): Exact mass calc'd for $C_{10}H_{16}O$ [M]$^+$, 152.1201. Found 152.1227.

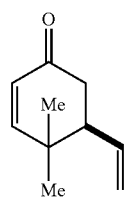

Compound 5.

S7 (175 mg, 1.1 mmol, 1.0 equiv.) was diluted in DCM (2.5 mL, 0.5 M) in a flame-dried 10 mL round-bottom flask. $MnO_2$ (0.99 g, 11.5 mmol, 10 equiv.) was added at room temperature and the reaction stirred overnight. The black mixture was filtered through Celite with 50% ether/pentane and the solvent carefully evaporated under reduced pressure, yielding pure yellow oil product (158 mg, 1.05 mmol, 95%): $[\alpha]_D$=+16.9 (c 0.49, $CHCl_3$); IR (Germanium ATR): 2960, 1684, 1268, 920 cm$^{-1}$; $^1$H NMR (499 MHz, Chloroform-d) δ 6.67 (dd, J=10.1, 1.3 Hz, 1H), 5.87 (d, J=10.1 Hz, 1H), 5.85-5.75 (m, 1H), 5.14 (d, J=10.4 Hz, 1H), 5.09 (d, J=17.1 Hz, 1H), 2.57 (dt, J=13.0, 6.9 Hz, 1H), 2.50-2.37 (m, 2H), 1.16 (d, J=1.3 Hz, 3H), 1.03 (d, J=1.3 Hz, 3H); $^{13}$C NMR (126 MHz, $CDCl_3$) δ 199.6, 160.6, 137.2, 126.7, 117.2, 48.5, 39.7, 36.0, 27.9, 21.2; HRMS (ESI): Exact mass calc'd for $C_{10}H_{15}O$ [M+H]$^+$, 151.1123. Found 151.1120.

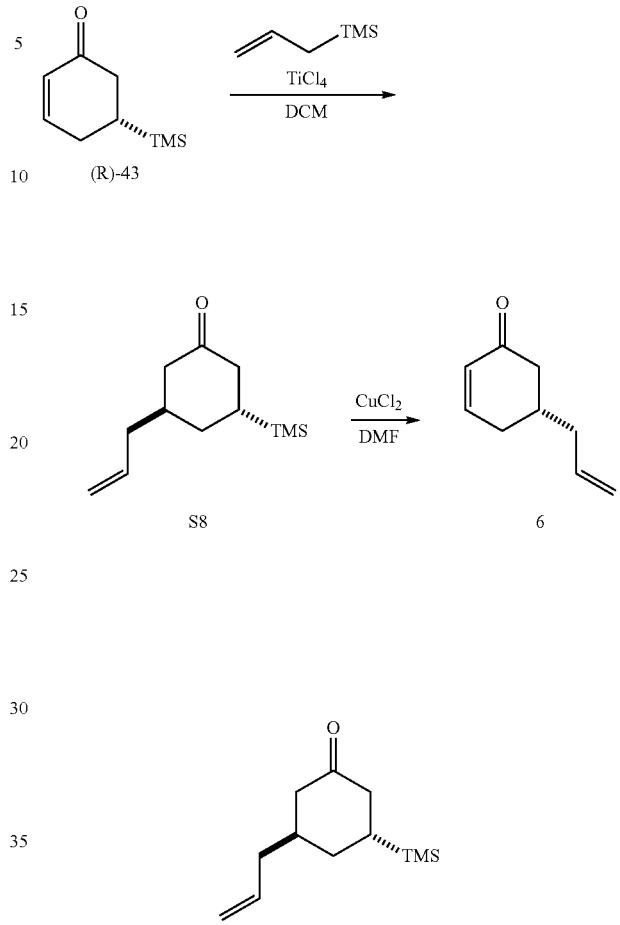

Compound S8.

The Hosomi-Sakurai reaction was achieved using conditions reported by Takei and coworkers.[6] (R)-43 (300 mg, 1.78 mmol, 1.0 equiv.) and DCM (8.9 mL, 0.2 M) were added to a flame-dried 25 mL round-bottom flask. The solution was cooled to -78° C., and allyl trimethylsilane (0.42 mL, 2.67 mmol, 1.5 equiv.) was added. Then, $TiCl_4$ (1 M, 2.14 mL, 2.14 mmol, 1.2 equiv.) was added to the reaction slowly. After 30 minutes, the starting material was consumed as observed by TLC, and water was added to the reaction at -78° C. and the cold bath removed. The mixture was extracted with DCM and the combined organic layers dried over $MgSO_4$ and solvent evaporated under reduced pressure. The crude material was purified by flash chromatography with silica gel using 5% ether/pentane, yielding a yellow oil (240 mg, 1.14 mmol, 64%, $^1$H NMR shows very minor impurities but the material was taken forward to the next reaction): $[\alpha]_D$=+95.2 (c 0.05, $CHCl_3$); IR (Germanium ATR): 2953, 1710, 1641, 1249, 841 cm$^{-1}$; $^1$H NMR (500 MHz, Chloroform-d) δ 5.70 (ddt, J=17.2, 10.4, 7.1 Hz, 1H), 5.11-4.96 (m, 2H), 2.48 (ddd, J=13.7, 5.6, 1.0 Hz, 1H), 2.32-2.19 (m, 3H), 2.17-2.00 (m, 3H), 1.72-1.66 (m, 2H), 1.27 (dddd, J=12.9, 9.3, 6.8, 4.3 Hz, 1H), -0.01 (s, 9H); $^{13}$C NMR (126 MHz, $CDCl_3$) δ 212.9, 136.4, 116.8, 46.5, 42.3, 37.7, 37.6, 29.5, 21.5, -3.4; HRMS (ESI): Exact mass calc'd for $C_{12}H_{22}OSiNa$ [M+Na]$^+$, 233.1338. Found 233.1328.

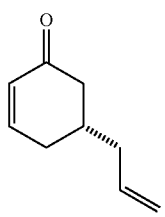

Compound 6.

CuCl$_2$ (600 mg, 4.17 mmol, 3.0 equiv.) was added to a flame-dried 25 mL round-bottom flask. S8 (292 mg, 1.39 mmol, 1.0 equiv.) in DMF (9 mL, with an additional 1.7 mL DMF rinse) was added via cannula and the reaction was heated to 55° C. for two hours. The green reaction was cooled to room temperature, diluted with water and extracted with pentane two times and 5% ether/pentane one time. The combined organic layers were dried over MgSO$_4$ and the solvent removed under reduced pressure carefully due to the volatility of the product. The crude material was purified by flash chromatography with silica gel using 10% ether/pentane, yielding a yellow oil (138 mg, 1.01 mmol, 73%): [α]$_D$=−59.4 (c 0.43, CHCl$_3$); IR (Germanium ATR): 3076, 2908, 1681, 1641, 1388, 916 cm$^{-1}$; $^1$H NMR (500 MHz, Chloroform-d) δ 6.96 (ddd, J=10.0, 5.6, 2.6 Hz, 1H), 6.02 (dt, J=10.0, 2.6, 1.2 Hz, 1H), 5.75 (ddt, J=16.0, 10.7, 6.9 Hz, 1H), 5.17-4.96 (m, 2H), 2.53 (ddd, J=14.7, 3.0, 1.8 Hz, 1H), 2.44 (dtd, J=18.5, 5.6, 3.8, 1.8 Hz, 1H), 2.22-2.12 (m, 4H), 2.13-2.03 (m, 1H); $^{13}$C NMR (126 MHz, CDCl$_3$) δ 199.9, 149.8, 135.4, 130.0, 117.4, 44.2, 40.1, 35.0, 31.9; HRMS (ESI): Exact mass calc'd for C$_9$H$_{13}$O [M+H]$^+$, 137.0966. Found 137.0961.

Scheme S9. Elabroation of (R)-7 into α-methyl substituted compound 8.

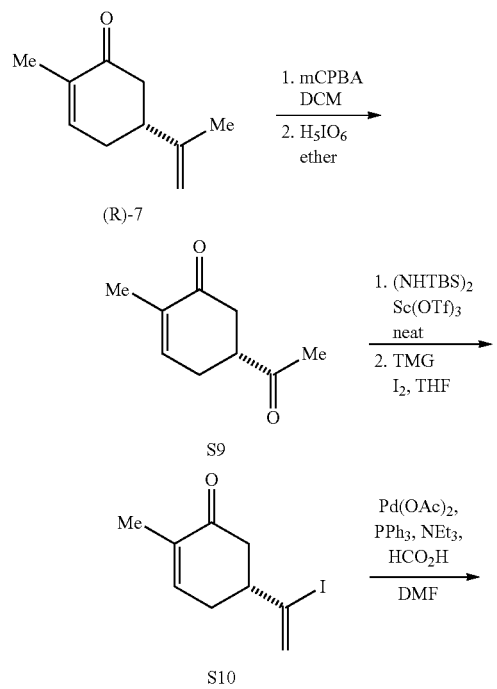

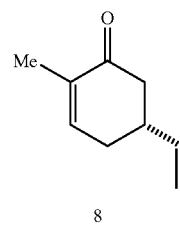

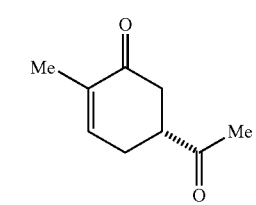 [SMILES: CC(=O)[C@@H]1CC=C(C)C(=O)C1]

Compound S9.

This compound was prepared as reported by Miftakhov and coworkers.[7] (R)-carvone ((R)-7) (3.0 g, 20.0 mmol, 1.0 equiv.) and DCM (200 mL, 0.1 M) were added to an oven-dried 500 mL round-bottom flask. The solution was cooled to 0° C. before adding mCPBA (5.2 g, 30.0 mmol, 1.5 equiv.) in three portions. Upon observed consumption of the starting material by TLC (after 5 hours), the reaction was quenched with saturated NaHCO$_3$ and extracted with DCM. The combined organic layers were washed with brine, dried over MgSO$_4$, and the solvent evaporated under reduced pressure. The crude epoxide was taken on to the next reaction, where it was diluted in ether (500 mL), cooled to 0° C., and H$_5$IO$_6$ (7.3 g, 32.0 mmol, 1.6 equiv.) was added in three portions. The reaction was left to stir overnight, after which it was diluted with saturated NaHCO$_3$ and extracted with ether. The combined organic layers were washed with brine, dried with MgSO$_4$, and the solvent evaporated under reduced pressure. The crude material was purified using flash chromatography on silica gel using 20% to 50% ether/pentanes yielding a yellow oil (2.1 g, 13.8 mmol, 69% over two steps): $^1$H NMR (500 MHz, Chloroform-d) δ 6.70 (ddq, J=4.8, 3.0, 1.5 Hz, 1H), 3.10 (dddd, J=12.1, 9.5, 5.4, 4.2 Hz, 1H), 2.69 (ddd, J=16.4, 4.2, 1.1 Hz, 1H), 2.58-2.45 (m, 3H), 2.19 (s, 3H), 1.78 (q, J=1.8 Hz, 3H); $^{13}$C NMR (126 MHz, CDCl$_3$) δ 208.0, 197.6, 142.8, 136.0, 48.3, 39.6, 28.0, 27.6, 15.9; HRMS (ESI): Exact mass calc'd for C$_9$H$_{13}$O$_2$ [M+H]$^+$, 153.0916. Found 153.0910. All spectroscopic data for this compound agrees with previously reported values.[7]

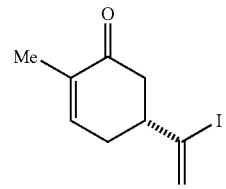

Compound S10.

This vinyl iodide was prepared employing chemistry developed in the Myers laboratory.[8] Sc(OTf)$_3$ (2 mg, 0.004 mmol, 1.0 mol %) was added to a flame-dried 50 mL conical flask, and was purged with N$_2$ for 10 minutes. The flask was cooled to 0° C. and (TBSNH)$_2$ (10.3 g, 39.4 mmol, 1.0 equiv.), which was prepared as described by Myers et al. in the same report, was added via syringe. S9 (6.0 g, 39.4 mmol) was added via syringe over 15 minutes. The solution gradually warmed to room temperature, and monitored by taking NMR aliquots. After all of the starting material had been consumed (after 3 hours), the yellow hydrazone was placed carefully on the vacuum manifold for one hour at room temperature, and then heated to 35° C. under high vacuum overnight. The crude material was used directly in the next reaction. I$_2$ (50 g, 197 mmol, 5.0 equiv.) and THF (200 mL) were added to an oven-dried 1 L round-bottom flask. The mixture was cooled to 0° C. and placed under a box with the hood lights off. Tetramethylguanidine (99 mL, 788 mmol, 20 equiv.) was cannulated to the flask. The crude material (11.0 g, 39.4 mmol, 1.0 equiv.) in THF (50 mL) was cannulated to the flask in the dark over 2 hours. After 15 minutes following the completed addition of the starting material, the reaction was quenched with saturated NaS$_2$O$_3$, extracted with ether, and the combined organic layers washed with saturated NaS$_2$O$_3$, 1 M HCl, and saturated NaHCO$_3$. The combined organic layers were dried over MgSO$_4$, and the solvent evaporated under reduced pressure. The crude orange oil was purified by flash chromatography on silica gel using a pentane to 5% ether/pentane solvent gradient (4.95 g, 18.9 mmol, 48% over two steps, $^1$H NMR shows very minor impurities, but the material was not purified further and taken on to the next reaction): [α]$_D$= +0.6 (c 0.23, CHCl$_3$); IR (Germanium ATR): 2921, 1672, 1365, 902 cm$^{-1}$; $^1$H NMR (499 MHz, Chloroform-d) δ 6.72 (ddd, J=4.9, 3.1, 1.5 Hz, 1H), 6.19 (t, J=1.4 Hz, 1H), 5.82 (d, J=1.9 Hz, 1H), 2.70-2.53 (m, 2H), 2.53-2.38 (m, 3H), 1.79 (p, J=2.0 Hz, 3H); $^{13}$C NMR (126 MHz, CDCl$_3$) δ 197.9, 143.3, 135.9, 125.8, 116.4, 48.2, 44.4, 32.8, 15.8; HRMS (GC-TOF): Exact mass calc'd for C$_7$H$_9$O [M-CH$_2$CO]$^+$, 219.9749. Found 219.9749.

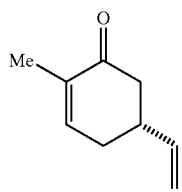

Compound 8.

S10 (388 mg, 1.48 mmol, 1.0 equiv.) and DMF (4.4 mL, 0.34M) were added to a flame-dried 10 mL round-bottom flask outfitted with a reflux condenser. Pd(OAc)$_2$ (7.0 mg, 0.03 mmol, 2.0 mol %), PPh$_3$ (20 mg, 0.07 mmol, 5.0 mol %), NEt$_3$ (0.66 mL, 4.74 mmol, 3.2 equiv.), and formic acid (56 μL, 1.48 mmol, 1.0 equiv.) were added sequentially and the reaction was heated to 60° C. Upon observed consumption of the starting material by TLC after 1.5 hours, the dark red reaction was cooled to room temperature, diluted with water, and extracted with pentanes. The combined organic layers were washed with brine, dried over MgSO$_4$, and the solvent evaporated under reduced pressure carefully due to the volatility of the product. The crude material was purified by flash chromatography on silica gel using 5% ether/pentane to yield a light yellow oil (175 mg, 1.28 mmol, 87%): α$_D$=-58.0 (c 0.54, CHCl$_3$); IR (Germanium ATR): 2923, 1672, 1642, 1365, 910 cm$^{-1}$; $^1$H NMR (400 MHz, Chloroform-d) δ 6.72 (ddq, J=5.7, 2.9, 1.4 Hz, 1H), 5.82 (dddd, J=16.9, 10.4, 6.4, 1.1 Hz, 1H), 5.12-4.96 (m, 2H), 2.86-2.67 (m, 1H), 2.58 (ddt, J=16.2, 4.1, 1.3 Hz, 1H), 2.45 (dddt, J=18.4, 7.3, 4.3, 1.4 Hz, 1H), 2.38-2.14 (m, 2H), 1.78 (dq, J=2.6, 1.3 Hz, 3H); $^{13}$C NMR (126 MHz, CDCl$_3$) δ 199.4, 144.3, 140.6, 135.9, 114.5, 43.7, 39.3, 32.1, 15.9; HRMS (ESI): Exact mass calc'd for C$_9$H$_{13}$O [M+H]$^+$, 137.0966. Found 137.0957.

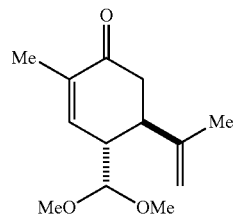 [SMILES: C=C(C)[C@@H]1CC(=O)C(C)=C[C@H]1C(OC)OC]

Compound 9.

This compound was prepared from S-carvone following a procedure reported by Inoue and coworkers.[9] FeCl$_3$ (325 mg, 2.0 mmol, 3 mol %) was added to a flame-dried flask and diluted with THF (120 mL). The mixture was cooled to −20° C., and MeMgBr (3.0 M, 49.0 mL, 147 mmol, 2.2 equiv.) was added over 2 hours. Then, a solution of (S)-carvone ((S)-7), (10.0 g, 66.6 mmol, 1.0 equiv.) in THF (38 mL) was added over 1.5 hours (2 mL THF rinse). The reaction stirred at −20° C. for 1.5 hours, after which it was warmed to 0° C., and TMS-Cl (11.8 mL, 93.2 mmol, 1.4 equiv.), DMPU (9.6 mL, 80.0 mmol, 1.2 equiv.), and NEt$_3$ (12.1 mL, 86.6 mmol, 1.3 equiv.) were added successively. The reaction was warmed to room temperature and stirred overnight. The black mixture was then cooled to 0° C., and quenched with pH 7 buffer. The mixture was filtered through Celite with EtOAc, extracted with EtOAc, and dried over MgSO$_4$. The crude material was purified by flash chromatography on silica gel using 5% EtOAc/hexane. This product was then diluted with DCM (133 mL) and CH(OMe)$_3$ (8.0 mL, 73.3 mmol, 1.1 equiv.), cooled to −50° C., and BF$_3$.OEt$_2$ (8.3 mL, 67.3 mmol, 1.01 equiv.) was added. The mixture stirred at −50° C. for 2.5 hours, after which the bright orange reaction was poured into saturated NaHCO$_3$ at 0° C. The mixture was extracted with DCM, and dried over MgSO$_4$. The crude material was purified by flash chromatography on silica gel with 20% ether/pentane (2.67 g, 11.9 mmol, 18% yield of major diastereomer over two steps): $^1$H NMR (500 MHz, Benzene-d$_6$) δ 6.86 (dt, J=3.1, 1.6 Hz, 1H), 4.69 (s, 1H), 4.67 (s, 1H), 4.05 (dd, J=3.3, 1.1 Hz, 1H), 3.12 (d, J=1.1 Hz, 3H), 3.05 (d, J=1.6 Hz, 3H), 2.72 (ddd, J=13.5, 9.9, 4.2 Hz, 1H), 2.43 (tdd, J=13.1, 4.8, 2.3 Hz, 2H), 2.18 (ddd, J=16.1, 12.7, 1.0 Hz, 1H), 1.85 (p, J=2.6 Hz, 3H), 1.41 (s, 3H); $^{13}$C NMR (126 MHz, C$_6$D$_6$) δ 197.3, 145.6, 143.3, 136.0, 112.9, 105.9, 56.2, 55.2, 45.0, 43.5, 42.8, 19.2, 16.1. All spectroscopic data for this compound agrees with previously reported values.[9]

Scheme S10. Synthesis of compound 10.

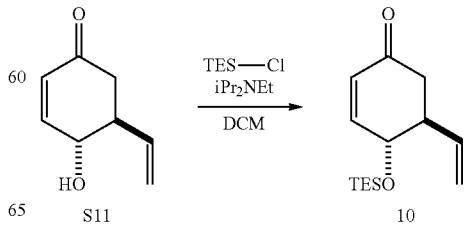

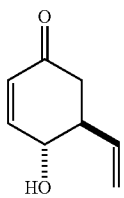

Compound S11.

This compound was prepared from quinic acid as detailed by Ventura et al.[10] $^1$H NMR (500 MHz, Chloroform-d) δ 6.93 (dd, J=10.2, 1.9 Hz, 1H), 5.98 (ddd, J=10.2, 2.3, 1.3 Hz, 1H), 5.79 (ddd, J=17.2, 10.4, 8.1 Hz, 1H), 5.31-5.19 (m, 2H), 4.36-4.25 (m, 1H), 2.72 (dtd, J=13.1, 8.7, 4.1 Hz, 1H), 2.57 (ddd, J=16.7, 4.1, 1.3 Hz, 1H), 2.34 (dd, J=16.7, 13.4 Hz, 1H); $^{13}$C NMR (126 MHz, CDCl$_3$) δ 197.9, 152.1, 137.3, 129.1, 118.8, 70.3, 49.2, 41.4. All spectroscopic data for this compound, as well as for all compounds leading to S11, agrees with the reported values.[11]

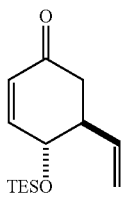

Compound 10.

S11 (75 mg, 0.54 mmol) was diluted in DCM (2 mL, 0.27 M). TES-Cl (0.10 mL, 0.60 mmol, 1.1 equiv.) was added to the flask. The mixture was cooled to 0° C. before adding Hünig's base (0.24 mL, 1.36 mmol, 2.5 equiv.) dropwise. The reaction slowly warmed to room temperature overnight. The yellow reaction was then poured into pH 7 buffer and extracted with DCM. The combined organic extracts were dried over Na$_2$SO$_4$. The crude material was purified by flash chromatography on silica gel with 10% ether/pentane (116.2 mg, 0.46 mmol, 85%): [α]$_D$=−111.2 (c 2.48, CHCl$_3$); IR (Germanium ATR): 2955, 2912, 2877, 1691, 1100, 894, 742 cm$^{-1}$; $^1$H NMR (500 MHz, Chloroform-d) δ 6.78 (dd, J=10.2, 2.1 Hz, 1H), 5.94 (ddd, J=10.2, 2.0, 1.2 Hz, 1H), 5.85 (ddd, J=17.4, 10.5, 7.1 Hz, 1H), 5.15-5.14 (m, 1H), 5.12 (dt, J=10.2, 1.2 Hz, 1H), 4.28 (dt, J=8.7, 2.1 Hz, 1H), 2.75 (ddddd, J=12.4, 9.7, 6.5, 3.1, 2.0 Hz, 1H), 2.59 (ddd, J=16.5, 4.1, 1.2 Hz, 1H), 2.33 (dd, J=16.6, 12.6 Hz, 1H), 0.98 (t, J=7.9 Hz, 9H), 0.65 (q, J=8.1 Hz, 6H); $^{13}$C NMR (126 MHz, CDCl$_3$) δ 198.5, 153.4, 138.0, 128.7, 116.7, 71.4, 48.2, 41.0, 6.9, 5.1; HRMS (ESI): Exact mass calc'd for C$_{14}$H$_{24}$O$_2$SiNa [M+Na]$^+$, 275.1443. Found 275.1445.

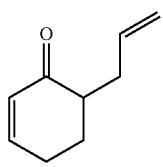

Compound 11.

A solution of LDA was prepared by adding diisopropylamine (1.02 mL, 7.3 mmol, 1.4 equiv.) and THF (21 mL) to a flame-dried 50 mL round-bottom flask. The solution was cooled to −78° C. and freshly titrated n-BuLi added (2.13 M, 3.2 mL, 6.8 mmol, 1.3 equiv.). After stirring for 10 minutes at this temperature, cyclohexenone (500 mg, 5.2 mmol, 1.0 equiv.) in THF (4 mL, with an additional 1 mL THF rinse) was added. This solution stirred for 30 minutes before DMPU (1.33 mL, 10.4 mmol, 2.0 equiv.) was added. The resulting solution stirred for another 50 minutes before allyl bromide (1.9 mL, 15.6 mmol, 3.0 equiv.) was added dropwise. The solution slowly warmed to room temperature. Upon observed consumption of the starting material by TLC (3 hours), the orange reaction was quenched with saturated NH$_4$Cl, and extracted with ether. The combined organic layers were dried over MgSO4 and the solvent evaporated under reduced pressure carefully due to the volatility of the product. The crude material was purified by flash chromatography on silica gel using 5% ether/pentane (191.2 mg, 1.40 mmol, 27% unoptimized): $^1$H NMR (499 MHz, Chloroform-d) δ 6.94 (dddd, J=10.2, 4.4, 3.2, 1.0 Hz, 1H), 6.00 (ddd, J=10.0, 2.4, 1.6 Hz, 1H), 5.78 (dddd, J=16.8, 10.1, 7.8, 6.3 Hz, 1H), 5.15-4.93 (m, 2H), 2.70-2.55 (m, 1H), 2.47-2.29 (m, 3H), 2.21-2.03 (m, 2H), 1.73 (dddd, J=13.6, 11.5, 9.0, 5.7 Hz, 1H); $^{13}$C NMR (126 MHz, CDCl$_3$) δ 201.1, 149.9, 136.3, 129.7, 116.9, 46.3, 33.8, 27.5, 25.4. All spectroscopic data for this compound agrees with previously reported values.[1]

[1]. Yamamoto, E.; Gokuden, D.; Nagai, A.; Kamachi, T.; Yoshizawa, K.; Hamasaki, A.; Ishida, T.; Tokunaga, M. *Org. Lett.* 2012, 14, 6178-6181.

3. Oxidative Coupling Experimental Procedures and Characterization Data

A. Synthesis of Symmetrical Silyl Bis-Enol Ether Intermediates

Scheme S11. General method A for synthesis of symmetrical silyl bis-enol ethers.

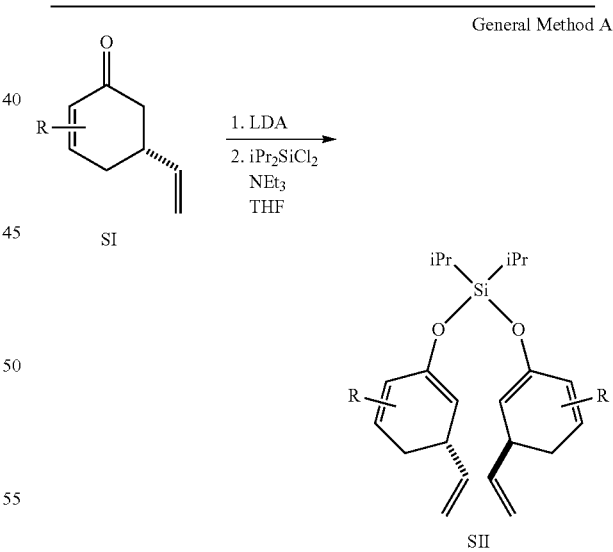

General Method A:

To a flame dried conical flask was added freshly distilled diisopropylamine (1.2 equiv.) and THF (0.17 M). The flask was cooled to −78° C., and n-BuLi (freshly titrated, 1.1 equiv.) was added. After 10 minutes, enone SI (1.0 equiv.) in THF (0.4 M) was added (0.3 mL rinse). The solution stirred at this temperature for 30 minutes before adding iPr$_2$SiCl$_2$ (freshly distilled, 0.5 equiv.) and NEt$_3$ (freshly distilled, 0.5 equiv.) in rapid succession. The mixture stirred at −78° C.

for 30 minutes before warming to room temperature. Upon observed consumption of the starting material by TLC (ranging from 1-3 hours), the orange reaction was quenched with pH 7 buffer and extracted with pentanes. The combined organic layers were dried over MgSO$_4$, and concentrated under reduced pressure. The crude material (SII) was placed on the vacuum manifold overnight and was then used directly in the subsequent oxidative coupling reaction.

B. Synthesis of Unsymmetrical Silyl Bis-Enol Ether Intermediates

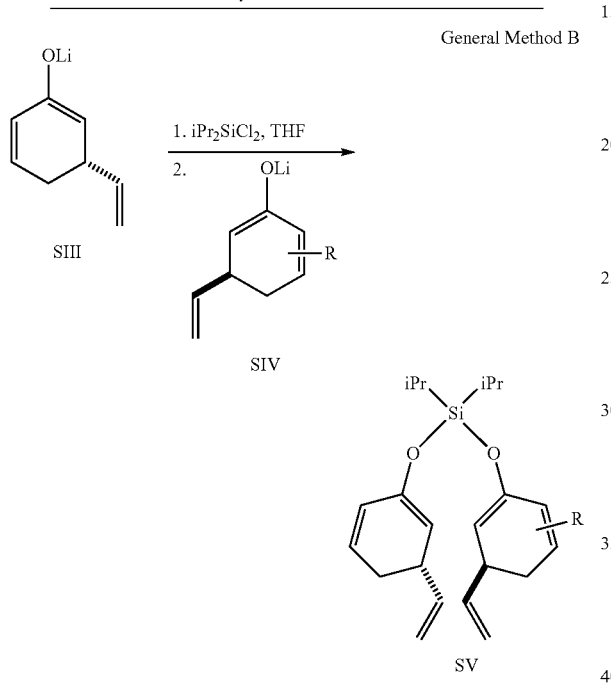

Scheme S12. General method B for synthesis of unsymmetrical silyl bis-enol ethers.

General Method B:

To a flame dried conical flask was added freshly distilled diisopropylamine (1.2 equiv.) and THF (0.72 M with respect to SIII). The flask was cooled to −78° C., and n-BuLi (freshly titrated, 1.1 equiv.) added. After 10 minutes, enone SIII (1.0 equiv.) in THF (1.7 M with respect to SIII) was added (with an additional 0.2 mL rinse). The solution stirred for 30 minutes before very slowly adding it via cannula to a flask containing iPr$_2$SiCl$_2$ (freshly distilled, 1.0 equiv.) and THF (0.25 M with respect to SIII), also at −78° C., dropwise in a controlled manner, over at least 1 hour (with an additional 0.2 mL THF rinse). Meanwhile, LDA was prepared exactly as above in a separate conical flask. After 10 minutes, enone SIV (1.0 equiv.) in THF (1.7 M with respect to SIII) was added to the LDA (with an additional 0.2 mL rinse). This solution stirred for 30 minutes before adding it slowly to the reaction flask via cannula over 1 hour (about 40 minutes following the completion of the first enolate addition, with an additional 0.2 mL THF rinse). The mixture stirred at −78° C. for 45 min and then was warmed to room temperature. Upon observed consumption of the starting materials by TLC (ranging from 1-3 hours), the orange reaction was quenched with pH 7 buffer and extracted with pentanes. The combined organic layers were dried over MgSO$_4$, and concentrated under reduced pressure. The crude material (SV) was placed on the vacuum manifold overnight and was used directly in the subsequent oxidative coupling reaction.

Note: The formation of the silyl bis-enol ether is more successful when the more hindered enone is added to the silane first. All enones to form cross-coupled products described below are listed in order of addition in the silyl bis-enol ether formation.

C. Oxidative Coupling: Dimerization or Cross Coupling

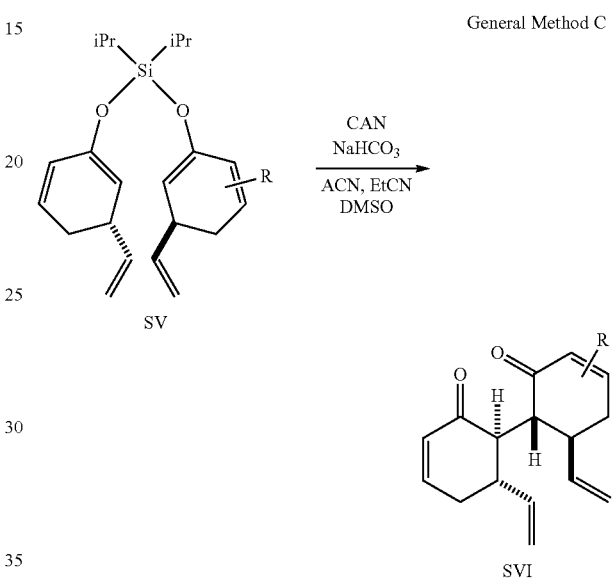

Scheme S13. General method C for the oxidative coupling of silyl bis-enol ether intermediates.

General Method C:

To a flame dried round bottom flask was added CAN (2.2 equiv.), NaHCO$_3$ (4.4 equiv.), ACN (distilled and dried over activated sieves, 0.03 M), and DMSO (2.0 equiv.) The mixture was cooled to −30° C. and stirred vigorously while silyl bis-enol ether SV in EtCN (distilled and dried over activated sieves, 0.2 M) was added (with an additional 0.2 mL rinse) via cannula. Upon observed consumption of the starting material by TLC (5-15 min.), the orange mixture was diluted with saturated NaHCO$_3$ solution, extracted with CHCl$_3$. The combined organic layers were dried over MgSO$_4$ filtered through Celite with EtOAc, and concentrated under reduced pressure. The crude material was purified by flash chromatography on silica gel using 5-10% EtOAc/hexane to yield 1,4-diketone product SVI.

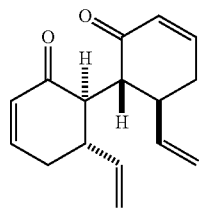 [SMILES: C=C[C@@H]1CC=CC(=O)[C@H]1[C@@H]1C(=O)C=CC[C@H]1C=C]

Compound 13a.

Enone (R)-1 (100 mg, 0.82 mmol) was converted to the silyl bis-enol ether according to General Method A, which was then subjected to oxidative conditions via General Method C to afford the crude 1,4-diketone 13a as a 3:1 mixture of diastereomers that were separated by flash chromatography (major product exhibits C2 symmetry: 48.4 mg, 0.20 mmol, 50% yield over two steps; total coupled yield: 65.2 mg, 0.27 mmol, 66%): IR (Germanium ATR): 2923, 1728, 1671, 1387, 812 cm$^{-1}$; $^1$H NMR (500 MHz, Chloroform-d) δ 6.89 (ddd, J=10.0, 6.0, 2.4 Hz, 1H), 6.02 (ddd, J=10.0, 2.8, 1.0 Hz, 1H), 5.61 (dt, J=17.1, 9.8 Hz, 1H), 5.13-5.03 (m, 2H), 3.23 (s, 1H), 2.81 (broad s, 1H), 2.37 (dt, J=18.6, 5.4 Hz, 1H), 2.27 (ddt, J=18.7, 11.3, 2.6 Hz, 1H); $^{13}$C NMR (126 MHz, CDCl$_3$) δ 199.5, 148.0, 140.8, 130.2, 117.2, 50.2, 44.5, 33.4; HRMS (ESI): Exact mass calc'd for C$_{16}$H$_{19}$O$_2$ [M+H]$^+$, 243.1385. Found 243.1383.

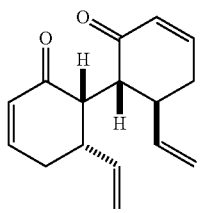 [SMILES: C=C[C@@H]1CC=CC(=O)[C@@H]1[C@@H]1C(=O)C=CC[C@H]1C=C]

Compound Epi-13a.

From the above reaction to form 13a, the minor diastereomer, epi-4a, was cleanly isolated (16.8 mg, 0.07 mmol, 16%) [α]$_D$=−128.4 (c 0.39, CHCl$_3$); IR (Germanium ATR): 3075, 2924, 1668, 1386, 911 cm$^{-1}$; $^1$H NMR (500 MHz, Chloroform-d) δ 6.91-6.84 (m, 1H), 6.81 (ddd, J=10.1, 5.0, 3.2 Hz, 1H), 6.19 (dt, J=10.2, 1.8 Hz, 1H), 5.93 (dt, J=10.3, 2.1 Hz, 1H), 5.90 (dt, J=17.0, 10.0 Hz, 1H), 5.76 (ddd, J=17.1, 10.2, 8.5 Hz, 1H), 5.19 (dt, J=17.0, 1.2 Hz, 1H), 5.11 (dd, J=10.2, 1.2 Hz, 1H), 4.96 (dd, J=17.1, 1.7 Hz, 1H), 4.90 (dd, J=10.0, 1.7 Hz, 1H), 3.23 (dd, J=10.0, 6.0 Hz, 1H), 2.92 (qd, J=8.7, 4.9 Hz, 1H), 2.85 (dq, J=9.1, 4.6 Hz, 1H), 2.68 (dd, J=6.0, 4.9 Hz, 1H), 2.59 (ddt, J=18.5, 5.4, 2.8 Hz, 1H), 2.51 (dtd, J=19.1, 5.0, 1.6 Hz, 1H), 2.43-2.35 (m, 1H), 2.31 (ddt, J=19.1, 8.3, 2.8 Hz, 1H); $^{13}$C NMR (126 MHz, CDCl$_3$) δ 198.3, 198.1, 147.0, 146.3, 139.5, 139.2, 130.5, 130.1, 116.6, 115.7, 50.5, 49.2, 41.1, 40.9, 32.2, 31.6; HRMS (ESI): Exact mass calc'd for C$_{16}$H$_{19}$O$_2$ [M+H]$^+$, 243.1385. Found 243.1378.

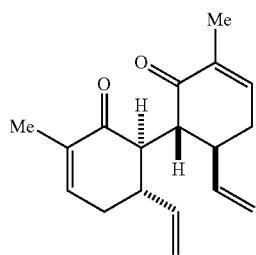 [SMILES: C=C[C@@H]1CC=C(C)C(=O)[C@H]1[C@@H]1C(=O)C(C)=CC[C@H]1C=C]

Compound 14a.

Enone 8 (100 mg, 0.734 mmol) was converted to the silyl bis-enol ether according to General Method A, which was then subjected to oxidative conditions via General Method C to afford the C2-symmetric 1,4-diketone 14a as a 20:1 mixture of diastereomers that was purified by flash chromatography (68 mg, 0.25 mmol, 68% yield over two steps): IR (Germanium ATR): 3076, 2922, 1659, 1366, 917 cm$^{-1}$; $^1$H NMR (500 MHz, Chloroform-d) δ 6.64 (dt, J=6.2, 1.9 Hz, 1H), 5.58 (dt, J=17.0, 9.8 Hz, 1H), 5.07 (dd, J=17.0, 1.8 Hz, 1H), 5.04-4.99 (m, 1H), 3.21 (s, 1H), 2.84-2.52 (broad m, 1H), 2.31 (dt, J=18.0, 5.5 Hz, 1H), 2.21 (ddt, J=18.0, 11.3, 2.6 Hz, 1H), 1.75 (t, J=2.6, 1.9 Hz, 3H); $^{13}$C NMR (126 MHz, CDCl$_3$) δ 199.8, 142.7, 141.2, 135.9, 116.8, 50.8, 45.0, 33.2, 16.2; HRMS (ESI): Exact mass calc'd for C$_{18}$H$_{23}$O$_2$ [M+H]$^+$, 271.1698. Found 271.1691.

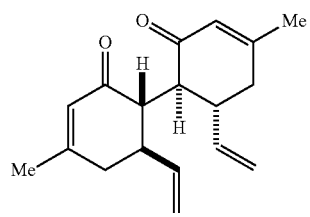 [SMILES: C=C[C@H]1CC(C)=CC(=O)[C@@H]1[C@H]1C(=O)C=C(C)C[C@@H]1C=C]

Compound 15a:

Enone 3 (110 mg, 0.808 mmol) was converted to the silyl bis-enol ether according to General Method A, which was then subjected to oxidative conditions via General Method C to afford the crude 1,4-diketone 15a as a 4:1 mixture of diastereomers that were separated by flash chromatography (major diastereomer exhibits C2 symmetry: 49.0 mg, 0.18 mmol, 45% yield over two steps; total coupled yield: 62.2 mg, 0.23 mmol, 57% over two steps): IR (Germanium ATR): 2926, 1732, 1659, 1379, 884 cm$^{-1}$; $^1$H NMR (499 MHz, Chloroform-d) δ 5.87 (s, 1H), 5.60 (dt, J=17.0, 9.8 Hz, 1H), 5.12-4.98 (m, 2H), 3.21 (s, 1H), 2.65 (broad s, 1H), 2.34-2.15 (m, 2H), 1.93 (s, 3H); $^{13}$C NMR (126 MHz, CDCl$_3$) δ 199.5, 159.7, 141.1, 127.0, 117.0, 48.9, 44.3, 38.6, 24.2; HRMS (ESI): Exact mass calc'd for C$_{18}$H$_{23}$O$_2$ [M+H]$^+$, 271.1698. Found 271.1697.

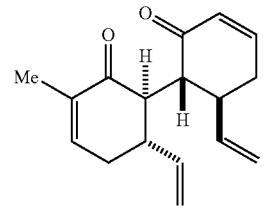 [SMILES: C=C[C@@H]1CC=CC(=O)[C@H]1[C@@H]1C(=O)C(C)=CC[C@H]1C=C]

Compound 16a.

Enones 8 (85.0 mg, 0.62 mmol) and (R)-1 (76.0 mg, 0.62 mmol) were converted to the silyl bis-enol ether according to General Method B, which was then subjected to oxidative conditions via General Method C to afford the crude 1,4-diketone 16a as a 7:1 mixture of diastereomers that were separated by flash chromatography (major diastereomer: 82.5 mg, 0.32 mmol, 52% yield over two steps; total coupled yield: 95.1 mg, 0.37 mmol, 60% over two steps): [α]$_D$= +24.3 (c 1.06, CHCl$_3$); IR (Germanium ATR): 2922, 1661, 1387, 917 cm$^{-1}$; $^1$H NMR (500 MHz, Chloroform-d) δ 6.88 (ddd, J=10.1, 6.0, 2.3 Hz, 1H), 6.65 (dt, J=6.2, 1.8 Hz, 1H), 6.01 (dd, J=10.1, 2.9 Hz, 1H), 5.61 (t, J=9.8 Hz, 1H), 5.57 (t, J=9.8 Hz, 1H), 5.09 (dd, J=6.2, 1.7 Hz, 1H), 5.08-5.01 (m, 3H), 3.22 (s, 2H), 2.87-2.58 (broad m, 2H), 2.47-2.10 (m, 4H), 1.73 (q, J=1.8 Hz, 3H); $^{13}$C NMR (126 MHz, CDCl$_3$) δ 199.7, 199.7, 147.8, 143.0, 141.1, 140.9, 135.8, 130.3, 117.1, 117.0, 50.5, 50.4, 45.0, 44.6, 33.3, 33.3, 16.2; HRMS (ESI): Exact mass calc'd for C$_{17}$H$_{21}$O$_2$ [M+H]$^+$, 257.1542. Found 257.1531.

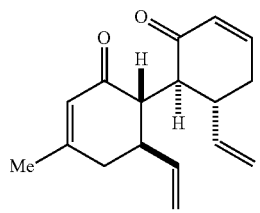 [SMILES: C=C[C@H]1CC=CC(=O)[C@@H]1[C@H]1C(=O)C=C(C)C[C@@H]1C=C]

Compound 17a.

Enones (S)-1 (82.0 mg, 0.67 mmol) and 3 (91.0 mg, 0.67 mmol) were converted to the silyl bis-enol ether according to General Method B, which was then subjected to oxidative conditions via General Method C to afford the crude 1,4-diketone 17a as a 3:1 mixture of diastereomers that were separated by flash chromatography (major diastereomer: 67.0 mg, 0.26 mmol, 39% yield over two steps; total coupled yield: 89.8 mg, 0.35 mmol, 52% over two steps): $[\alpha]_D$=+8.1 (c 1.06, CHCl$_3$); IR (Germanium ATR): 3075, 2916, 1656, 1380, 917 cm$^{-1}$; $^1$H NMR (500 MHz, Chloroform-d) δ 6.88 (ddd, J=10.0, 6.0, 2.4 Hz, 1H), 6.01 (dd, J=10.0, 2.8 Hz, 1H), 5.87 (q, J=1.4 Hz, 1H), 5.60 (dtd, J=17.1, 9.8, 1.7 Hz, 2H), 5.10 (d, J=1.6 Hz, 1H), 5.07 (d, J=1.6 Hz, 1H), 5.06-5.02 (m, 2H), 3.24 (d, J=22.7 Hz, 2H), 2.99-2.50 (broad m, 2H), 2.36 (dt, J=18.5, 5.5 Hz, 1H), 2.32-2.18 (m, 3H), 1.93 (s, 3H); $^{13}$C NMR (126 MHz, CDCl$_3$) δ 199.7, 199.2, 159.8, 147.9, 141.0, 140.9, 130.2, 127.0, 117.1, 117.1, 50.0, 49.1, 44.5, 44.4, 38.6, 33.4, 24.2; HRMS (ESI): Exact mass calc'd for C$_{17}$H$_{21}$O$_2$ [M+H]$^+$, 257.1542. Found 257.1539.

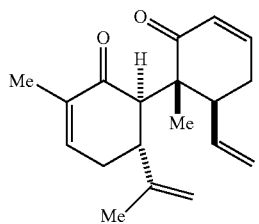

Compound 19a:

Enones (R)-7 (93.0 mg, 0.62 mmol) and 2 (85.0 mg, 0.62 mmol) were converted to the silyl bis-enol ether according to General Method B, which was then subjected to oxidative conditions via General Method C to afford 1,4-diketone 19a as a 20:1 mixture of diastereomers that was purified by flash chromatography (88.0 mg, 0.31 mmol, 50% yield over two steps): $[\alpha]_D$=−7.3 (c 1.40, CHCl$_3$); IR (Germanium ATR): 3033, 2922, 1655, 1379, 916 cm$^{-1}$; $^1$H NMR (500 MHz, Chloroform-d) δ 6.70 (dt, J=10.1, 4.0 Hz, 1H), 6.59 (tq, J=4.2, 1.4 Hz, 1H), 6.01 (dt, J=10.1, 2.1 Hz, 1H), 5.77 (dt, J=16.9, 9.8 Hz, 1H), 5.15 (dd, J=16.9, 1.8 Hz, 1H), 5.12 (dd, J=10.2, 1.8 Hz, 1H), 4.76 (s, 1H), 4.74 (p, J=1.5 Hz, 1H), 3.31 (ddd, J=9.5, 6.6, 5.2 Hz, 1H), 3.13 (q, J=6.1 Hz, 1H), 2.93 (d, J=5.9 Hz, 1H), 2.60-2.47 (m, 2H), 2.32-2.21 (m, 2H), 1.74 (q, J=1.9 Hz, 3H), 1.73-1.71 (m, 3H), 1.09 (s, 3H); $^{13}$C NMR (126 MHz, CDCl$_3$) δ 203.5, 200.7, 149.5, 144.4, 142.4, 137.8, 136.7, 129.4, 118.3, 111.9, 53.1, 52.7, 47.6, 43.3, 31.1, 30.1, 21.1, 16.5, 16.4; HRMS (ESI): Exact mass calc'd for C$_{19}$H$_{25}$O$_2$ [M+H]$^+$, 285.1855. Found 285.1855.

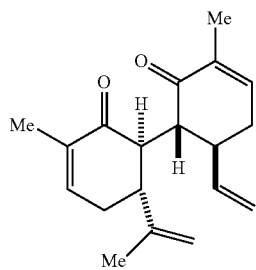 [SMILES: C=C[C@@H]1CC=C(C)C(=O)[C@H]1[C@@H]1C(=O)C(C)=CC[C@H]1C(=C)C]

Compound 18a:

Enones (R)-7 (24.8 mg, 0.165 mmol) and 8 (22.5 mg, 0.165 mmol) were converted to the silyl bis-enol ether according to General Method B, which was then subjected to oxidative conditions via General Method C to afford the 1,4-diketone 18a as a 20:1 mixture of diastereomers that was purified by flash chromatography (23.5 mg, 0.083 mmol, 50% yield over two steps): $[\alpha]_D$=−17.6 (c 0.19, CHCl$_3$); IR (Germanium ATR): 2922, 1659, 1366, 903 cm$^{-1}$; $^1$H NMR (500 MHz, Chloroform-d) δ 6.69-6.65 (m, 1H), 6.63 (dt, J=6.1, 1.9 Hz, 1H), 5.59 (dt, J=17.1, 9.8 Hz, 1H), 5.15-5.05 (m, 2H), 4.82 (d, J=1.3 Hz, 2H), 3.46 (td, J=12.3, 4.8 Hz, 1H), 3.41-3.29 (m, 1H), 2.63 (dd, J=14.7, 10.9 Hz, 1H), 2.43-2.14 (m, 5H), 1.75 (ddt, J=3.9, 2.7, 1.3 Hz, 6H), 1.69-1.62 (m, 3H); $^{13}$C NMR (126 MHz, CDCl$_3$) δ 200.4, 199.7, 145.8, 143.1, 142.4, 140.9, 136.0, 135.7, 117.3, 114.6, 50.8, 49.3, 33.1, 31.7, 18.7, 18.7, 16.2, 16.2, 16.2; HRMS (ESI): Exact mass calc'd for C$_{19}$H$_{25}$O$_2$ [M+H]$^+$, 285.1855. Found 285.1853.

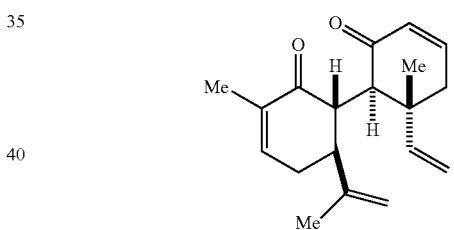

Compound 20a:

Enones (S)-7 (56.0 mg, 0.37 mmol) and 4 (50.0 mg, 0.37 mmol) were converted to the silyl bis-enol ether according to General Method B, which was subjected to oxidative conditions via General Method C to afford the crude 1,4-diketone 20a as a 10:1 mixture of diastereomers that were separated by flash chromatography (major diastereomer: 44.6 mg, 0.16 mmol, 42% yield over two steps, total coupled yield: 49.2 mg, 0.17 mmol, 47% over two steps): $[\alpha]_D$= −62.9 (c 0.17, CHCl$_3$); IR (Germanium ATR): 2924, 1698, 1641, 1279, 849 cm$^{-1}$; $^1$H NMR (500 MHz, Chloroform-d) δ 6.80 (ddd, J=10.1, 6.4, 2.4 Hz, 1H), 6.63 (ddd, J=6.2, 2.6, 1.4 Hz, 1H), 6.07 (dd, J=10.1, 2.9 Hz, 1H), 5.70 (dd, J=17.3, 10.8 Hz, 1H), 5.12-5.10 (m, 1H), 5.08 (dd, J=9.7, 1.0 Hz, 1H), 4.89 (p, J=1.7 Hz, 1H), 4.84-4.82 (m, 1H), 3.23 (td, J=12.1, 4.7 Hz, 1H), 2.61 (s, 1H), 2.46-2.35 (m, 3H), 2.32-2.23 (m, 1H), 2.14 (dd, J=18.1, 6.4 Hz, 1H), 1.77 (dt, J=2.7, 1.3 Hz, 3H), 1.68 (t, J=1.1 Hz, 3H), 1.20 (s, 3H); $^{13}$C NMR (126 MHz, CDCl$_3$) δ 199.3, 198.1, 147.5, 146.0, 146.0, 142.1, 136.0, 130.4, 115.4, 114.0, 54.9, 50.4, 49.2, 44.2, 40.5, 31.2, 19.7, 19.2, 16.6; HRMS (ESI): Exact mass calc'd for C$_{19}$H$_{25}$O$_2$ [M+H]$^+$, 285.1855. Found 285.1853.

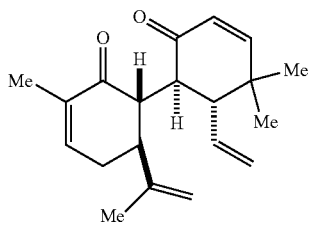 [SMILES: C=C[C@@H]1[C@@H]([C@H]2C(=O)C(C)=CC[C@@H]2C(=C)C)C(=O)C=CC1(C)C]

Compound 21a:

Enones (S)-7 (62.0 mg, 0.41 mmol) and 5 (62.0 mg, 0.41 mmol) were converted to the silyl bis-enol ether according to General Method B, which was then subjected to oxidative conditions via General Method C to afford 1,4-diketone 21a as a 20:1 mixture of diastereomers that was purified by flash chromatography (71.9 mg, 0.24 mmol, 59% yield over two steps): $[\alpha]_D$=+24.7 (c 1.10, $CHCl_3$); IR (Germanium ATR): 2962, 1662, 1376, 1364, 921, 894 $cm^{-1}$; $^1H$ NMR (500 MHz, Chloroform-d) δ 6.68-6.61 (m, 1H), 6.56 (d, J=10.1 Hz, 1H), 5.82 (d, J=10.0 Hz, 1H), 5.53 (dt, J=17.1, 10.3 Hz, 1H), 5.20 (d, J=10.1 Hz, 1H), 5.13-5.05 (m, 1H), 4.83 (t, J=4.2 Hz, 2H), 3.49 (td, J=12.6, 4.8 Hz, 1H), 3.17 (t, J=11.5 Hz, 1H), 2.55 (d, J=13.0 Hz, 1H), 2.49 (d, J=12.6 Hz, 1H), 2.40-2.20 (m, 2H), 1.75-1.71 (m, 3H), 1.65 (s, 3H), 1.07 (s, 3H), 0.99 (s, 3H); $^{13}C$ NMR (126 MHz, $CDCl_3$) δ 200.4, 200.0, 158.4, 145.7, 143.3, 136.9, 135.6, 126.9, 120.1, 114.6, 53.8, 49.7, 48.9, 45.6, 36.3, 31.7, 28.6, 20.7, 18.7, 16.0; HRMS (ESI): Exact mass calc'd for $C_{20}H_{27}O_2$ $[M+H]^+$, 299.2011. Found 299.2014.

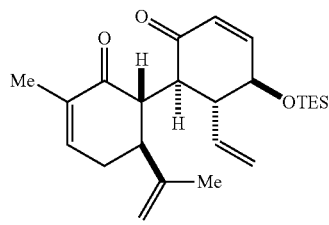

Compound 22a.

Enones (S)-7 (120.2 mg, 0.80 mmol) and 10 (201.9 mg, 0.80 mmol) were converted to the silyl bis-enol ether according to General Method B, which was then subjected to oxidative conditions via General Method C to afford 1,4-diketone 22a as a 20:1 mixture of diastereomers that was purified by flash chromatography (171.6 mg, 0.43 mmol, 54% over two steps): $[\alpha]_D$=−62.8 (c 1.69, $CHCl_3$); IR (Germanium ATR): 2954, 2913, 2876, 1666, 1381, 1087, 843, 725 $cm^{-1}$; $^1H$ NMR (500 MHz, Chloroform-d) δ 6.71 (dd, J=10.3, 1.7 Hz, 1H), 6.69-6.63 (m, 1H), 5.90 (dd, J=10.2, 2.3 Hz, 1H), 5.45 (dt, J=16.9, 10.0 Hz, 1H), 5.24-5.12 (m, 2H), 4.83 (s, 2H), 4.28 (dt, J=9.7, 2.1 Hz, 1H), 3.48 (s, 1H), 3.35 (s, 1H), 2.66-2.55 (m, 1H), 2.41-2.19 (m, 3H), 1.74 (d, J=2.4 Hz, 3H), 1.66 (s, 3H), 0.95 (t, J=7.9 Hz, 9H), 0.61 (q, J=8.1 Hz, 6H); $^{13}C$ NMR (126 MHz, $CDCl_3$) δ 199.9, 198.9, 152.3, 145.6, 143.3, 138.2, 135.6, 128.7, 120.4, 114.8, 71.5, 55.0, 49.5, 48.6, 47.9, 31.7, 18.8, 16.1, 7.0, 5.2; HRMS (ESI): Exact mass calc'd for $C_{24}H_{36}O_3SiNa$ $[M+Na]^+$, 423.2331. Found 423.2340.

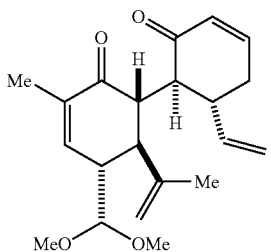 [SMILES: C=C[C@H]1CC=CC(=O)[C@@H]1[C@H]1C(=O)C(C)=C[C@@H](C(OC)OC)[C@@H]1C(=C)C]

Compound 23a.

Enones 9 (184 mg, 0.82 mmol) and (S)-1 (100 mg, 0.82 mmol) were converted to the silyl bis-enol ether according to General Method B, which was then subjected to oxidative conditions via General Method C to afford 1,4-diketone 23a as a 20:1 mixture of diastereomers that was purified by flash chromatography (163.0 mg, 0.473 mmol, 58% yield over two steps): $[\alpha]_D$=−47.0 (c 1.41, $CHCl_3$); IR (Germanium ATR): 2925, 1663, 1383, 1138, 1061, 752 $cm^{-1}$; $^1H$ NMR (500 MHz, Chloroform-d) δ 6.89-6.78 (m, 2H), 5.98 (dd, J=10.1, 2.8 Hz, 1H), 5.63-5.49 (m, 1H), 5.09 (dd, J=14.3, 8.3 Hz, 2H), 4.94 (s, 1H), 4.88 (d, J=2.2 Hz, 1H), 4.18 (d, J=2.7 Hz, 1H), 3.52-3.32 (m, 8H), 2.66 (dq, J=11.5, 2.6 Hz, 1H), 2.59 (d, J=12.9 Hz, 1H), 2.38 (dt, J=18.6, 5.5 Hz, 1H), 2.31-2.14 (m, 2H), 1.81-1.70 (m, 3H), 1.66 (s, 3H); $^{13}C$ NMR (126 MHz, $CDCl_3$) δ 199.8, 199.2, 147.2, 143.3, 142.5, 140.6, 135.9, 130.5, 117.7, 116.9, 106.1, 57.3, 56.2, 50.5, 50.2, 48.6, 45.3, 44.1, 33.1, 18.5, 16.1; HRMS (ESI): Exact mass calc'd for $C_{21}H_{29}O_4$ $[M+H]^+$, 345.2066. Found 345.2063.

Compound 24a.

Enones (R)-7 (75 mg, 0.50 mmol) and 11 (68 mg, 0.50 mmol) were converted to the silyl bis-enol ether according to General Method B, which was then subjected to oxidative conditions via General Method C to afford 1,4-diketone 24a as a 20:1 mixture of diastereomers that was purified by flash chromatography (80.5 mg, 0.28 mmol, 57% yield). While most coupled products were oils, for 24a, solid crystals suitable for x-ray crystallography were obtained by slow diffusion of hexane in ethyl acetate. $[\alpha]_D$=−47.4 (c 1.24, $CHCl_3$); IR (Germanium ATR): 3075, 2922, 1657, 1431, 909 $cm^{-1}$; $^1H$ NMR (500 MHz, Chloroform-d) δ 6.78 (dt, J=10.1, 3.9 Hz, 1H), 6.55 (ddt, J=4.7, 3.1, 1.4 Hz, 1H), 5.96 (dt, J=10.1, 2.0 Hz, 1H), 5.75 (dddd, J=16.5, 11.0, 8.2, 6.1 Hz, 1H), 5.05 (d, J=1.3 Hz, 1H), 5.03-4.99 (m, 1H), 4.69 (p, J=1.5 Hz, 1H), 4.66 (d, J=1.3 Hz, 1H), 2.94 (d, J=2.1 Hz, 1H), 2.86 (dd, J=7.4, 2.1 Hz, 1H), 2.66 (ddt, J=20.6, 7.4, 2.8 Hz, 1H), 2.60 (ddt, J=14.0, 6.1, 1.5 Hz, 1H), 2.36-2.28 (m, 3H), 2.28-2.15 (m, 2H), 1.98 (dt, J=14.2, 6.2 Hz, 1H), 1.76 (q, J=1.8 Hz, 3H), 1.70-1.66 (m, 3H); $^{13}C$ NMR (126 MHz, $CDCl_3$) δ 200.4, 200.0, 149.0, 147.3, 142.5, 136.8, 134.2, 129.8, 118.6, 111.6, 52.4, 52.1, 41.4, 38.1, 29.6, 29.5, 23.2, 21.2, 16.5; HRMS (ESI): Exact mass calc'd for $C_{19}H_{25}O_2$

[M+H]+, 285.1855. Found 285.1852. The structure of the compound was confirmed by x-ray diffraction analysis.

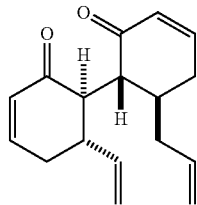 [SMILES: C=CC[C@@H]1CC=CC(=O)[C@H]1[C@@H]1C(=O)C=CC[C@H]1C=C]

Compound 25a.

Enones 6 (91.0 mg, 0.66 mmol) and (R)-1 (82.0 mg, 0.66 mmol) were converted to the silyl bis-enol ether according to General Method B, which was then subjected to oxidative conditions via General Method C to afford the crude 1,4-diketone 25a as a 5:1 mixture of diastereomers that were separated by flash chromatography. The major NMR of the major diastereomer shows a small amount of S12 which could not be separated, however both compounds converge to the coupled product 25 in the RCM (major diastereomer: 70.8 mg, 0.28 mmol, 42% over two steps; total coupled yield: 86.2 mg, 0.34 mmol, 51% over two steps): $[\alpha]_D$=−5.4 (c 1.20, CHCl$_3$); IR (Germanium ATR): 3075, 2924, 1663, 1625, 1388, 915 cm$^{-1}$; $^1$H NMR (500 MHz, Chloroform-d) δ 7.00-6.83 (m, 2H), 6.05 (dddd, J=9.9, 5.3, 2.8, 1.0 Hz, 1H), 6.02-5.98 (m, 1H), 5.78-5.68 (m, 1H), 5.68-5.58 (m, 1H), 5.14-4.99 (m, 4H), 3.15 (s, 1H), 2.99 (d, J=10.7 Hz, 1H), 2.92-2.76 (m, 1H), 2.70-2.56 (m, 1H), 2.56-2.36 (m, 2H), 2.32 (ddt, J=18.7, 11.1, 2.7 Hz, 1H), 2.27-2.14 (m, 1H), 2.09 (tdt, J=18.9, 11.3, 2.7 Hz, 1H), 1.97 (dq, J=14.1, 8.4 Hz, 1H); $^{13}$C NMR (126 MHz, CDCl$_3$) δ 200.2, 199.5, 148.6, 148.1, 140.7, 135.6, 130.1, 129.9, 117.5, 117.2, 51.0, 49.1, 44.3, 38.5, 36.8, 33.3, 32.0; HRMS (ESI): Exact mass calc'd for C$_{17}$H$_{21}$O$_2$ [M+H]+, 257.1542. Found 257.1538.

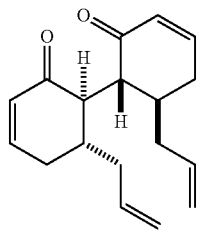 [SMILES: C=CC[C@@H]1CC=CC(=O)[C@H]1[C@@H]1C(=O)C=CC[C@H]1CC=C]

Compound S12.

Enone 6, (100 mg, 0.73 mmol) was converted to the silyl bis-enol ether according to General Method A, which was then subjected to oxidative conditions via General Method C to afford C2-symmetric 1,4-diketone S12 as a 5:1 mixture of diastereomers that could not be separated by flash chromatography (51.5 mg, 0.19 mmol, 52% yield over two steps, as a mixture of diastereomers): IR (Germanium ATR): 2923, 1663, 1640, 1388, 911 cm$^{-1}$; $^1$H NMR (500 MHz, Chloroform-d) δ 6.93 (ddd, J=10.0, 5.8, 2.6 Hz, 1H), 6.04 (ddd, J=10.0, 2.9, 1.0 Hz, 1H), 5.71 (dddd, J=16.6, 10.4, 8.1, 6.1 Hz, 1H), 5.12-4.99 (m, 2H), 2.98 (d, J=10.8 Hz, 1H), 2.56-2.48 (m, 1H), 2.48-2.38 (m, 1H), 2.18 (dddd, J=13.5, 5.5, 3.8, 1.7 Hz, 1H), 2.10 (ddt, J=18.6, 9.9, 2.7 Hz, 1H), 1.96 (dt, J=14.1, 8.7 Hz, 1H); $^{13}$C NMR (126 MHz, CDCl$_3$) δ 200.1, 148.5, 135.7, 129.7, 117.5, 50.2, 38.7, 36.6, 31.3; HRMS (ESI): Exact mass calc'd for C$_{18}$H$_{22}$O$_2$Na [M+Na]+, 293.1518. Found 293.1513.

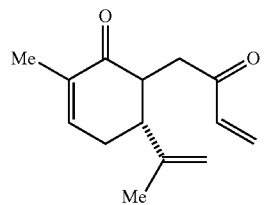 [SMILES: C=CC(=O)CC1C(=O)C(C)=CC[C@H]1C(=C)C]

Compound 27a.

Enones (R)-7 (157.7 mg, 1.05 mmol) and methylvinyl ketone 12 (73.6 mg, 85.2 μL, 1.05 mmol) were converted to the silyl bis-enol ether according to General Method B, which was then subjected to oxidative conditions via General Method C to afford 1,4-diketone 27a as a 1.5:1 mixture of diastereomers that could not be separated by flash chromatography (157 mg, 0.72 mmol, 69% yield over two steps, as a mixture of diastereomers): IR (Germanium ATR): 2922, 1665, 1614, 1400, 896 cm$^{-1}$; $^1$H NMR (499 MHz, Chloroform-d) δ 6.71 (dt, J=5.9, 1.9 Hz, 1H), 6.61 (d, J=4.0 Hz, 1H), 6.41 (ddd, J=17.6, 14.9, 10.6 Hz, 2H), 6.26 (t, J=1.2 Hz, 1H), 6.23 (d, J=1.2 Hz, 1H), 5.82 (ddd, J=10.6, 8.5, 1.1 Hz, 2H), 4.84-4.78 (m, 3H), 4.58 (dd, J=1.7, 0.9 Hz, 1H), 3.38 (q, J=6.1 Hz, 1H), 3.17 (dd, J=17.3, 6.4 Hz, 1H), 3.11 (ddd, J=13.3, 7.9, 3.2 Hz, 1H), 2.98-2.89 (m, 2H), 2.81-2.68 (m, 2H), 2.55-2.47 (m, 2H), 2.47-2.44 (m, 1H), 2.38 (dddd, J=19.2, 5.1, 3.5, 1.7 Hz, 1H), 2.34-2.26 (m, 1H), 1.77 (ddt, J=6.3, 2.7, 1.4 Hz, 6H), 1.69 (t, J=1.0 Hz, 3H), 1.61 (dd, J=1.5, 0.7 Hz, 3H); $^{13}$C NMR (126 MHz, CDCl$_3$) δ 200.2, 200.1, 199.3, 199.3, 145.5, 145.0, 143.8, 142.4, 136.9, 136.8, 135.3, 134.9, 128.3, 127.8, 114.3, 113.8, 48.7, 46.5, 45.6, 45.1, 37.4, 36.9, 31.5, 30.2, 22.2, 18.3, 16.2, 16.1; HRMS (ESI): Exact mass calc'd for C$_{14}$H$_{19}$O$_2$ [M+H]+, 219.1385. Found 219.1389.

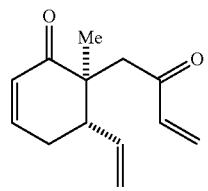

Compound 28a.

Enones 2 (75.0 mg, 0.55 mmol) methylvinyl ketone 12 (39.0 mg, 0.55 mmol) were converted to the silyl bis-enol ether according to General Method B, which was then subjected to oxidative conditions via General Method C to afford 1,4-diketone 28a as a 1.3:1 mixture of diastereomers that were separated by flash chromatography (major diastereomer: 32.7 mg, 0.16 mmol, 29% yield over two steps; total coupled yield: 56.6 mg, 0.28 mmol, 51% over two steps): $[\alpha]_D$=−16.6 (c 0.77, CHCl$_3$); IR (Germanium ATR): 2933, 1671, 1633, 1389, 921 cm$^{-1}$; $^1$H NMR (499 MHz, Chloroform-d) δ 6.90 (ddd, J=10.1, 5.6, 2.5 Hz, 1H), 6.31 (dd, J=17.6, 10.5 Hz, 1H), 6.19 (dd, J=17.6, 1.2 Hz, 1H), 6.05 (ddd, J=10.1, 2.9, 1.2 Hz, 1H), 5.82-5.70 (m, 1H), 5.76 (dd, J=10.5, 1.2 Hz, 1H), 5.10 (dd, J=10.3, 1.8 Hz, 1H), 5.02 (ddd, J=17.0, 1.8, 0.9 Hz, 1H), 3.37-3.27 (m, 1H), 3.21 (d, J=18.0 Hz, 1H), 2.73 (d, J=18.0 Hz, 1H), 2.39 (ddt, J=19.2, 11.0, 2.6 Hz, 1H), 2.35-2.28 (m, 1H), 1.03 (s, 3H); $^{13}$C NMR (126 MHz, CDCl$_3$) δ 202.4, 198.2, 147.5, 137.2, 136.7, 128.6, 127.8, 118.2, 46.8, 45.0, 43.5, 29.1, 18.3; HRMS (ESI): Exact mass calc'd for C$_{13}$H$_{17}$O$_2$ [M+H]+, 205.1229. Found 205.1210.

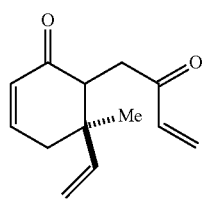

Compound 29a.

Enones 4 (90.0 mg, 0.66 mmol) and methylvinyl ketone 12 (46.0 mg, 0.66 mmol) were converted to the silyl bis-enol ether according to General Method B, which was then subjected to oxidative conditions via General Method C to afford 1,4-diketone 29a as a 1.6:1 mixture of diastereomers that could not be separated by flash chromatography (76.1 mg, 0.37 mmol, 56% yield over two steps, as a mixture of diastereomers): IR (Germanium ATR): 2971, 1674, 1641, 1387, 1279, 851 cm$^{-1}$; $^1$H NMR (499 MHz, Chloroform-d) δ 6.81 (ddt, J=10.1, 5.9, 2.1 Hz, 2H), 6.42 (ddd, J=17.6, 10.6, 5.8 Hz, 2H), 6.26 (ddd, J=17.6, 7.2, 1.0 Hz, 2H), 6.09-6.00 (m, 2H), 5.88-5.74 (m, 4H), 5.12-4.96 (m, 4H), 3.36 (dd, J=8.6, 3.1 Hz, 1H), 3.31 (dd, J=7.0, 4.3 Hz, 1H), 3.19 (dd, J=17.4, 7.0 Hz, 1H), 3.08 (dd, J=17.2, 8.6 Hz, 1H), 2.62 (ddt, J=24.3, 18.9, 2.8 Hz, 2H), 2.41-2.38 (m, 1H), 2.35 (td, J=5.6, 4.9, 3.7 Hz, 1H), 2.25 (dd, J=17.2, 3.0 Hz, 1H), 2.17 (dd, J=19.0, 5.9 Hz, 1H), 1.14 (s, 3H), 1.01 (s, 3H); $^{13}$C NMR (126 MHz, CDCl$_3$) δ 199.3, 199.2, 199.1, 199.0, 146.6, 146.5, 145.6, 140.1, 136.7, 136.7, 129.2, 128.9, 128.1, 127.9, 115.2, 113.9, 52.3, 51.1, 43.6, 43.2, 40.4, 40.0, 34.6, 34.4, 25.7, 16.7; HRMS (ESI): Exact mass calc'd for C$_{13}$H$_{17}$O$_2$ [M+H]$^+$, 205.1229. Found 205.1224.

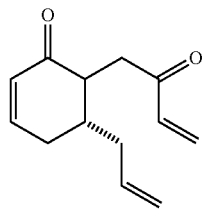

Compound 30a.

Enones 6 (91.0 mg, 0.67 mmol) and methylvinyl ketone 12 (47.0 mg, 0.67 mmol) were converted to the sily bis-enol ether according to General Method B, which was then subjected to oxidative conditions via General Method C to afford 1,4-diketone 30a as a 1.3:1 mixture of diastereomers that could not be separated by flash chromatography (76.0 mg, 0.37 mmol, 56% yield over two steps, as a mixture of diastereomers): IR (Germanium ATR): 3076, 2922, 1673, 1641, 1390, 917 cm$^{-1}$; $^1$H NMR (500 MHz, Chloroform-d) δ 6.98-6.89 (m, 1H), 6.79 (dddd, J=9.7, 5.6, 2.6, 1.2 Hz, 1H), 6.43 (ddd, J=17.7, 10.6, 1.4 Hz, 2H), 6.28 (ddd, J=17.7, 10.4, 1.0 Hz, 2H), 6.03 (dtd, J=10.1, 3.0, 1.1 Hz, 2H), 5.86 (ddd, J=11.9, 10.5, 1.0 Hz, 2H), 5.79-5.58 (m, 2H), 5.12-4.93 (m, 4H), 3.41 (td, J=6.3, 4.3 Hz, 1H), 3.28 (dd, J=17.2, 6.9 Hz, 1H), 3.14 (dd, J=17.3, 5.7 Hz, 1H), 2.89 (dt, J=11.2, 5.4 Hz, 1H), 2.74 (dd, J=17.3, 5.2 Hz, 1H), 2.61 (ddt, J=19.3, 5.6, 2.9 Hz, 1H), 2.51-2.38 (m, 4H), 2.35-2.26 (m, 1H), 2.26-2.19 (m, 1H), 2.18-2.00 (m, 3H), 1.93 (ddd, J=14.2, 10.9, 8.4 Hz, 1H); $^{13}$C NMR (126 MHz, CDCl$_3$) δ 199.9, 199.5, 198.9, 198.9, 149.0, 147.1, 136.7, 136.6, 136.6, 135.1, 129.6, 129.1, 128.5, 128.2, 117.8, 117.2, 48.3, 47.2, 38.4, 38.0, 38.0, 36.8, 36.6, 32.0, 31.6, 30.1; HRMS (ESI): Exact mass calc'd for C$_{13}$H$_{17}$O$_2$ [M+H]$^+$, 205.1229. Found 205.1212.

Oxidative Coupling Control Experiment:

Scheme S14. Oxidative dimerization of enone 8 without the silicon tether.

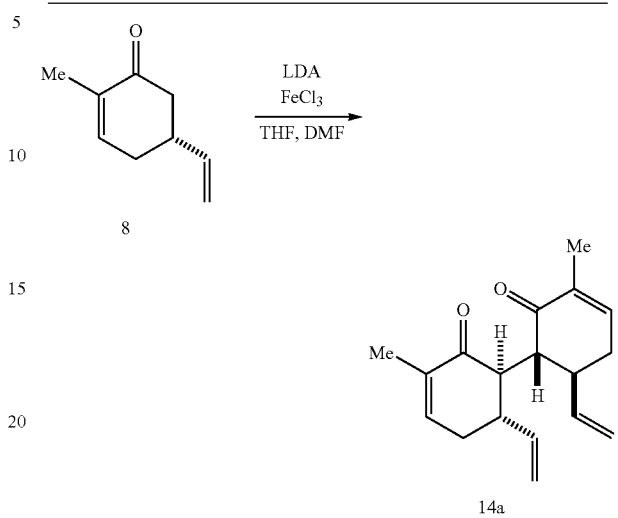

This oxidative coupling procedure was carried under conditions developed by Frazier and Harlow.[12] A solution of LDA was prepared by adding freshly distilled diisopropylamine (68 µL, 0.48 mmol, 1.3 equiv.) to a flame dried round-bottom flask and diluting with THF (0.4 mL). The solution was cooled to −78° C., and n-BuLi (0.23 mL, 1.99 M, 0.45 mmol, 1.2 equiv.) was added. After 10 minutes at this temperature, enone 8 (50 mg, 0.37 mmol) in THF (0.4 mL) was added via cannula (with an additional 0.1 mL THF rinse). The reaction stirred at this temperature for 30 minutes before adding FeCl$_3$ (80 mg, 0.49 mmol, 1.3 equiv.) in DMF (0.4 mL) via cannula (with an additional 0.1 mL DMF rinse). The reaction warmed to room temperature. After stirring for 15 hours, the reaction was quenched with 1 M HCl and extracted with 10% ether/pentane. The combined organic layers were dried over MgSO$_4$. The diastereoselectivity of the reaction was determined from the crude $^1$H NMR spectrum to be 3:1 14a to the minor diastereomer. The crude material was purified by flash chromatography on silica gel with 5% EtOAc/hexanes (23.8 mg major product 14a, 0.088 mmol, 48%; 8.1 mg minor diastereomer, 0.03 mmol, 16%; 31.9 mg total, 0.12 mmol, 64% combined yield). This result is compared to the observed 20:1 diastereoselectivity and 68% yield over two steps when employing the designed silicon tether approach.

4. Ring-Closing Metathesis Experimental Procedures and Characterization Data

Scheme S15. General method D for the ring-closing metathesis of the coupled products.

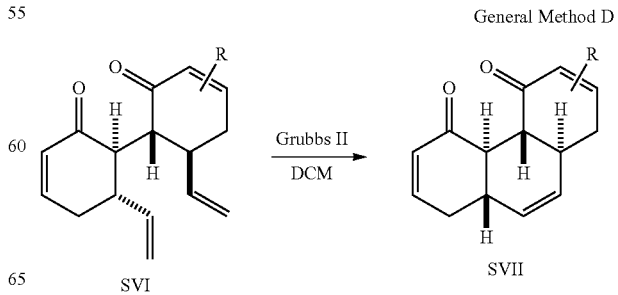

General Method D:

To a flame-dried flask was added Grubbs II from the glove box (10 mol %). SVI in DCM (0.05 M) was added to the flask via cannula and the reaction stirred at room temperature under $N_2$. Where noted below, when forming a trisubstituted olefin or a larger, more challenging ring system through the RCM, the reaction was heated to reflux at 40° C. Upon observed consumption of the starting material by TLC (5-15 h), DMSO (10 μL) was added, and the mixture stirred for 2 h-12 h. The solvent was evaporated, and the crude material was purified by flash chromatography on silica gel with 20% EtOAc/hexanes to yield couple & close product SVII.

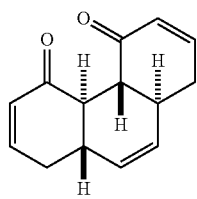

Compound 13.

Coupled product 13a (105.5 mg, 0.44 mmol) was submitted to ring-closing metathesis conditions according to General Method D to afford 13 (81.4 mg, 0.38 mmol, 86% yield). Solid crystals for x-ray crystallography were obtained by slow evaporation of ethyl acetate. IR (Germanium ATR): 3028, 2876, 1685, 1378, 793 cm$^{-1}$; $^1$H NMR (499 MHz, Chloroform-d) δ 6.79 (ddd, J=10.1, 5.2, 2.3 Hz, 1H), 6.08 (ddd, J=10.1, 3.2, 0.9 Hz, 1H), 5.56 (d, J=0.8 Hz, 1H), 2.74-2.69 (m, 1H), 2.61-2.47 (m, 2H), 2.26 (dddd, J=18.4, 11.1, 3.2, 2.2 Hz, 1H). $^{13}$C NMR (126 MHz, CDCl$_3$) δ 199.7, 145.4, 130.7, 128.9, 46.7, 38.8, 34.3; HRMS (ESI): Exact mass calc'd for $C_{14}H_{15}O_2$ [M+H]$^+$, 215.1072. Found 215.1070. The structure of the compound was confirmed by x-ray diffraction analysis.

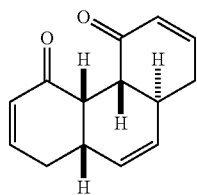

Compound Epi-13.

Coupled product epi-13a (24.6 mg, 0.100 mmol) was submitted to ring-closing metathesis conditions according to General Method D to afford epi-13 (17.9 mg, 0.084 mmol, 84% yield). Solid crystals for x-ray crystallography were obtained by slow evaporation of ethyl acetate. [α]$_D$=−2.2 (c 0.56, CHCl$_3$); IR (Germanium ATR): 3015, 2918, 1670, 1390, 867 cm$^{-1}$; $^1$H NMR (500 MHz, Chloroform-d) δ 6.97 (ddd, J=10.2, 6.1, 2.1 Hz, 1H), 6.72 (ddd, J=10.1, 5.9, 2.4 Hz, 1H), 6.16 (dd, J=10.1, 2.8 Hz, 1H), 5.93 (dd, J=10.1, 3.0 Hz, 1H), 5.62 (dt, J=9.9, 2.5 Hz, 1H), 5.48 (dq, J=9.9, 2.9, 1.5 Hz, 1H), 3.59 (dd, J=5.4, 2.5 Hz, 1H), 3.14-3.05 (m, 1H), 2.93-2.77 (m, 2H), 2.51 (ddd, J=18.2, 6.2, 4.3 Hz, 1H), 2.41 (dd, J=19.2, 5.6 Hz, 1H), 2.20-2.04 (m, 2H); $^{13}$C NMR (126 MHz, CDCl$_3$) δ 197.7, 197.4, 148.2, 145.8, 132.4, 131.1, 130.4, 129.5, 51.2, 43.5, 36.6, 34.2, 32.5, 31.6; HRMS (ESI): Exact mass calc'd for $C_{14}H_{15}O_2$ [M+H]$^+$, 215.1072. Found 215.1070. The structure of the compound was confirmed by x-ray diffraction analysis.

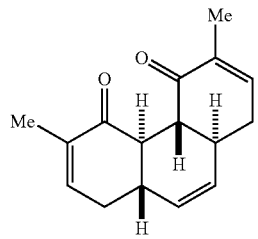

Compound 14.

Coupled product 14a (20.0 mg, 0.074 mmol) was submitted to ring-closing metathesis conditions according to General Method D to afford 14 (15.1 mg, 0.062 mmol, 84% yield). Solid crystals for x-ray crystallography were obtained by slow evaporation of ethyl acetate. IR (Germanium ATR): 3019, 2920, 1677, 1690, 1357, 908 cm$^{-1}$; $^1$H NMR (500 MHz, Chloroform-d) δ 6.50 (qd, J=3.4, 2.9, 1.4 Hz, 1H), 5.52 (s, 1H), 2.68-2.61 (m, 1H), 2.56-2.38 (m, 2H), 2.21 (ddt, J=18.1, 11.1, 2.6 Hz, 1H), 1.83 (dt, J=2.6, 1.4 Hz, 3H); $^{13}$C NMR (126 MHz, CDCl$_3$) δ 200.8, 139.8, 137.0, 129.1, 46.7, 39.0, 34.2, 16.1. HRMS (ESI): Exact mass calc'd for $C_{16}H_{19}O_2$ [M+H]$^+$, 243.1385. Found 243.1375. The structure of the compound was confirmed by x-ray diffraction analysis.

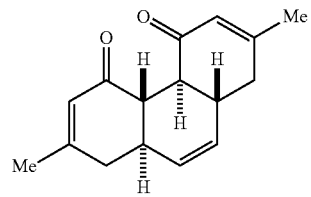

Compound 15.

Coupled product 15a (16.8 mg, 0.062 mmol) was submitted to ring-closing metathesis conditions according to General Method D to afford 15 (9.7 mg, 0.040 mmol, 65% yield): IR (Germanium ATR): 2914, 1676, 1627, 1379, 834 cm$^{-1}$; $^1$H NMR (500 MHz, Chloroform-d) δ 5.91 (dd, J=2.7, 1.4 Hz, 1H), 5.54 (s, 1H), 2.67-2.55 (m, 1H), 2.51 (td, J=10.6, 8.5, 3.8 Hz, 1H), 2.37 (dd, J=17.9, 3.8 Hz, 1H), 2.25 (ddt, J=17.8, 11.2, 2.7, 1.4 Hz, 1H), 1.93 (d, J=1.4 Hz, 3H); $^{13}$C NMR (126 MHz, CDCl$_3$) δ 199.4, 156.8, 129.0, 127.3, 46.2, 39.4, 38.5, 23.6; HRMS (ESI): Exact mass calc'd for $C_{16}H_{19}O_2$ [M+H]$^+$, 243.1385. Found 243.1374.

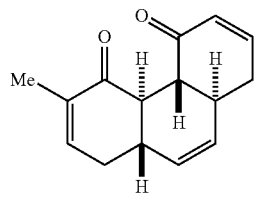

Compound 16.

Coupled product 16a (15.0 mg, 0.059 mmol) was submitted to ring-closing metathesis conditions according to General Method D to afford 16 (11.5 mg, 0.050 mmol, 86% yield): [α]$_D$=−615.6 (c 0.39, CHCl$_3$); IR (Germanium ATR): 2920, 1681, 1352, 1041 cm$^{-1}$; $^1$H NMR (500 MHz, Chloroform-d) δ 6.78 (ddd, J=10.1, 5.3, 2.2 Hz, 1H), 6.51 (dt, J=5.3, 1.9 Hz, 1H), 6.07 (dd, J=10.1, 3.0 Hz, 1H), 5.55-5.53 (m, 2H), 2.72 (t, J=12.1, 10.6 Hz, 1H), 2.64 (t, J=12.1, 10.6 Hz, 1H), 2.60-2.41 (m, 4H), 2.31-2.16 (m, 2H), 1.83 (dt, J=2.8, 1.5 Hz, 3H); $^{13}$C NMR (126 MHz, CDCl$_3$)$^{13}$C NMR (126 MHz, CDCl$_3$) δ 200.5, 200.0, 145.3, 139.9, 136.9, 130.7, 129.3, 128.7, 47.0, 46.5, 39.0, 38.9, 34.4, 34.2, 16.1; HRMS (ESI): Exact mass calc'd for C$_{15}$H$_{17}$O$_2$ [M+H]$^+$, 229.1229. Found 229.1215.

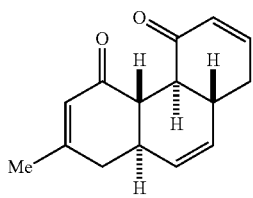

Compound 17.

Coupled product 17a (11.7 mg, 0.046 mmol) was submitted to ring-closing metathesis conditions according to General Method D to afford 17 (9.5 mg, 0.042 mmol, 91% yield): [α]$_D$=+582.4 (c 0.22, CHCl$_3$); IR (Germanium ATR): 2874, 1678, 1630, 1294, 821 cm$^{-1}$; $^1$H NMR (500 MHz, Chloroform-d) δ 6.78 (ddd, J=10.1, 5.4, 2.2 Hz, 1H), 6.08 (dd, J=10.1, 3.0 Hz, 1H), 5.91 (dd, J=2.6, 1.5 Hz, 1H), 5.65-5.49 (m, 2H), 2.76-2.44 (m, 5H), 2.38 (dd, J=18.0, 4.0 Hz, 1H), 2.26 (ddt, J=18.3, 11.1, 2.6 Hz, 2H), 2.00-1.88 (m, 3H); $^{13}$C NMR (126 MHz, CDCl$_3$) δ 199.9, 199.3, 157.0, 145.2, 130.8, 129.0, 128.9, 127.2, 46.9, 46.1, 39.4, 39.0, 38.3, 34.3, 23.7; HRMS (ESI): Exact mass calc'd for C$_{15}$H$_{17}$O$_2$ [M+H]$^+$, 229.1229. Found 229.1217.

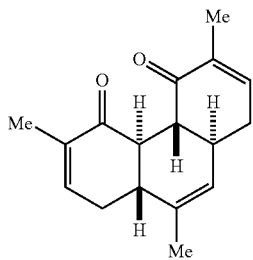

Compound 18.

Coupled product 18a (11.5 mg, 0.040 mmol) was submitted to ring-closing metathesis conditions according to General Method D with elevated temperature, refluxing at 40° C., to afford 18 (9.0 mg, 0.035 mmol, 87% yield): [α]$_D$=−488.1 (c 0.31, CHCl$_3$); IR (Germanium ATR): 2920, 1639, 1677, 1366, 863 cm$^{-1}$; $^1$H NMR (499 MHz, Chloroform-d) δ 6.53 (dq, J=5.7, 1.8 Hz, 1H), 6.50 (dq, J=5.1, 1.6 Hz, 1H), 5.25 (q, J=1.8 Hz, 1H), 2.73-2.57 (m, 3H), 2.50-2.32 (m, 3H), 2.16 (dddt, J=20.5, 16.1, 11.1, 2.5 Hz, 2H), 1.84 (dt, J=2.8, 1.5 Hz, 3H), 1.82 (dt, J=2.6, 1.4 Hz, 3H), 1.68 (dt, J=2.5, 1.3 Hz, 3H); $^{13}$C NMR (126 MHz, CDCl$_3$) δ 201.1, 201.1, 140.1, 139.9, 136.8, 136.8, 134.5, 124.9, 47.4, 46.6, 42.0, 38.6, 34.5, 32.4, 20.1, 16.1, 16.0; HRMS (ESI): Exact mass calc'd for C$_{17}$H$_{21}$O$_2$ [M+H]$^+$, 257.1542. Found 257.1532.

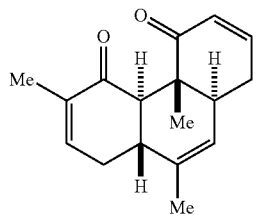

Compound 19.

Coupled product 19a (30.0 mg, 0.105 mmol) was submitted to ring-closing metathesis conditions according to General Method D with elevated temperature, refluxing at 40° C., to afford 19 (23.5 mg, 0.092 mmol, 87% yield): [α]$_D$=−93.3 (c 0.41, CHCl$_3$); IR (Germanium ATR): 2923, 1672, 1380, 910 cm$^{-1}$; $^1$H NMR (500 MHz, Chloroform-d) δ 6.60 (dt, J=10.2, 3.8 Hz, 1H), 6.52 (dq, J=5.7, 1.7 Hz, 1H), 5.92 (dt, J=10.2, 2.0 Hz, 1H), 5.11 (h, J=1.5 Hz, 1H), 2.73-2.62 (m, 1H), 2.65 (d, J=12.7 Hz, 1H), 2.58 (tq, J=8.2, 2.6 Hz, 1H), 2.46-2.36 (m, 1H), 2.26 (dd, J=3.4, 2.3 Hz, 1H), 2.24 (dd, J=3.8, 2.1 Hz, 1H), 2.16-2.04 (m, 1H), 1.82 (dt, J=2.8, 1.5 Hz, 3H), 1.69 (dt, J=2.6, 1.2 Hz, 3H), 1.27 (s, 3H); $^{13}$C NMR (126 MHz, CDCl$_3$) δ 203.5, 199.3, 143.4, 139.5, 137.2, 134.8, 128.7, 123.3, 52.1, 45.0, 42.3, 40.6, 32.3, 29.8, 20.1, 16.2, 9.9; HRMS (ESI): Exact mass calc'd for C$_{17}$H$_{21}$O$_2$ [M+H]$^+$, 257.1542. Found 257.1536.

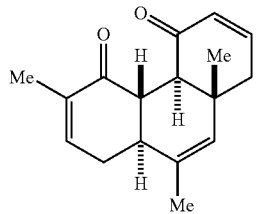

Compound 20.

Coupled product 20a (27.0 mg, 0.095 mmol) was submitted to ring-closing metathesis conditions according to General Method D with elevated temperature, refluxing at 40° C., to afford 20 (19.8 mg, 0.077 mmol, 81% yield): [α]$_D$=+531.9 (c 0.68, CHCl$_3$); IR (Germanium ATR): 2962, 1683, 1375, 722 cm$^{-1}$; $^1$H NMR (500 MHz, Chloroform-d) δ 6.63 (ddd, J=10.1, 5.5, 2.2 Hz, 1H), 6.52 (dq, J=5.4, 1.8 Hz, 1H), 6.08 (dd, J=10.1, 3.1 Hz, 1H), 5.29-5.23 (m, 1H), 2.89 (d, J=11.3 Hz, 1H), 2.73 (dd, J=12.5, 11.2 Hz, 1H), 2.63 (dddd, J=18.0, 5.6, 3.9, 1.6 Hz, 1H), 2.45 (dt, J=18.5, 2.8 Hz, 1H), 2.36-2.27 (m, 1H), 2.18 (ddd, J=18.8, 5.6, 0.9 Hz, 1H), 2.12 (ddt, J=16.0, 11.1, 2.5 Hz, 1H), 1.82 (dt, J=2.8, 1.4 Hz, 3H), 1.65 (t, J=1.3 Hz, 3H), 0.87 (s, 3H); $^{13}$C NMR (126 MHz, CDCl$_3$) δ 201.0, 199.9, 143.4, 139.9, 136.9, 131.8, 131.4, 131.1, 50.2, 44.9, 42.6, 41.3, 38.8, 32.4, 21.8, 20.1, 15.9; HRMS (ESI): Exact mass calc'd for C$_{17}$H$_{21}$O$_2$ [M+H]$^+$, 257.1542. Found 257.1539.

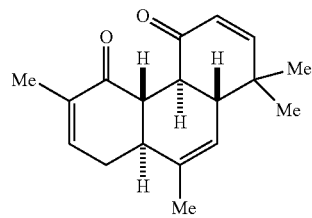

Compound 21.

Coupled product 21a (24.0 mg, 0.080 mmol) was submitted to ring-closing metathesis conditions according to General Method D with elevated temperature, refluxing at 40° C. As the reaction was proceeding much more slowly than for less hindered substrates, an additional 10 mol % Grubbs II was added after refluxing for 24 hours, and an additional 5 mol % Grubbs II after another 24 hours. The reaction was worked up after a total of 72 hours to afford 21 (14.8 mg, 0.055 mmol, 68% yield; also reisolating unreacted SM): $[\alpha]_D$=+288.2 (c 0.40, CHCl$_3$); IR (Germanium ATR): 2923, 1686, 1371, 1083, 700 cm$^{-1}$; $^1$H NMR (500 MHz, Chloroform-d) δ 6.54 (dt, J=5.5, 1.9 Hz, 1H), 6.39 (d, J=10.1 Hz, 1H), 5.88 (d, J=10.1 Hz, 1H), 5.40 (q, J=1.8 Hz, 1H), 2.86 (dd, J=12.6, 10.9 Hz, 1H), 2.73-2.61 (m, 2H), 2.40-2.32 (m, 2H), 2.12 (ddq, J=18.1, 11.0, 2.5 Hz, 1H), 1.84 (dt, J=2.9, 1.5 Hz, 3H), 1.72 (p, J=1.2 Hz, 3H), 1.18 (s, 3H), 1.03 (s, 3H); $^{13}$C NMR (126 MHz, CDCl$_3$) δ 201.1, 201.0, 156.1, 139.9, 136.8, 135.7, 126.7, 121.2, 47.2, 46.6, 41.5, 41.3, 37.9, 32.3, 27.6, 20.5, 19.6, 16.0; HRMS (ESI): Exact mass calc'd for C$_{18}$H$_{23}$O$_2$ [M+H]$^+$, 271.1698. Found 271.1696.

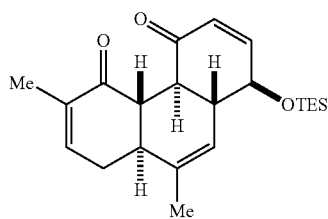

Compound 22.

Coupled product 22a, (80.1 mg, 0.20 mmol) was submitted to ring-closing metathesis conditions according to General Method D with elevated temperature, refluxing at 40° C. Just as with the reaction to form compound 21, this reaction was proceeding much more slowly than for less hindered substrates, so an additional 10 mol % Grubbs II was added after refluxing for 24 hours, and an additional 5 mol % Grubbs II added after 48 hours. The reaction was worked up after a total of 72 hours to afford 22 (46.9 mg, 0.13 mmol, 64%): $[\alpha]_D$=+261.8 (c 1.23, CHCl$_3$); IR (Germanium ATR): 2954, 2914, 2876, 1687, 1348, 1078, 835, 731 cm$^{-1}$; $^1$H NMR (500 MHz, Chloroform-d) δ 6.60 (dd, J=10.3, 1.8 Hz, 1H), 6.54 (dt, J=5.7, 1.9 Hz, 1H), 5.99 (dd, J=10.3, 2.3 Hz, 1H), 5.64 (d, J=2.0 Hz, 1H), 4.27 (dt, J=9.3, 2.1 Hz, 1H), 2.73-2.61 (m, 3H), 2.48 (ddd, J=11.7, 6.5, 2.3 Hz, 1H), 2.37-2.29 (m, 1H), 2.12 (ddt, J=18.2, 11.2, 2.5 Hz, 1H), 1.83 (dt, J=3.1, 1.5 Hz, 3H), 1.70 (dt, J=2.7, 1.3 Hz, 3H), 1.00 (t, J=8.0 Hz, 9H), 0.68 (q, J=8.0 Hz, 6H); $^{13}$C NMR (126 MHz, CDCl$_3$) δ 200.5, 199.5, 149.9, 140.1, 136.6, 135.1, 129.4, 121.1, 73.7, 47.8, 47.0, 45.0, 41.4, 32.2, 20.3, 15.9, 7.0, 5.1; HRMS (ESI): Exact mass calc'd for C$_{22}$H$_{32}$O$_3$SiNa [M+Na]$^+$, 395.2018. Found 395.2026.

Compound 23.

Coupled product 23a (52.0 mg, 0.15 mmol) was submitted to ring-closing metathesis conditions according to General Method D with elevated temperature, refluxing at 40° C. Just as with the reactions to form compounds 21 and 22, the reaction was proceeding much more slowly than for less hindered substrates, so an additional 10 mol % Grubbs II was added after refluxing for 24 hours. The reaction was worked up after a total of 65 hours to afford 23 (30.6 mg, 0.097 mmol, 64%): $[\alpha]_D$=+298.5 (c 0.95, CHCl$_3$); IR (Germanium ATR): 2922, 1684, 1378, 1119, 1059, 751 cm$^{-1}$; $^1$H NMR (499 MHz, Chloroform-d) δ 6.75 (ddd, J=10.2, 5.2, 2.2 Hz, 1H), 6.71-6.63 (m, 1H), 6.02 (dd, J=10.1, 3.0 Hz, 1H), 5.34 (q, J=1.8 Hz, 1H), 4.74 (d, J=2.7 Hz, 1H), 3.48 (s, 3H), 3.39 (s, 3H), 2.82-2.72 (m, 2H), 2.67 (t, J=11.7 Hz, 1H), 2.55 (t, J=11.3 Hz, 1H), 2.46 (dq, J=14.2, 4.5 Hz, 2H), 2.19 (ddt, J=19.2, 11.8, 2.7 Hz, 1H), 1.86 (p, J=1.7 Hz, 6H); $^{13}$C NMR (126 MHz, CDCl$_3$) δ 201.1, 200.1, 145.3, 139.1, 137.5, 134.3, 130.5, 128.3, 106.5, 56.8, 56.3, 48.6, 47.1, 46.8, 43.0, 38.1, 34.4, 24.9, 15.9; HRMS (ESI): Exact mass calc'd for C$_{19}$H$_{24}$O$_4$Na [M+Na]$^+$, 339.1572. Found 339.1569.

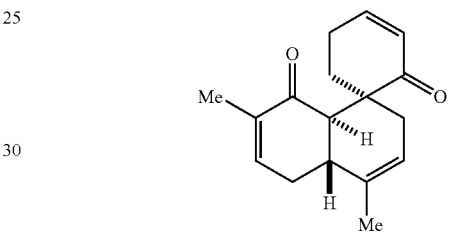

Compound 24.

Coupled product 24a (30.0 mg, 0.100 mmol) was submitted to ring-closing metathesis conditions according to General Method D with elevated temperature, refluxing at 40° C., to afford 24 (23.4 mg, 0.091 mmol, 91% yield): $[\alpha]_D$=−42.3 (c 1.04, CHCl$_3$); IR (Germanium ATR): 2920, 1668, 1381, 728 cm$^{-1}$; $^1$H NMR (500 MHz, Chloroform-d) δ 6.81 (ddt, J=9.7, 5.9, 1.8 Hz, 1H), 6.65 (dt, J=6.0, 1.8 Hz, 1H), 5.89 (dd, J=10.1, 2.9 Hz, 1H), 5.33-5.22 (m, 1H), 3.28 (t, J=12.4 Hz, 1H), 3.08 (td, J=12.6, 5.6 Hz, 1H), 2.72 (dddd, J=18.2, 5.7, 3.9, 1.5 Hz, 1H), 2.53-2.40 (m, 2H), 2.30 (dtt, J=19.3, 5.8, 1.5 Hz, 1H), 2.21 (d, J=12.3 Hz, 1H), 2.15 (dq, J=18.2, 2.8 Hz, 1H), 2.01 (ddt, J=18.3, 11.6, 2.5 Hz, 1H), 1.75 (dt, J=2.6, 1.4 Hz, 3H), 1.72-1.66 (m, 3H), 1.42 (ddt, J=12.9, 5.1, 1.6 Hz, 1H); $^{13}$C NMR (126 MHz, CDCl$_3$) δ 201.9, 200.2, 146.9, 142.3, 136.3, 135.2, 129.0, 117.6, 56.9, 42.4, 41.6, 36.1, 33.1, 32.5, 22.9, 20.5, 16.0; HRMS (ESI): Exact mass calc'd for C$_{17}$H$_{21}$O$_2$ [M+H]$^+$, 257.1542. Found 257.1534.

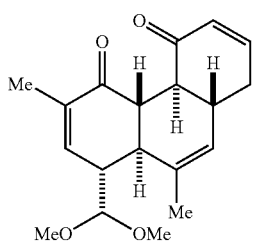

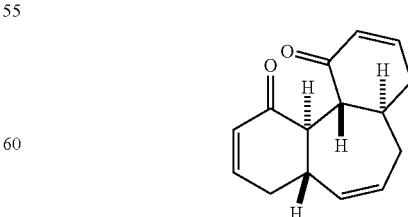

Compound 25.

Coupled product 25a (19.0 mg, 0.074 mmol) was submitted to ring-closing metathesis conditions according to

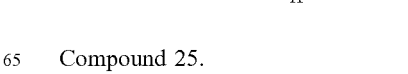

General Method D with elevated temperature, refluxing at 40° C., to afford 25 (12.2 mg, 0.053 mmol, 72% yield): $[\alpha]_D=-254.9$ (c 0.34, CHCl$_3$); IR (Germanium ATR): 3028, 2905, 1668, 1384, 795 cm$^{-1}$; $^1$H NMR (500 MHz, Chloroform-d) δ 6.85 (ddd, J=10.0, 4.9, 3.8 Hz, 1H), 6.77 (ddd, J=9.9, 5.5, 2.4 Hz, 1H), 6.08-5.99 (m, 2H), 5.96 (dddd, J=10.4, 8.4, 6.1, 2.2 Hz, 1H), 5.42 (dddd, J=10.3, 3.6, 2.2, 1.0 Hz, 1H), 3.18 (dd, J=12.9, 8.8 Hz, 1H), 3.07-2.95 (m, 2H), 2.59-2.50 (m, 2H), 2.44-2.21 (m, 3H), 1.99-1.85 (m, 2H); $^{13}$C NMR (126 MHz, CDCl$_3$) δ 200.8, 200.2, 146.6, 145.9, 134.4, 132.5, 129.8, 129.5, 53.9, 45.9, 39.6, 37.0, 36.8, 35.1, 33.3; HRMS (ESI): Exact mass calc'd for C$_{15}$H$_{17}$O$_2$ [M+H]$^+$, 229.1229. Found 229.1215.

Scheme S16. a) room temperature RCM of allyl dimer S12 leads to no reaction; b) RCM of S12 with elevated temperatures leads to alkene isomerization (S14) and the formation of 25; c) RCM of S12 with conditions developed to suppress alkene isomerization mediated by a ruthenium hydride species[13,14] led to no formation of 25, but also no formation of desired closed product S13, only slow decomposition of starting material; d) selective reduction of the enone functionality of S12 with Stryker's reagent leads to S15, which closes to form the desired (6,8,6)-system, 26.

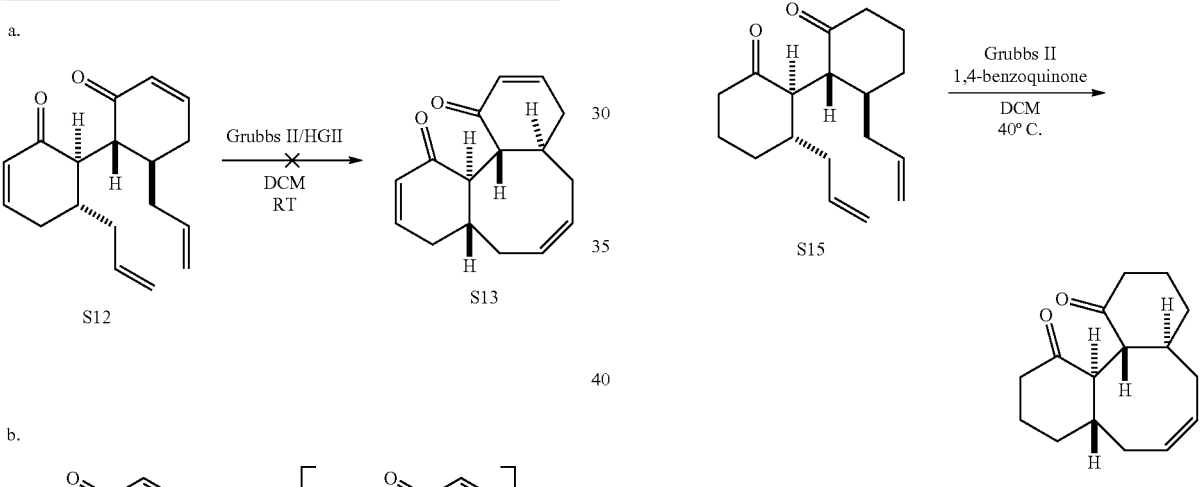

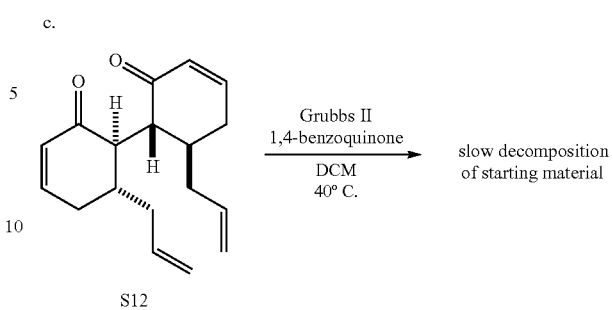

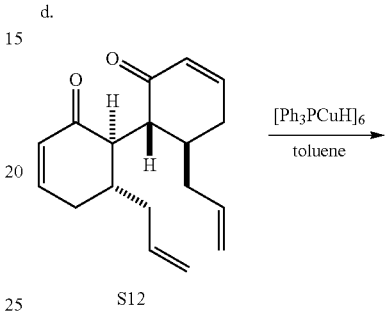

As shown in Scheme S16a, the RCM of S12 via General Method D at room temperature led to no formation of desired product S13 and only reisolation of starting material S12. Upon heating the reaction to 40° C., coupled product S12 formed the (6,7,6)-ring system 25 via undesired alkene isomerization (Scheme S16b). Grubbs and coworkers have reported that Grubbs II is capable of decomposing to a ruthenium hydride species that is implicated in olefin isomerization.[2,3] They disclosed various additives that were shown to prevent this unwanted isomerization, and 1,4-benzoquinone was successful in this case. Although these conditions did not allow for the successful RCM of coupled product S12 (Scheme S16c), after removal of the enone functionality to S15, these conditions were successful in forming the (6,8,6)-system, 26 (Scheme 516d).

[2]. Hong, S. H.; Day, M. W.; Grubbs, R. H. *J. Am. Chem. Soc.* 2004, 126, 7414-7415.

[3]. Hong, S. H.; Sanders, D. P.; Lee, C. W.; Grubbs, R. H. *J. Am. Chem. Soc.* 2005, 127, 17160-17161.

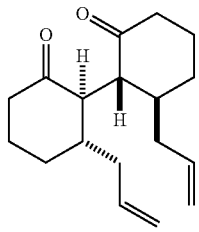

Compound S15.

Stryker's reagent (200.0 mg, 0.10 mmol, 0.8 equiv.) was added to a flame-dried round bottom flask from the glovebox. The flask was cooled to 0° C., and benzene (3 mL) that had been sparged with argon for 2 hours was added. S12 (35.0 mg, 0.13 mmol) in benzene (1 mL, with an additional 0.3 mL rinse) was added. The reaction was warmed to room temperature after 15 minutes and stirred overnight, after which the mixture was filtered through Celite with ether and concentrated. The crude material was purified by flash chromatography on silica gel with 5% EtOAc/hexane (32.2 mg, 0.12 mmol, 92% yield): IR (Germanium ATR): 2934, 1694, 1640, 1446, 995, 910 cm$^{-1}$; $^1$H NMR (500 MHz, Chloroform-d) δ 5.81-5.68 (m, 1H), 5.10-4.98 (m, 2H), 2.55-2.41 (m, 1H), 2.35 (d, J=9.9 Hz, 1H), 2.28-2.10 (m, 3H), 2.04-1.86 (m, 3H), 1.80 (dqd, J=16.9, 8.7, 7.8, 4.6 Hz, 1H), 1.31 (dtd, J=13.3, 11.3, 3.0 Hz, 1H); $^{13}$C NMR (126 MHz, CDCl$_3$) δ 211.6, 136.2, 117.1, 54.2, 41.6, 40.6, 39.3, 30.5, 23.6; HRMS (ESI): Exact mass calc'd for C$_{18}$H$_{26}$O$_2$Na [M+Na]$^+$, 297.1831. Found 297.1829.

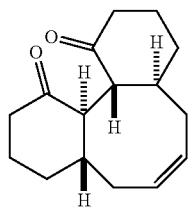

Compound 26.

Grubbs II (2.2 mg, 0.0026 mmol, 10 mol %) was added to a flame-dried round-bottom flask in the glove box. 1,4-benzoquinone (1.0 mg, 0.009 mmol, 35 mol %) was added and the flask was purged with N$_2$ for 2 minutes. DCM (1 mL) was added to the mixture. Compound S15 (7.0 mg, 0.026 mmol) in DCM (0.7 mL) was added to the flask (with an additional 0.3 mL DCM rinse) at room temperature, and the reaction was heated to 40° C. Upon observed consumption of the starting material by TLC (5.25 h), the reaction was cooled to room temperature and DMSO (10 µL) was added. After stirring at room temperature for 2 h, the solvent was evaporated. The crude material was purified by flash chromatography on silica gel with 10% EtOAc/hexane to afford 24 (4.9 mg, 0.020 mmol, 78% yield): IR (Germanium ATR): 2932, 1695, 1457, 1262, 909, 730 cm$^{-1}$; $^1$H NMR (499 MHz, Chloroform-d) δ 5.52 (t, J=3.5 Hz, 1H), 2.48 (d, J=15.7 Hz, 1H), 2.37-2.26 (m, 2H), 2.21-2.10 (m, 2H), 2.00-1.92 (m, 1H), 1.86 (q, J=13.2 Hz, 1H), 1.71 (d, J=13.7 Hz, 1H), 1.56-1.47 (m, 2H); $^{13}$C NMR (126 MHz, CDCl$_3$) δ 212.4, 128.5, 52.0, 42.0, 40.6, 35.4, 30.8, 24.1; HRMS (ESI): Exact mass calc'd for C$_{32}$H$_{45}$O$_4$ [2M+H]$^+$, 493.3318. Found 493.3311.

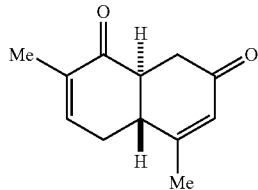 [SMILES: CC1=CC[C@H]2C(C)=CC(=O)C[C@@H]2C1=O]

Compound 27.

Coupled product 27a (40.0 mg, 0.183 mmol, 1.5:1 mixture of diastereomers) was submitted to ring-closing metathesis conditions according to General Method D with elevated temperature, refluxing at 40° C., to afford 27 as a 1.5:1 mixture of diastereomers that could be separated by flash chromatography (major diastereomer: 18.6 mg, 0.098 mmol, 53% yield; total yield: 34.4 mg, 0.180 mmol, 98%): [α]$_D$=−271.4 (c 0.10, CHCl$_3$); IR (Germanium ATR): 2922, 1661, 1379, 879 cm$^{-1}$; $^1$H NMR (499 MHz, Chloroform-d) δ 6.76 (ddq, J=4.7, 2.9, 1.3 Hz, 1H), 5.91 (t, J=1.3 Hz, 1H), 3.01 (dt, J=11.7, 4.9 Hz, 1H), 2.92 (dt, J=9.8, 5.1 Hz, 1H), 2.72-2.57 (m, 2H), 2.50-2.39 (m, 2H), 1.99 (d, J=1.3 Hz, 3H), 1.81 (q, J=1.3 Hz, 3H); $^{13}$C NMR (126 MHz, CDCl$_3$) δ 198.6, 196.6, 162.2, 142.6, 135.7, 127.5, 46.0, 39.7, 35.5, 27.3, 22.8, 16.1; HRMS (ESI): Exact mass calc'd for C$_{12}$H$_{15}$O$_2$ [M+H]$^+$, 191.1072. Found 191.1051.

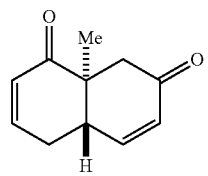 [SMILES: C[C@]12CC(=O)C=C[C@@H]1CC=CC2=O]

Compound 28.

Coupled product 28a (14.0 mg, 0.069 mmol) was submitted to ring-closing metathesis conditions according to General Method D to afford 28 (10.9 mg, 0.062 mmol, 90% yield): [α]$_D$=−61.8 (c 0.063, CHCl$_3$); IR (Germanium ATR): 2975, 1669, 1392, 824 cm$^{-1}$; $^1$H NMR (500 MHz, Chloroform-d) δ 6.94 (ddd, J=10.1, 5.7, 2.1 Hz, 1H), 6.62 (dd, J=10.0, 2.0 Hz, 1H), 6.08 (ddd, J=10.0, 3.1, 1.2 Hz, 1H), 6.03 (ddd, J=10.1, 2.9, 1.1 Hz, 1H), 3.06 (dddd, J=12.3, 5.0, 3.1, 2.0 Hz, 1H), 2.81 (dt, J=16.8, 0.9 Hz, 1H), 2.59 (dddt, J=19.1, 5.7, 4.8, 1.0 Hz, 1H), 2.48-2.33 (m, 2H), 1.09 (d, J=1.0 Hz, 3H); $^{13}$C NMR (126 MHz, CDCl$_3$) δ 201.4, 198.2, 148.3, 146.9, 130.0, 128.3, 47.3, 45.8, 41.0, 28.2, 15.4; HRMS (ESI): Exact mass calc'd for C$_{11}$H$_{13}$O$_2$ [M+H]$^+$, 177.0916. Found 177.0911.

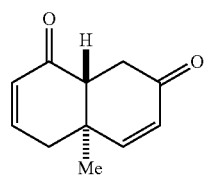 [SMILES: C[C@@]12C=CC(=O)C[C@H]1C(=O)C=CC2]

Compound 29.

Coupled product 29a (25.0 mg, 0.12 mmol, 1.6:1 mixture of diastereomers) was submitted to ring-closing metathesis conditions according to General Method D with elevated temperature, refluxing at 40° C., to afford 29 as a 1.6:1 mixture of diastereomers that could be separated by flash chromatography (major: 12.3 mg, 0.070 mmol, 58% yield; total yield: 19.8 mg, 0.11 mmol, 94%): [α]$_D$=+237.2 (c 0.34, CHCl$_3$); IR(Germanium ATR): 2967, 1670, 1387, 1244, 817 cm$^{-1}$; $^1$H NMR (500 MHz, Chloroform-d) δ 6.87 (ddd, J=10.2, 5.8, 2.3 Hz, 1H), 6.73 (d, J=10.0 Hz, 1H), 6.12 (dd, J=10.2, 3.1 Hz, 1H), 5.94 (dd, J=10.0, 1.0 Hz, 1H), 3.04 (dd, J=13.5, 4.2 Hz, 1H), 2.81 (dd, J=18.1, 4.2 Hz, 1H), 2.58 (dt, J=18.5, 2.9 Hz, 1H), 2.53-2.41 (m, 2H), 1.12 (s, 3H); $^{13}$C NMR (126 MHz, CDCl$_3$) δ 198.2, 197.5, 156.0, 145.7, 129.6, 127.9, 51.7, 39.0, 38.9, 33.4, 17.7; HRMS (ESI): Exact mass calc'd for C$_{11}$H$_{13}$O$_2$ [M+H]$^+$, 177.0916. Found 177.0911.

Compound 30.

Coupled product 30a (24.0 mg, 0.117 mmol, 1.3:1 mixture of diastereomers) was submitted to ring-closing metathesis conditions according to General Method D with elevated temperature, refluxing at 40° C., to afford 30 as a 1.3:1 mixture of diastereomers that could not be separated by flash chromatography (16.5 mg, 0.094 mmol, 80% yield as a mixture of inseparable diastereomers): IR (Germanium ATR): 2920, 1667, 1388, 825 cm$^{-1}$; $^1$H NMR (500 MHz, Chloroform-d) δ 6.98-6.86 (m, 2H), 6.62 (ddd, J=11.6, 6.9, 5.7 Hz, 1H), 6.50 (ddd, J=11.6, 7.2, 4.1 Hz, 1H), 6.08 (dddd, J=11.4, 5.6, 2.7, 1.2 Hz, 3H), 6.02 (dd, J=12.0, 2.6 Hz, 1H), 3.16 (ddd, J=15.6, 4.9, 1.0 Hz, 1H), 3.04-2.94 (m, 2H), 2.83 (dd, J=15.6, 6.9 Hz, 1H), 2.76-2.72 (m, 1H), 2.72-2.65 (m, 2H), 2.59 (dddd, J=13.2, 11.9, 6.1, 3.1 Hz, 2H), 2.53 (ddt, J=9.2, 4.1, 2.4 Hz, 1H), 2.50-2.39 (m, 3H), 2.37 (ddd, J=9.4, 4.4, 2.0 Hz, 1H), 2.33 (td, J=4.2, 1.4 Hz, 1H), 2.32-2.23 (m, 1H); $^{13}$C NMR (126 MHz, CDCl$_3$) δ 202.1, 201.8, 198.9, 198.0, 148.2, 147.9, 143.3, 142.5, 134.3, 133.0, 129.7, 129.6, 48.5, 45.7, 42.3, 40.5, 40.3, 37.6, 34.8, 33.7, 33.7, 32.7; HRMS (ESI): Exact mass calc'd for C$_{11}$H$_{13}$O$_2$ [M+H]$^+$, 177.0916. Found 177.0888.

5. Selective Functionalization of Prepared Scaffolds: Experimental Procedures and Characterization Data

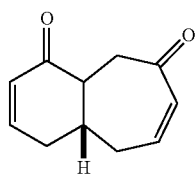 [SMILES: O=C1C=CC[C@@H]2CC=CC(=O)C2C1]

Scheme S17. Selective transformations of prepared scaffolds.

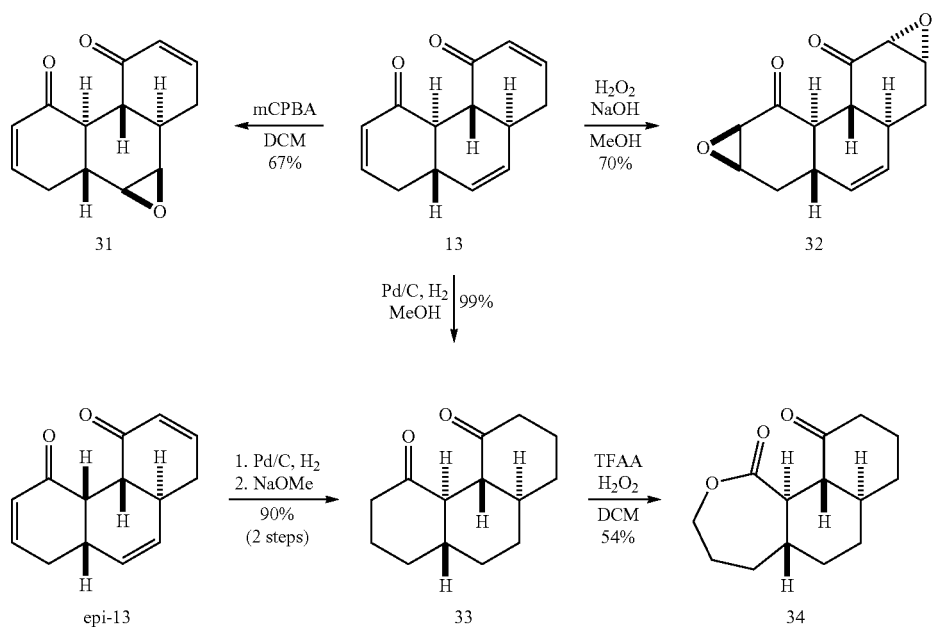

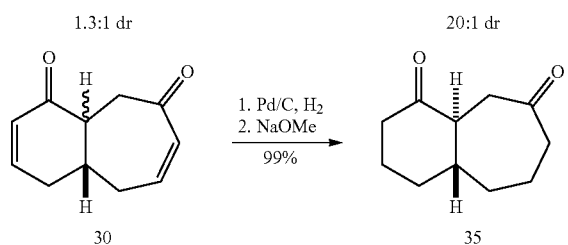

c.

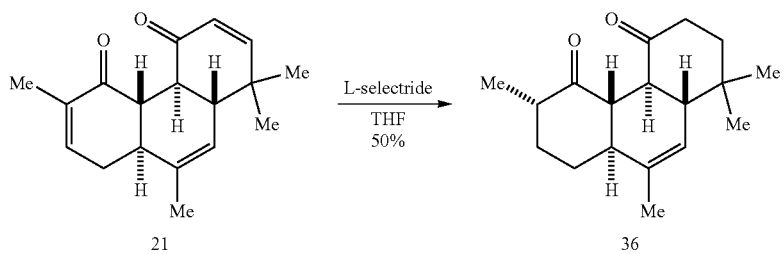

21 → 36

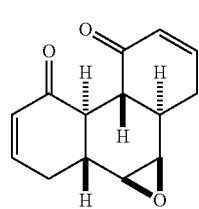

Compound 31.

Compound 13 (8.5 mg, 0.040 mmol) was diluted in DCM (1 mL) in a flame-dried round-bottom flask. NaHCO$_3$ (50.0 mg, 0.60 mmol, 15 equiv.) was added at room temperature, followed by mCPBA (18.0 mg, 0.10 mmol, 2.5 equiv.). The solution stirred at room temperature until observed consumption of the starting material by TLC (2.5 h), after which it was diluted with saturated aqueous NaHCO$_3$ and extracted with DCM. The combined organic layers were washed with brine, dried over MgSO$_4$, and concentrated under reduced pressure. The crude material was purified by flash chromatography on silica gel with 30% EtOAc/hexanes to 50% EtOAc/hexanes gradient (6.2 mg, 0.027 mmol, 68% yield): $[\alpha]_D = -267.8$ (c 0.13, CHCl$_3$); IR (Germanium ATR): 2917, 1685, 1176, 793 cm$^{-1}$; $^1$H NMR (500 MHz, Chloroform-d) δ 6.86-6.71 (m, 2H), 6.06 (dtd, J=9.9, 4.1, 3.6, 2.0 Hz, 2H), 3.22 (dd, J=3.9, 1.9 Hz, 1H), 3.01 (d, J=3.8 Hz, 1H), 2.75-2.66 (m, 1H), 2.66-2.51 (m, 3H), 2.51-2.40 (m, 2H), 2.29 (dtt, J=15.1, 6.6, 3.1 Hz, 2H); $^{13}$C NMR (126 MHz, CDCl$_3$) δ 199.7, 199.1, 145.0, 144.6, 130.7, 130.2, 56.3, 54.6, 46.2, 43.2, 38.3, 37.9, 32.8, 31.3; HRMS (ESI): Exact mass calc'd for C$_{14}$H$_{15}$O$_3$ [M+H]$^+$, 231.1021. Found 231.1017.

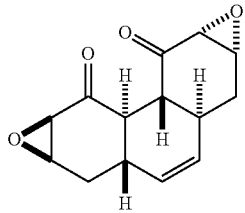

Compound 32.

13 (12.0 mg, 0.056 mmol) was diluted in a flame-dried round bottom flask with MeOH (0.7 mL), and 30% H$_2$O$_2$ was added (35 μL, 0.30 mmol, 5.0 equiv.) The mixture was cooled to 0° C., and aqueous NaOH (1M, 0.12 mL, 0.12 mmol, 2.0 equiv.) was added. The reaction was warmed to room temperature. Upon observed consumption of starting material by TLC (2.5 h), the reaction was poured into saturated aqueous Na$_2$S$_2$O$_3$ and extracted with ether. The combined organic layers were washed with brine, dried over MgSO$_4$, and concentrated under reduced pressure. The crude material was purified by flash chromatography with 20% EtOAc/hexanes (9.6 mg, 0.039 mmol, 70% yield): IR (Germanium ATR): 2919, 2850, 1783, 1241, 733 cm$^{-1}$; $^1$H NMR (500 MHz, Chloroform-d) δ 5.42 (d, J=2.4 Hz, 1H), 3.60 (q, J=3.9 Hz, 1H), 3.38-3.28 (m, 1H), 2.98 (dd, J=8.8, 3.1 Hz, 1H), 2.46 (s, 1H), 2.24 (dt, J=14.5, 5.0 Hz, 1H), 1.90 (t, J=13.7 Hz, 1H); $^{13}$C NMR (126 MHz, CDCl$_3$) δ 205.9, 128.5, 58.4, 55.7, 42.4, 41.5, 30.0; HRMS (ESI): Exact mass calc'd for C$_{14}$H$_{14}$O$_4$Na [M+Na]$^+$, 269.0790. Found 269.0770.

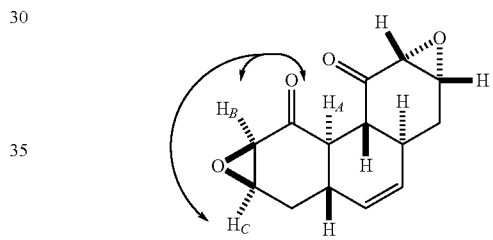

The $^1$H NMR and $^{13}$C NMR spectra are symmetrical, proving preservation of C$_2$ symmetry in the product. The epoxide stereochemistry was elucidated through COSY and NOESY NMR spectra, as each proton was assigned, and NOE interactions observed between proton H$_A$ and protons H$_B$ and H$_C$.

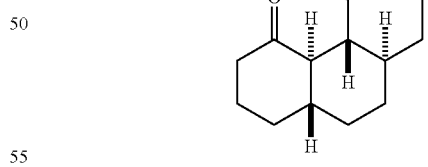

Compound 33.

13 (46.0 mg, 0.21 mmol) was diluted in a flame-dried round bottom flask with MeOH (4 mL). Pd/C (22.8 mg, 0.021 mmol, 10 mol %) was added at room temperature. H$_2$ was bubbled through the solution for 1 minute, and then the reaction stirred under H$_2$ overnight. The reaction was then purged with N$_2$ for 10 minutes before filtering through Celite with EtOAc. The solvent was evaporated under reduced pressure, and the crude material was purified by flash chromatography with 20% EtOAc/hexanes (45.7 mg, 0.21 mmol, 99% yield): IR (Germanium ATR): 2922, 2851, 1709, 1447 cm⁻¹; ¹H NMR (499 MHz, Chloroform-d) δ 2.56-2.48 (m, 1H), 2.47-2.41 (m, 1H), 2.35 (ddt, J=12.4, 4.2, 1.9 Hz, 1H), 2.10 (dddt, J=12.8, 6.3, 4.3, 2.4 Hz, 1H), 1.82-1.74 (m, 2H), 1.65 (qt, J=13.4, 4.2 Hz, 1H), 1.54-1.44 (m, 1H), 1.40 (dtq, J=11.3, 8.5, 2.8 Hz, 1H), 1.19-1.13 (m, 1H); ¹³C NMR (126 MHz, CDCl$_3$) δ 211.4, 53.2, 44.8, 42.2, 33.2, 33.0, 27.8; HRMS (ESI): Exact mass calc'd for C$_{14}$H$_{20}$O$_2$Na [M+Na]⁺, 243.1361. Found 243.1354.

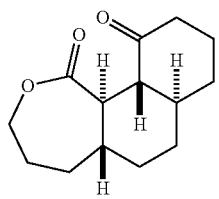

Compound 34.

Trifluoroperacetic acid was prepared by the addition of CHCl$_3$ (3 mL) and TFAA (445 µL, 3.2 mmol, 65 equiv.) to a flame-dried round-bottom flask. The flask was cooled to 0° C. and 30 wt % H$_2$O$_2$ (180 µL, 1.6 mmol, 32 equiv.) was added to this solution dropwise. After five minutes, this solution was added dropwise over 15 minutes to another flame-dried round-bottom flask with 33 (10.0 mg, 0.045 mmol), CHCl$_3$ (1 mL), and Na$_2$HPO$_4$ (130 mg, 0.92 mmol, 18 equiv.) at 0° C. Upon observed consumption of the starting material by TLC (3 h), the mixture was slowly poured into saturated aqueous NaHSO$_3$ and extracted twice with CHCl$_3$ and once with EtOAc. The combined organic layers were washed with brine, dried over MgSO$_4$, and concentrated under reduced pressure. The crude material was purified by flash chromatography on silica gel with 20% EtOAc/hexanes (5.8 mg, 0.025 mmol, 56% yield): [α]$_D$= −6.7 (c 0.13, CHCl$_3$); IR (Germanium ATR): 2918, 2850, 1728, 1713, 1463 cm⁻¹; ¹H NMR (499 MHz, Chloroform-d) δ 4.40 (dd, J=12.5, 10.4 Hz, 1H), 4.36-4.26 (m, 1H), 2.87 (ddd, J=12.1, 10.5, 1.1 Hz, 1H), 2.75 (t, J=10.8 Hz, 1H), 2.48 (tdd, J=13.7, 6.3, 1.1 Hz, 1H), 2.38 (ddt, J=13.1, 4.3, 2.2 Hz, 1H), 2.15-2.06 (m, 1H), 2.03-1.90 (m, 2H), 1.86 (dt, J=13.6, 3.9 Hz, 2H), 1.82-1.71 (m, 2H), 1.71-1.61 (m, 1H), 1.47 (dtd, J=15.3, 7.7, 3.8 Hz, 1H), 1.40-1.29 (m, 2H), 1.30-1.17 (m, 2H), 1.01 (tdd, J=13.5, 11.5, 3.6 Hz, 1H); ¹³C NMR (126 MHz, CDCl$_3$) δ 211.4, 177.2, 68.1, 55.8, 43.2, 43.2, 42.0, 37.9, 35.3, 34.3, 33.1, 32.5, 28.4, 27.1; HRMS (ESI): Exact mass calc'd for C$_{14}$H$_{21}$O$_3$ [M+H]⁺, 237.1491. Found 237.1478.

Scheme S18. Epimerization of the minor stereochemistry to the major, all trans stereochemistry.

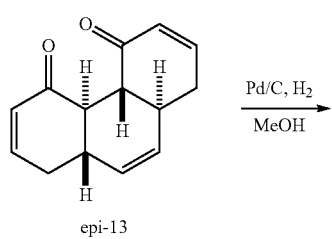

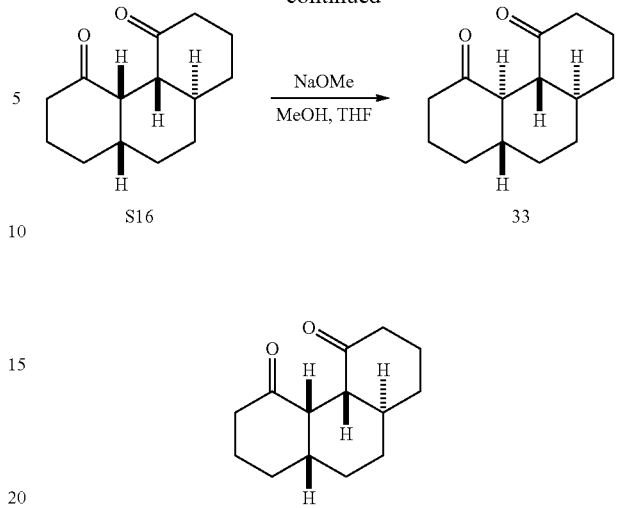

Compound S16.

The same procedure was followed as for the formation of Compound 33 above. Compound epi-13 (110.0 mg, 0.51 mmol) was diluted in a flame-dried flask with MeOH (9.6 mL). Pd/C (55.0 mg, 0.051 mmol, 10 mol %) was added at room temperature. H$_2$ was bubbled through solution for 1 minute, and then the reaction stirred under H$_2$ overnight. The reaction was then purged with N$_2$ for 10 minutes before filtering through Celite with EtOAc. The solvent was evaporated under reduced pressure, yielding the clean hydrogenated product (101.5 mg, 0.46 mmol, 90%): [α]$_D$=−37.1 (c 0.19, CHCl$_3$); IR (Germanium ATR): 2924, 2851, 1704, 1446, 1121 cm⁻¹; ¹H NMR (500 MHz, Chloroform-d) δ 3.30 (t, J=4.4 Hz, 1H), 2.52 (ddt, J=16.1, 4.8, 2.3 Hz, 1H), 2.42 (td, J=13.4, 6.4 Hz, 1H), 2.28 (ddt, J=13.3, 4.1, 2.2 Hz, 1H), 2.19 (ddd, J=16.2, 12.7, 6.4 Hz, 2H), 2.05 (qq, J=12.5, 5.0, 4.2 Hz, 1H), 1.94 (tdd, J=14.2, 6.9, 3.8 Hz, 3H), 1.89-1.76 (m, 4H), 1.72-1.61 (m, 2H), 1.45-1.35 (m, 1H), 1.25 (dtd, J=17.3, 13.3, 4.2 Hz, 2H), 1.16-1.01 (m, 1H); ¹³C NMR (126 MHz, CDCl$_3$) δ 210.3, 209.6, 55.6, 49.6, 42.6, 41.4, 40.5, 36.9, 34.1, 32.3, 31.0, 27.7, 23.9, 23.5; HRMS (ESI): Exact mass calc'd for C$_{14}$H$_{20}$O$_2$Na [M+Na]⁺, 243.1361. Found 243.1360.

To epimerize to the all trans conformation: S16 (135.0 mg, 0.61 mmol) was dissolved in THF (6 mL, 0.10 M). NaOMe (1.53 mL, 1 M in MeOH, 1.53 mmol, 2.5 equiv.) was added at room temperature. After stirring for 50 minutes, the yellow mixture was quenched with saturated NH$_4$Cl and extracted with ether. The combined organic extracts were dried over MgSO$_4$ and the solvent evaporated under reduced pressure, yielding the cleanly epimerized material, 33 (134.8 mg, 0.61 mmol, quantitative yield).

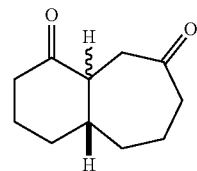 [SMILES: O=C1CCC[C@@H]2CCCC(=O)C2C1]

Compound S17.

30, a 1.3:1 mixture of diastereomers, (5.0 mg, 0.03 mmol) was diluted in a flame-dried flask with MeOH (1 mL). Pd/C (3.2 mg, 0.003 mmol, 10 mol %) was added at room temperature. H$_2$ was bubbled through solution for 1 minute, and then the reaction stirred under H$_2$ overnight. The reaction was then purged with N$_2$ for 10 minutes before filtering through Celite with EtOAc. The solvent was evaporated under reduced pressure, yielding the clean hydrogenated product as a mixture of diastereomers (5.0 mg, 0.03 mmol, quantitative yield): $^1$H NMR (500 MHz, Chloroform-d) δ 2.98-2.92 (m, 1H), 2.88 (d, J=12.6 Hz, 1H), 2.64 (t, J=12.1 Hz, 1H), 2.56 (dt, J=17.7, 4.0 Hz, 1H), 2.50 (dd, J=16.8, 6.5 Hz, 1H), 2.36 (dddd, J=33.0, 22.8, 16.3, 11.9 Hz, 6H), 2.23 (t, J=11.5 Hz, 1H), 2.12-1.90 (m, 6H), 1.90-1.48 (m, 11H), 1.31-1.20 (m, 3H); $^{13}$C NMR (126 MHz, CDCl$_3$) δ 214.3, 212.7, 211.4, 209.8, 53.6, 50.9, 49.1, 44.1, 44.0, 43.8, 42.2, 41.8, 41.5, 41.2, 36.7, 34.1, 32.4, 32.0, 26.4, 23.3, 22.6, 22.3.

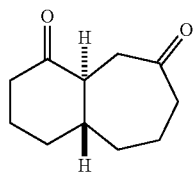 [SMILES: O=C1CCC[C@@H]2CCCC(=O)[C@H]2C1]

Compound 35.

The same epimerization conditions were used as detailed above, converting the mixture of hydrogenated diastereomers into the trans product. S17 (5.0 mg, 0.03 mmol) was dissolved in THF (0.5 mL). NaOMe (75 µL, 1 M in MeOH, 0.08 mmol, 2.5 equiv.) was added at room temperature. After stirring for 20 minutes, the yellow mixture was quenched with saturated NH$_4$Cl and extracted with ether. The combined organic extracts were dried over MgSO$_4$ and the solvent evaporated under reduced pressure, yielding a single diastereomer where the minor diastereomer had successfully epimerized to the major trans product, 35 (5.0 mg, 0.03 mmol, quantitative yield): [α]$_D$=−15.4 (c 0.23, CHCl$_3$); IR (Germanium ATR): 2918, 2849, 1701, 1462, 1091 cm$^{-1}$; $^1$H NMR (500 MHz, Chloroform-d) δ 2.88 (dd, J=12.7, 1.7 Hz, 1H), 2.67-2.60 (m, 1H), 2.56 (dddd, J=17.6, 4.9, 3.2, 1.3 Hz, 1H), 2.45-2.26 (m, 3H), 2.23 (tt, J=11.4, 1.4 Hz, 1H), 2.07 (dtd, J=12.6, 6.2, 3.2 Hz, 1H), 2.04-1.98 (m, 1H), 1.98-1.91 (m, 1H), 1.87-1.79 (m, 1H), 1.77-1.68 (m, 1H), 1.68-1.59 (m, 1H), 1.56-1.48 (m, 1H), 1.26 (d, J=9.9 Hz, 2H); $^{13}$C NMR (126 MHz, CDCl$_3$) δ 214.3, 209.8, 53.6, 49.1, 43.8, 41.8, 41.5, 36.7, 34.1, 26.4, 22.3; HRMS (EI): Exact mass calc'd for C$_{11}$14$_{16}$O$_2$ [M]$^+$, 180.1150. Found 180.1148.

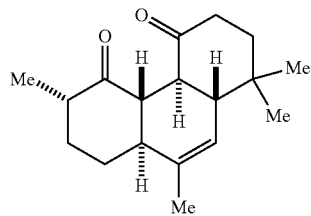

Compound 36.

A solution of 21 (8.0 mg, 0.030 mmol) in THF (0.6 mL) was cooled to −78° C. and a solution of L-selectride was added dropwise (1 M, 90 µL, 0.088 mmol, 2.4 equiv.). The reaction was maintained at this temperature, and upon observed consumption of the starting material by TLC, (2 h) the gold reaction was warmed to 0° C. and quenched with saturated NH$_4$Cl solution. The mixture was extracted with EtOAc, the combined organic extracts were dried over Na$_2$SO$_4$, and the solvent evaporated under reduced pressure. The crude material was flashed with 2% EtOAc/hexanes (4.5 mg, 0.016, 54%): [α]$_D$=+197.6 (c 0.20, CHCl$_3$); IR (Germanium ATR): 2963, 2929, 1719, 1690, 1373 cm$^{-1}$; $^1$H NMR (499 MHz, Chloroform-d) δ 5.35 (s, 1H), 2.82 (t, J=11.3 Hz, 1H), 2.75-2.65 (m, 2H), 2.61 (t, J=11.1 Hz, 1H), 2.28-2.19 (m, 2H), 2.19-2.10 (m, 1H), 2.06-1.95 (m, 2H), 1.84-1.78 (m, 1H), 1.70 (s, 3H), 1.69-1.58 (m, 1H), 1.44 (t, J=11.7 Hz, 1H), 1.38-1.28 (m, 1H), 1.03 (d, J=3.6 Hz, 9H); $^{13}$C NMR (126 MHz, CDCl$_3$) δ 212.6, 211.9, 136.7, 122.5, 52.3, 51.6, 47.3, 46.0, 45.1, 43.1, 39.3, 37.2, 33.9, 29.7, 28.6, 21.4, 19.7, 14.4; HRMS (ESI): Exact mass calc'd for C$_{18}$H$_{26}$O$_2$Na [M+Na]$^+$, 297.1831. Found 297.1831.

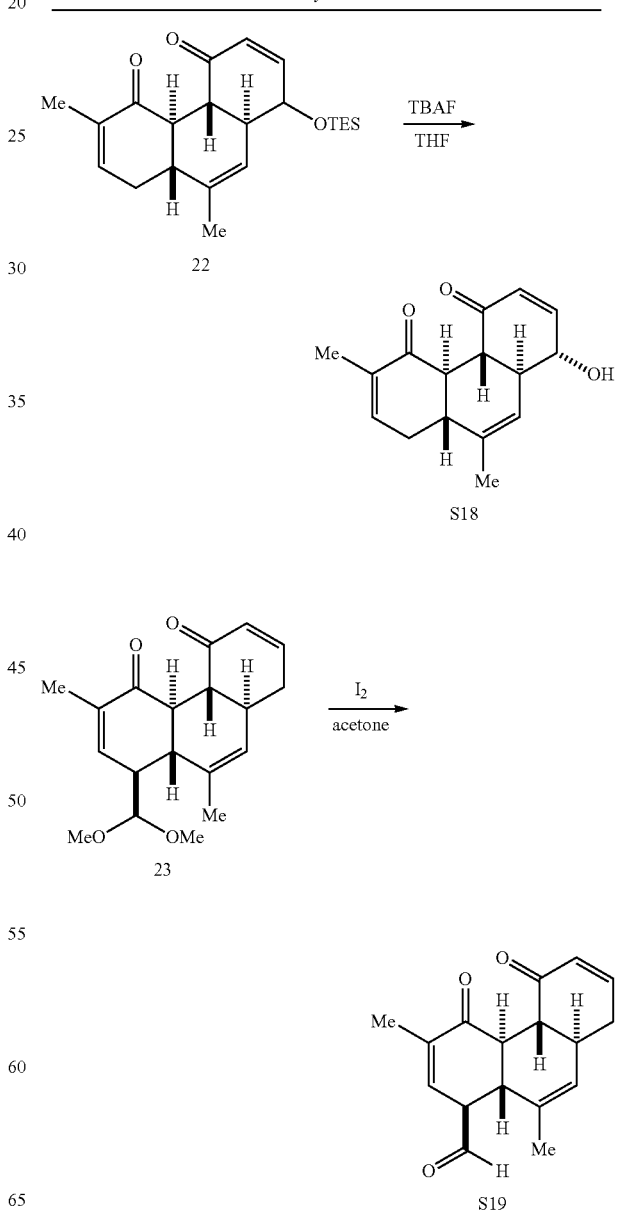

Scheme S19. Deprotection of ether 22 and acetal 23 to alcohol S18 and aldehyde S19.

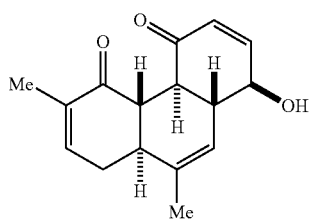

Compound S18.

To a solution of 22 (14.7 mg, 0.039 mmol) in THF (0.5 mL) at 0° C. was added a solution of 1 M TBAF in THF dropwise (50 μL, 0.05 mmol, 1.3 equiv.). Upon observed consumption of starting material by TLC (40 min.), the reaction was filtered through silica gel with EtOAc and the solvent evaporated under reduced pressure. The crude material was purified by flash chromatography on silica gel with 30% to 50% EtOAc/hexanes (9.3 mg, 0.036 mmol, 91%): $[\alpha]_D$=+499.1 (c 0.39, CHCl$_3$); IR (Germanium ATR): 3435, 2922, 2855, 1679, 1372, 1052, 806 cm$^{-1}$; $^1$H NMR (500 MHz, Chloroform-d) δ 6.70 (dd, J=10.2, 2.0 Hz, 1H), 6.55 (dt, J=5.7, 1.8 Hz, 1H), 6.04 (dd, J=10.2, 2.4 Hz, 1H), 5.73 (q, J=1.9 Hz, 1H), 4.27 (dt, J=9.6, 2.2 Hz, 1H), 2.74-2.63 (m, 3H), 2.43 (tdd, J=11.6, 4.5, 2.3 Hz, 1H), 2.35 (td, J=11.7, 11.1, 5.9 Hz, 1H), 2.14 (ddq, J=18.5, 10.9, 2.5 Hz, 1H), 1.97 (d, J=15.9 Hz, 1H), 1.83 (dt, J=2.9, 1.5 Hz, 3H), 1.72 (q, J=1.6 Hz, 3H); $^{13}$C NMR (126 MHz, CDCl$_3$) δ 200.5, 199.5, 148.8, 140.3, 136.6, 135.8, 130.1, 120.3, 73.1, 47.7, 47.0, 45.0, 41.4, 32.2, 20.3, 15.9; HRMS (ESI): Exact mass calc'd for C$_{16}$H$_{18}$O$_3$Na [M+Na]$^+$, 281.1154. Found 281.1159.

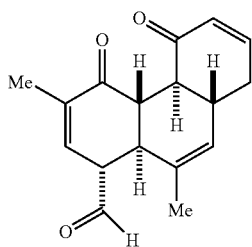

Compound S19.

To a solution of 23 (10.0 mg, 0.031 mmol) in acetone (0.5 mL) was added I$_2$ (~1 mg) at room temperature. The brown reaction stirred at room temperature for 20 minutes before quenching with saturated Na$_2$S$_2$O$_3$. The mixture was extracted with DCM, the combined organic extracts were dried over Na$_2$SO$_4$, and the solvent evaporated under reduced pressure. The crude material was purified by flash chromatography on silica gel with 20% EtOAc/hexanes (7.8 mg, 0.029 mmol, 93%): $[\alpha]_D$=+260.7 (c 0.31, CHCl$_3$); IR (Germanium ATR): 3026, 2920, 2825, 1724, 1685, 1378, 1042, 749 cm$^{-1}$; $^1$H NMR (500 MHz, Chloroform-d) δ 9.59 (d, J=3.7 Hz, 1H), 6.80 (ddd, J=10.1, 5.2, 2.2 Hz, 1H), 6.06 (dd, J=10.1, 3.0 Hz, 1H), 6.01 (dq, J=3.3, 1.7 Hz, 1H), 5.34 (q, J=1.8 Hz, 1H), 3.35 (ddt, J=9.9, 3.6, 2.4 Hz, 1H), 2.96-2.89 (m, 1H), 2.82 (dd, J=12.6, 10.8 Hz, 1H), 2.75 (dd, J=12.3, 10.8 Hz, 1H), 2.55-2.45 (m, 2H), 2.24 (ddt, J=19.3, 12.0, 2.5 Hz, 1H), 1.94-1.89 (m, 3H), 1.61 (dt, J=2.6, 1.4 Hz, 3H); $^{13}$C NMR (126 MHz, CDCl$_3$) δ 200.0, 199.5, 199.5, 145.8, 141.3, 133.2, 132.2, 130.5, 126.8, 57.1, 46.7, 44.6, 40.4, 38.3, 34.3, 23.3, 16.3; HRMS (ESI): Exact mass calc'd for C$_{17}$H$_{18}$O$_3$Na [M+Na]$^+$, 293.1154. Found 293.1159.

6. Biological Assays of Prepared Compounds

A. Cell Line Growth Conditions:

Cell lines PC-3, HT29, Hela, and MDA-MB-231 were cultured in RPMI1640 with 10% FBS media. Cell line MDA-MB-231-LM24 was cultured in DMEM with 400 ug/mL geneticin.

Normal breast cell line MCF10A was cultured in DMEM/F12 with 5% horse serum, 20 ng/mL EGF, 0.5 mg/mL hydrocortisone, 100 ng/mL cholera toxin, 10 μg/mL insulin, and 1% pen/strep.

B. Cell Viability Experiments at 1 mM:

PC-3, HT29, Hela, and MDA-MB-231, and MDA-MB-231-LM24 cells were plated in 9-11 black plates at a density of 20,000 cells per well (based on NCI recommendation for adherent cells) in 90 μL volume of 5% FBS RPMI1640 complete media with 50 μg/mL gentamicin and incubated at 37° C. overnight. Each compound was diluted in RPMI1640 complete media supplemented with 5% FBS and 50 μg/mL of gentamycin, and 10 μL of this solution was added to each well to give a final concentration of 1 mM (1% overall DMSO, N=4 wells).

Normal breast cells (MCF10A) were plated in 96-well black plates at a density of 20,000 cells per well (based on the NCI recommendation for adherent cells) in 90 μL volume of DMEM/F12 with 2% horse serum, 0.5 μg/mL hydrocortisone, 100 ng/mL cholera toxin, 10 μg/mL insulin, and 1% pen/strep, and incubated at 37° C. overnight. The compounds were diluted in the media specified above, and 10 μL of this solution was added to each well to give a final concentration of 1 mM (1% overall DMSO, N=4 wells).

Cells treated with Doxorubicin with 1% overall DMSO were used as a positive control, and cells media containing 1% DMSO were used as a negative control.

48 hours following treatment, cell proliferation was evaluated using the CellTiter-GLO Luminescent Cell Viability Assay (Promega, Madison, Wis.). Plates were allowed to equilibrate to room temperature for 20 minutes, and 100 μL of CellTiter-GLO reagent was added to all wells. The plates were shaken for 2 minutes and incubated at room temperature for 10 minutes. Luminescence was measured using a Syngergy H1-M microplate reader (BioTek Instruments, Inc.).

C. IC50 Experiments:

The compound was diluted in RPMI1640 complete media supplemented with 5% FBS and 50 μg/mL of gentamycin, and 100 μL of this solution was added to each well to give a final concentration of 0.00001-1 mM (N=4 wells). DMSO was held constant at 1%, for all dose points.

48 hours following treatment, cell proliferation was evaluated using the CellTiter-GLO Luminescent Cell Viability Assay (Promega, Madison, Wis.). Plates were allowed to equilibrate to room temperature for 20 minutes, and 100 μL of CellTiter-GLO reagent was added to all wells. The plates were shaken for 2 minutes and incubated at room temperature for 10 minutes. Luminescence was measured using a Syngergy H1-M microplate reader (BioTek Instruments, Inc.). The IC50 value was determined by Prism GraphPad Software.

7. Synthesis of (+)-7,20-Diisocyanoadociane

Experimental Procedures and Characterization Data

A. Starting Material Synthesis from Common Enantioenriched Silane Intermediates

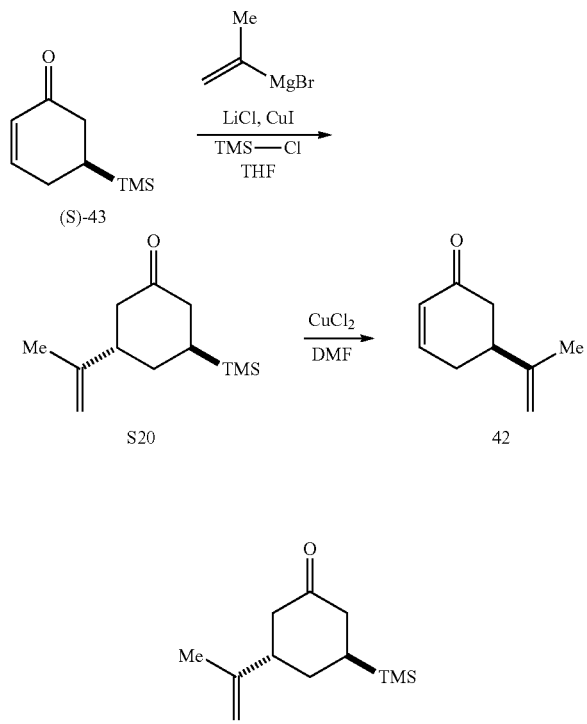

Compound S20.

LiCl (95 mg, 2.13 mmol, 20 mol %) and CuI (0.20 g, 1.06 mmol, 10 mol %) were added to a flame-dried round-bottom flask. The flask was cooled to 0° C., and (S)-43 (1.79 g, 10.6 mmol, 1.0 equiv.) in THF (50 mL) was added via cannula (12 mL THF rinse). TMS-Cl (1.5 mL, 11.7 mmol, 1.1 equiv.) was added, and the mixture stirred for 25 minutes. The freshly prepared and titrated isopropenyl Grignard solution, (0.62 M, 20.7 mL, 12.8 mmol, 1.2 equiv.) was added dropwise via syringe over 30 minutes and the reaction allowed to slowly warm to room temperature. Upon observed consumption of the starting material by TLC (1.5 h), the black reaction was quenched with saturated NH$_4$Cl solution and extracted with ether. The combined organic extracts were washed twice with 3 M HCl and once with brine, then dried over MgSO$_4$, and concentrated under reduced pressure. The crude material was purified by flash chromatography on silica gel with 5% ether/pentane. (1.45 g, 6.89 mmol, 65% yield): [α]$_D$=−56.3 (c 0.12, CHCl$_3$); IR (Germanium ATR): 2953, 1713, 1249, 839 cm$^{-1}$; $^1$H NMR (499 MHz, Chloroform-d) δ 4.90 (d, J=1.7 Hz, 1H), 4.72 (d, J=1.7 Hz, 1H), 2.81 (s, 1H), 2.64-2.55 (m, 1H), 2.46 (ddd, J=15.0, 6.0, 1.0 Hz, 1H), 2.35-2.26 (m, 1H), 2.08 (ddd, J=14.8, 12.9, 1.1 Hz, 1H), 1.94-1.84 (m, 1H), 1.75-1.66 (m, 4H), 1.17 (tt, J=12.6, 3.8 Hz, 1H), 0.00 (d, J=0.6 Hz, 9H); $^{13}$C NMR (126 MHz, CDCl$_3$) δ 212.5, 146.5, 112.8, 45.2, 43.5, 42.2, 28.6, 22.1, 20.7, −3.4; HRMS (ESI): Exact mass calc'd for C$_{12}$H$_{22}$O SiNa [M+Na]$^+$, 233.1338. Found 233.1328.

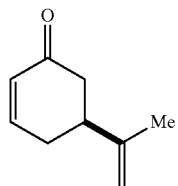

Compound 42.

CuCl$_2$ (2.7 g, 20.0 mmol, 3.0 equiv.) was added to a flame-dried round-bottom flask. S20 (1.4 g, 6.65 mmol, 1.0 equiv.) in DMF (48 mL, with an additional 3 mL DMF rinse) was added via cannula and the mixture heated to 55° C. After 2 hours, the black reaction was cooled to room temperature, diluted with brine, and extracted twice with pentane and once with 5% ether/pentanes. The combined organic extracts were dried over MgSO$_4$ and the solvent evaporated carefully. The crude material was purified by flash chromatography on silica gel with 15% ether/pentane. (0.652 g, 4.79 mmol, 72% yield): [α]$_D$=+29.2 (c 0.59, CHCl$_3$); IR (Germanium ATR): 2922, 1678, 1388, 881 cm$^{-1}$; $^1$H NMR (499 MHz, Chloroform-d) δ 7.01 (ddd, J=10.1, 5.8, 2.5 Hz, 1H), 6.11-5.98 (m, 1H), 4.83 (q, J=1.6 Hz, 1H), 4.78 (s, 1H), 2.78-2.66 (m, 1H), 2.57 (dd, J=16.2, 3.8 Hz, 1H), 2.53-2.44 (m, 1H), 2.41-2.27 (m, 2H), 1.77 (d, J=1.5 Hz, 3H); $^{13}$C NMR (126 MHz, CDCl$_3$) δ 199.8, 149.8, 146.6, 129.7, 110.9, 43.2, 42.2, 31.1, 20.6; HRMS (ESI): Exact mass calc'd for C$_9$H$_{13}$O [M+H]$^+$, 137.0966 Found 137.0962.

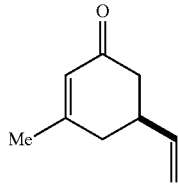

Compound 3.

See Section 2 above for experimental preparation and characterization data.

B. Implementation of Developed Methodology for the Synthesis of Fused Tricyclic Scaffold 41.

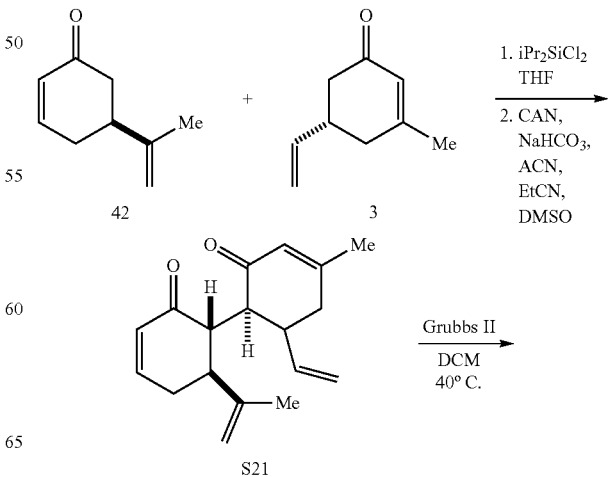

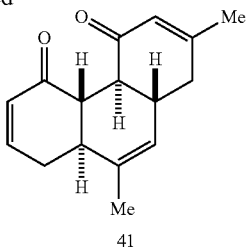

41

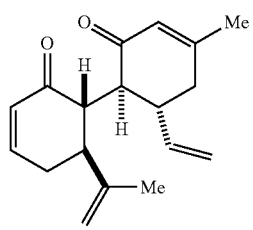 [SMILES: C=C[C@H]1CC(C)=CC(=O)[C@@H]1[C@H]1C(=O)C=CC[C@@H]1C(=C)C]

Compound S21.

To a flame dried conical flask was added diisopropylamine (113 µL, 0.81 mmol, 1.2 equiv.) and THF (0.8 mL). The flask was cooled to −78° C., and n-BuLi (freshly titrated to 2.04 M, 0.36 mL, 0.74 mmol, 1.1 equiv.) was added. After 10 minutes, enone 42 (92.0 mg, 0.67 mmol, 1.0 equiv.) in THF (0.3 mL) was added (0.1 mL rinse). The solution stirred for 30 minutes before slowly adding it via cannula to a flask containing iPr$_2$SiCl$_2$ (120 µL, 0.67 mmol, 1.0 equiv.) and THF (2.7 mL), also at −78° C., over 1 hour. Meanwhile, LDA was prepared exactly as above in a separate conical flask. After 10 minutes, enone 3 (92.0 mg, 0.67 mmol, 1.0 equiv.) in THF (0.3 mL) was added (0.1 mL rinse). This solution stirred for 30 minutes before adding it slowly to the reaction flask via cannula over 1 hour (about 40 minutes following the completion of the first enolate addition). The mixture stirred at −78° C. for 45 min before warming to room temperature. Upon observed consumption of the starting materials by TLC (2 h), the orange reaction was quenched with pH 7 buffer and extracted with pentanes. The combined organic layers were dried over MgSO$_4$, and concentrated under reduced pressure. The crude material was placed on the vacuum manifold overnight and was used directly in the next reaction.

To a flame-dried round-bottom flask was added CAN (0.81 g, 1.47 mmol, 2.2 equiv.), NaHCO$_3$ (0.25 g, 2.98 mmol, 4.4 equiv.), ACN (22 mL, dried over activated sieves), and DMSO (95.2 µL, 1.34 mmol, 2.0 equiv.). The mixture was cooled to −30° C. and stirred vigorously while the crude material in EtCN (3 mL, dried over activated sieves, 0.4 mL rinse) was added via cannula. Upon observed consumption of the starting silyl bis-enol ether by TLC (15 min.), the orange mixture was diluted with saturated NaHCO$_3$ solution, extracted with CHCl$_3$. The combined organic layers were dried over MgSO$_4$ filtered through Celite with EtOAc, and concentrated under reduced pressure to yield a 5:1 mixture of diastereomers. The crude material was purified by flash chromatography on silica gel using 5% EtOAc/hexane (major diastereomer: 73.0 mg, 0.27 mmol, 40% yield over two steps; total coupled yield: 88.8 mg, 0.33 mmol, 49% yield): [α]$_D$=+42.9 (c 0.84, CHCl$_3$); IR (Germanium ATR): 2916, 1658, 1380, 1211, 916 cm$^{-1}$; $^1$H NMR (500 MHz, Chloroform-d) δ 6.90 (ddd, J=10.0, 5.9, 2.4 Hz, 1H), 5.99 (ddd, J=10.0, 2.8, 1.0 Hz, 1H), 5.85 (q, J=1.5 Hz, 1H), 5.59 (dt, J=17.0, 9.8 Hz, 1H), 5.14-5.08 (m, 2H), 4.84 (dq, J=3.5, 1.8 Hz, 2H), 3.52 (td, J=12.2, 4.9 Hz, 1H), 3.44-3.30 (m, 1H), 2.63 (d, J=12.8 Hz, 1H), 2.44-2.27 (m, 3H), 2.27-2.20 (m, 2H), 1.93 (d, J=1.2 Hz, 3H), 1.66 (t, J=1.1 Hz, 3H); $^{13}$C NMR (126 MHz, CDCl$_3$) δ 200.3, 199.1, 159.3, 148.2, 145.5, 140.6, 130.2, 127.2, 117.6, 114.8, 49.3, 48.8, 48.1, 45.2, 38.4, 31.8, 24.2, 18.6; HRMS (ESI): Exact mass calc'd for C$_{18}$H$_{22}$O$_2$Na [M+Na]$^+$, 293.1518. Found 293.1513.

Note: scaled up procedure for oxidative coupling: While formation of the silyl bis-enol ether is a very scalable process, the developed oxidative coupling conditions are not as amenable to large scale ups, which would require re-optimization due to reagent solubility issues. Therefore, to bring forward larger amounts of material, the following procedure was followed: To a flame dried conical flask was added diisopropylamine (1.24 mL, 8.81 mmol, 1.2 equiv.) and THF (10 mL). The flask was cooled to −78° C., and n-BuLi (freshly titrated to 2.28 M, 3.55 mL, 8.08 mmol, 1.1 equiv.) added. After 10 minutes, enone 42 (1.0 g, 7.34 mmol, 1.0 equiv.) in THF (4 mL) was added (0.3 mL rinse). The solution stirred for 30 minutes before slowly adding it via cannula to a flask containing iPr$_2$SiCl$_2$ (1.32 mL, 7.34 mmol, 1.0 equiv.) and THF (29 mL), also at −78° C. over 1.5 hours. Meanwhile, LDA was prepared exactly as above in a separate conical flask. After 10 minutes, enone 3 (1.0 g, 7.34 mmol, 1.0 equiv.) in THF (4 mL) was added (0.3 mL rinse). This solution stirred for 30 minutes before adding it slowly to the reaction flask via cannula over 1 hour (45 min. following the completion of the first enolate addition). The mixture stirred at −78° C. for 45 min. and then was warmed to room temperature. Upon observed consumption of the starting materials by TLC (1.5 h from when warmed to room temperature), the orange reaction was quenched with pH 7 buffer and extracted with pentanes. The combined organic layers were dried over MgSO$_4$, and concentrated under reduced pressure. The crude material was placed on the vacuum manifold overnight. The crude silyl bis-enol ether was split into seven equal portions (0.404 g, 1.05 mmol) and each was used in the following manner: To a flame-dried 100 mL flask was added CAN (1.27 g, 2.31 mmol, 2.2 equiv.), NaHCO$_3$ (0.39 g, 4.62 mmol, 4.4 equiv.), ACN (35 mL, 0.03 M), and DMSO (0.15 mL, 2.10 mmol, 2.0 equiv.). The mixture was cooled to −30° C., and stirred vigorously while the silyl bis-enol ether in EtCN (5 mL) was added to the reaction via cannula (0.3 mL rinse). Upon observed consumption of the starting silyl bis-enol ether by TLC (15 min.), the orange mixture was diluted with saturated NaHCO$_3$ solution, extracted with CHCl$_3$. The combined organic layers were dried over MgSO$_4$ filtered through Celite with EtOAc, and concentrated under reduced pressure to yield a ~7:1 mixture of diastereomers. The combined crude material from all seven partitions was purified by flash chromatography on silica gel using 5% EtOAc/hexane (major diastereomer: 0.97 g, 3.6 mmol, 49% over two steps; total coupled yield: 1.1 g, 4.10 mmol, 56%).

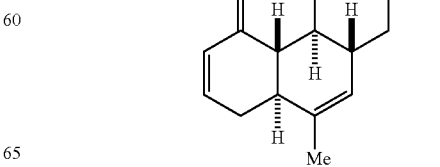

Compound 41.

To a flame-dried flask was added Grubbs II from the glove box (16 mg, 0.02 mmol, 10 mol %). S21 (40.0 mg, 0.15 mmol, 1.0 equiv.) in DCM (2.5 mL, with an additional 0.4 mL rinse) was added to the flask via cannula and the reaction heated to 40° C. Upon observed consumption of the starting material by TLC (22 h), 10 μL DMSO were added, and the mixture stirred for 2 h. The solvent was evaporated, and the crude material was purified by flash chromatography on silica gel with 20% EtOAc/hexanes (30.5 mg, 0.126 mmol, 84% yield). Solid crystals for x-ray crystallography were obtained by slow evaporation of ethyl acetate. $[\alpha]_D$=+561.6 (c 1.13, CHCl$_3$); IR (Germanium ATR): 2923, 1670, 1681, 1379, 1176, 843 cm$^{-1}$; $^1$H NMR (500 MHz, Chloroform-d) δ 6.81 (ddd, J=10.0, 5.6, 2.1 Hz, 1H), 6.10 (ddd, J=10.0, 3.1, 0.9 Hz, 1H), 5.90 (dd, J=2.7, 1.4 Hz, 1H), 5.28 (q, J=1.8 Hz, 1H), 2.78-2.66 (m, 2H), 2.56 (dd, J=12.4, 10.8 Hz, 1H), 2.52-2.38 (m, 2H), 2.34 (dd, J=18.0, 4.0 Hz, 1H), 2.27-2.12 (m, 2H), 1.93 (d, J=1.2 Hz, 3H), 1.70 (dt, J=2.4, 1.2 Hz, 3H); $^{13}$C NMR (126 MHz, CDCl$_3$) δ 200.3, 199.6, 157.2, 145.3, 134.4, 130.5, 127.1, 124.8, 47.6, 45.9, 42.0, 39.7, 37.8, 32.5, 23.7, 20.3; HRMS (ESI): Exact mass calc'd for C$_{16}$H$_{18}$O$_2$Na [M+Na]$^+$, 265.1205. Found 265.1199. The structure of the compound was confirmed by x-ray diffraction analysis.

C. Final Ring Construction

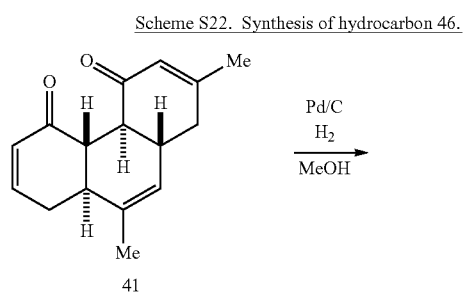

Scheme S22. Synthesis of hydrocarbon 46.

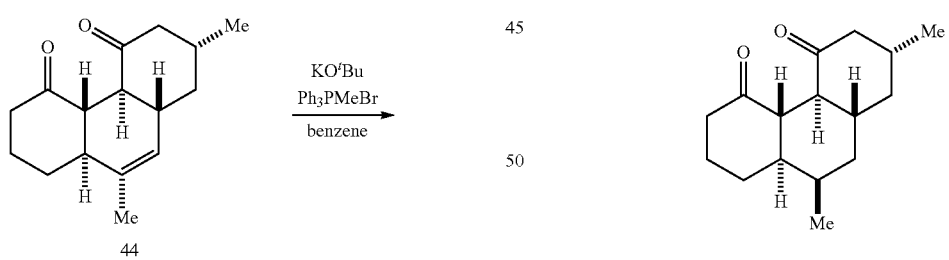

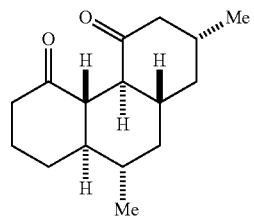

Compound 44.

41 (100 mg, 0.41 mmol, 1.0 equiv.) was diluted in MeOH (14 mL, 0.03 M). Pd/C (44.0 mg, 0.041 mmol, 10 mol %) was added. H$_2$ was bubbled through the solution for 1 minute, and then the reaction was left to stir at room temperature under H$_2$ overnight. The reaction was then purged with N$_2$ for 1 h before filtering through Celite with EtOAc. The solvent was evaporated, and the crude material purified by flash chromatography on silica gel with 20% EtOAc/hexanes to yield a 3:1 mixture of diastereomers (95.0 mg, 0.38 mmol, 93% yield). The two diastereomers were separated by preparative HPLC using a C18 column and a 40-75% ACN/H$_2$O gradient solvent system. The structures of the major and minor products were elucidated by x-ray crystallography. Solid crystals for x-ray crystallography were obtained by slow evaporation of ether. Major isomer: $[\alpha]_D$=+41.2 (c 1.14, CHCl$_3$); IR (Germanium ATR): 2911, 1707, 1455 cm$^{-1}$; $^1$H NMR (500 MHz, Chloroform-d) δ 2.57-2.37 (m, 3H), 2.37-2.29 (m, 2H), 2.28-2.19 (m, 1H), 2.19-2.06 (m, 2H), 1.86 (dq, J=11.9, 6.3 Hz, 1H), 1.77 (dtd, J=13.2, 3.5, 1.8 Hz, 1H), 1.68 (dt, J=13.1, 3.4 Hz, 1H), 1.60 (tdd, J=14.2, 11.8, 3.3 Hz, 2H), 1.44 (qt, J=11.8, 3.2 Hz, 1H), 1.38-1.25 (m, 2H), 1.20 (q, J=12.2 Hz, 1H), 1.12-1.03 (m, 1H), 1.03 (d, J=6.6 Hz, 3H), 0.93 (d, J=6.3 Hz, 3H); $^{13}$C NMR (126 MHz, CDCl$_3$) δ 211.5, 210.9, 53.1, 52.6, 50.9, 50.2, 42.3, 42.1, 42.1, 41.8, 37.3, 35.4, 29.8, 27.7, 22.6, 19.9; HRMS (ESI): Exact mass calc'd for C$_{16}$H$_{24}$O$_2$Na [M+Na]$^+$, 271.1674. Found 271.1670. The structure of the compound was confirmed by x-ray diffraction analysis.

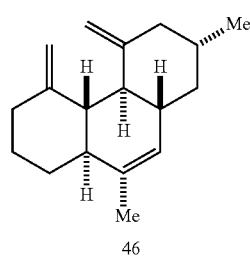

Compound 45 (Minor Isomer).

$^1$H NMR (500 MHz, Chloroform-d) δ 2.65 (t, J=11.3 Hz, 1H), 2.46 (ddd, J=18.5, 12.2, 6.0 Hz, 1H), 2.33 (td, J=11.2, 9.9, 5.4 Hz, 3H), 2.23 (t, J=12.4 Hz, 1H), 2.11 (dq, J=9.2, 3.2 Hz, 1H), 1.98-1.80 (m, 2H), 1.76-1.67 (m, 1H), 1.66-1.52 (m, 6H), 1.35 (td, J=13.1, 4.3 Hz, 1H), 1.18 (q, J=12.1 Hz, 1H), 1.02 (d, J=6.5 Hz, 3H), 0.92 (d, J=7.2 Hz, 3H); $^{13}$C NMR (126 MHz, CDCl$_3$) δ 212.1, 210.9, 52.9, 50.3, 47.2, 47.0, 42.3, 42.2, 40.4, 36.5, 35.4, 32.4, 30.5, 27.7, 22.6, 13.2; HRMS (ESI): Exact mass calc'd for C$_{16}$H$_{24}$O$_2$Na [M+Na]$^+$, 271.1674. Found 271.1670. The structure of the compound was confirmed by x-ray diffraction analysis.

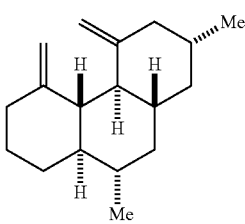

Compound 46.

KO*t*Bu (84.0 mg, 0.75 mmol, 3.6 equiv., sublimed and stored in the glove box freezer) was added to a flame-dried round-bottom flask. Benzene (1 mL) was added, followed by Ph$_3$PMeBr (278.0 mg, 0.78 mmol, 3.7 equiv.). The yellow mixture was heated to 80° C. for 1 h before cooling to room temperature and adding 44 (53.0 mg, 0.21 mmol) in benzene (0.8 mL, with an additional 0.3 mL rinse). The reaction was heated back to 80° C. Upon observed consumption of the starting material, and the characterized mono-olefinated product (15.5 h), the orange reaction was cooled to room temperature, diluted with water, and extracted with 50% ether/pentane. The combined organic extracts were dried over MgSO$_4$, and the solvent evaporated under reduced pressure. The crude material was purified by flash chromatography on silica gel using hexane. (42.3 mg, 0.173 mmol, 82% yield): $[\alpha]_D$=+65.2 (c 0.24, CHCl$_3$); IR (Germanium ATR): 2911, 2850, 1645, 1444, 883 cm$^{-1}$; $^1$H NMR (500 MHz, Chloroform-d) δ 4.69 (s, 2H), 4.33 (s, 1H), 4.31 (s, 1H), 2.35-2.25 (m, 2H), 2.08 (dd, J=13.3, 3.6 Hz, 1H), 2.00 (td, J=12.8, 4.7 Hz, 1H), 1.94-1.82 (m, 2H), 1.79 (t, J=10.6 Hz, 1H), 1.73-1.63 (m, 2H), 1.59-1.49 (m, 2H), 1.35 (qt, J=13.1, 4.3 Hz, 1H), 1.20 (ddddd, J=22.1, 12.6, 9.9, 6.3, 3.2 Hz, 2H), 1.12-1.00 (m, 1H), 0.92 (d, J=6.3 Hz, 4H), 0.88 (q, J=5.0 Hz, 3H), 0.85-0.79 (m, 2H); $^{13}$C NMR (126 MHz, CDCl$_3$) δ 151.6, 150.7, 106.1, 105.7, 51.8, 48.5, 48.3, 46.6, 43.9, 43.7, 43.2, 38.2, 37.2, 35.7, 31.7, 29.5, 22.6, 20.4; HRMS (EI): Exact mass calc'd for C$_{18}$H$_{28}$ [M]$^+$, 244.2191. Found 244.2173.

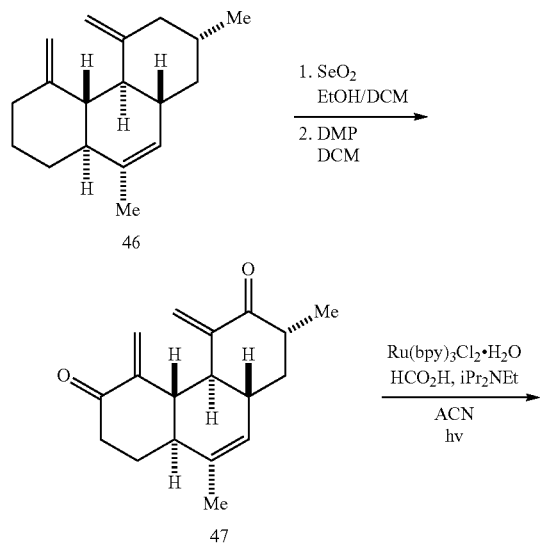

Scheme S23. Synthesis of Corey's diketone 40.

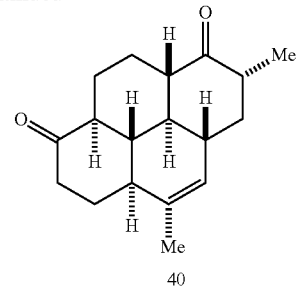

Compound 47.

To 46 (30.0 mg, 0.12 mmol, 1.0 equiv.) in EtOH (0.8 mL) and DCM (0.4 mL) was added SeO$_2$ (58.0 mg, 0.52 mmol, 4.0 equiv.). The mixture was heated to 78° C. Upon observed consumption of the starting material and the previously characterized mono-oxidation products by TLC (40 h), the yellow reaction was cooled to room temperature and the solvent evaporated. The crude material in DCM (2 mL, with an additional 0.5 mL rinse) was then added to a flame-dried round-bottom flask with DMP (157.0 mg, 0.37 mmol, 3.0 equiv.). Upon observed consumption of the starting material by TLC, with both alcohol diastereomers converging to one UV-active product (4 h), the mixture was diluted with saturated Na$_2$S$_2$O$_3$ solution and extracted with DCM. The combined organic extracts were washed with saturated NaHCO$_3$ solution, dried over MgSO$_4$, and the solvent evaporated under reduced pressure. This crude material was purified by flash chromatography on silica gel using 10% EtOAc/hexane (16.4 mg, 0.06 mmol, 50% yield over two steps): $[\alpha]_D$=+165.4 (c 0.73, CHCl$_3$); IR (Germanium ATR): 2922, 2853, 1694, 1615, 1260, 1915, 801 cm$^{-1}$; $^1$H NMR (500 MHz, Chloroform-d) δ 5.71 (d, J=1.7 Hz, 1H), 5.48 (d, J=1.7 Hz, 1H), 4.95 (d, J=2.0 Hz, 1H), 4.82 (d, J=2.0 Hz, 1H), 2.69 (ddd, J=16.3, 6.5, 3.1 Hz, 1H), 2.49-2.29 (m, 4H), 2.21 (t, J=10.4 Hz, 1H), 2.09 (ddd, J=13.4, 6.7, 2.7 Hz, 1H), 1.79-1.67 (m, 2H), 1.59 (s, 1H), 1.57-1.47 (m, 1H), 1.44-1.30 (m, 2H), 1.22 (ddd, J=21.6, 10.6, 3.2 Hz, 1H), 1.14 (d, J=6.5 Hz, 3H), 1.02 (d, J=6.3 Hz, 3H); $^{13}$C NMR (126 MHz, CDCl$_3$) δ 206.6, 203.7, 149.6, 148.3, 119.2, 117.4, 48.2, 47.0, 46.4, 45.4, 41.6, 41.3, 41.1, 39.7, 36.8, 28.2, 20.1, 15.1; HRMS (D): Exact mass calc'd for C$_{18}$H$_{24}$O$_2$ [M]$^+$, 272.1776. Found 272.1757.

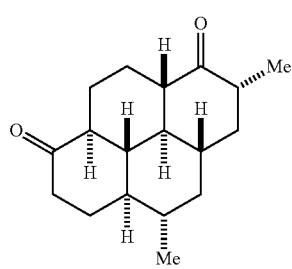

Compound 40.

Employing reductive cyclization conditions developed by Yoon and coworkers[15], 47 (21.0 mg, 0.077 mmol, 1.0 equiv.) was dissolved in freshly distilled ACN (1.6 mL). Ru(bpy)$_3$Cl$_2$.H$_2$O (2.0 mg, 0.0027 mmol, 3.5 mol %) was added, followed by HCO$_2$H (15 μL, 0.39 mmol, 5.0 equiv.) and iPr$_2$NEt (134 μL, 0.77 mmol, 10.0 equiv.). The orange mixture was cooled in a liquid nitrogen bath, placed under vacuum for 10 minutes, removed from vacuum and warmed to room temperature, and purged with N$_2$. This freeze-pump-thaw process was repeated three times, after which the orange reaction was irradiated with a 23 W (1600 lumen) compact fluorescent lamp at room temperature. Upon observed consumption of the UV-active starting material by TLC, (20 h), the solvent was evaporated under reduced pressure. The crude material was purified by flash chromatography on silica gel using 10% EtOAc/hexane (19.4 mg, 0.071 mmol, 92% yield): [α]$_D$=+16.0 (c 0.35, CHCl$_3$); IR (Germanium ATR): 2924, 2862, 1707, 1453 cm$^{-1}$; $^1$H NMR (499 MHz, Chloroform-d) δ 2.51-2.30 (m, 4H), 2.06-1.94 (m, 5H), 1.74 (dt, J=13.1, 3.5 Hz, 1H), 1.66 (tdt, J=11.6, 7.1, 3.5 Hz, 1H), 1.35-1.04 (m, 8H), 1.00 (d, J=6.5 Hz, 3H), 0.98 (d, J=6.5 Hz, 3H), 0.86 (q, J=12.1 Hz, 1H); $^{13}$C NMR (126 MHz, CDCl$_3$, referenced to 77.0 ppm) δ 213.0, 212.0, 53.6, 52.7, 52.2, 52.1, 46.3, 44.3, 43.0, 41.2, 41.0, 40.4, 36.4, 31.0, 23.7, 23.6, 19.9, 14.4; HRMS (ESI): Exact mass calc'd for C$_{18}$H$_{26}$O$_2$Na [M+Na]$^+$, 297.1831. Found 297.1827. All spectroscopic data for this compound agrees with previously reported values.[16]

REFERENCES

1. Pangborn, A. B.; Giardello, M. A.; Grubbs, R. H.; Rosen, R. K.; Timmers, F. J. *Organometal.* 1996, 15, 1518-1520.
2. Armarego, W. L. F.; Chai, C. L. L. *Purification of Laboratory Chemicals;* 5th Ed., Butterworth-Heinemann, 2003.
3. Bolze, P.; Dickmeiss, G.; Jorgensen, K. A. *Org. Lett.* 2008, 10, 3753-3756.
4. Zhao, L.; Wang, J. L.; Zheng, H. Y.; Li, Y.; Yang, K.; Cheng, B.; Jin, X. J.; Yao, X. J.; Zhai, H. B. *Org. Lett.* 2014, 16, 6378-6381.
5. Sarakinos, G.; Corey, E. J. *Org. Lett.* 1999, 1, 811-814.
6. Asaoka, M.; Sonoda, S.; Fujii, N.; Takei, H. *Tetrahedron,* 1990, 46, 1541-1552.
7. Torosyan, S. A.; Gimalova, F. A.; Valeev, R. F.; Miftakhov, M. S. Russ. *J. Org. Chem.* 2011, 47, 682-686.
8. Furrow, M. E.; Myers, A. G. *J. Am. Chem. Soc.* 2004, 126, 5436-5445.
9. Asaba, T.; Katoh, Y.; Urabe, D.; Inoue, M. *Angew. Chem. Int. Ed.* 2015, 54, 14457-14461.
10. Barros, T.; Maycock, C. D.; Ventura, R. *J. Org. Chem.* 1997, 62, 3984-3988.
11. Yamamoto, E.; Gokuden, D.; Nagai, A.; Kamachi, T.; Yoshizawa, K.; Hamasaki, A.; Ishida, T.; Tokunaga, M. *Org. Lett.* 2012, 14, 6178-6181.
12. Frazier, R. H.; Harlow, R. L. *J. Org. Chem.* 1980, 45, 5408-5411.
13. Hong, S. H.; Day, M. W.; Grubbs, R. H. *J. Am. Chem. Soc.* 2004, 126, 7414-7415.
14. Hong, S. H.; Sanders, D. P.; Lee, C. W.; Grubbs, R. H. *J. Am. Chem. Soc.* 2005, 127, 17160-17161.
15. Du, J.; Espelt, L. R.; Guzei, I. A.; Yoon, T. P. *Chem. Sci.,* 2011, 2, 2115-2119.
16. Corey, E. J.; Magriotis, P. A.; *J. Am. Chem. Sci.* 1987, 109, 287-289.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A compound or a salt, solvate, or epoxide, thereof having a Formula I:

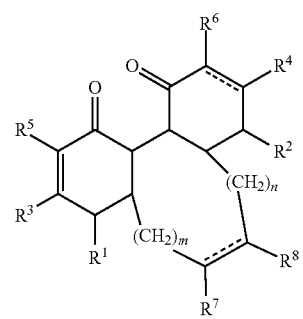

wherein:

––––– is a single or double bond, m and n are selected from 0 or 1; and each occurrence of R$^1$, R$^2$, R$^3$, R$^4$, R$^5$, R$^6$, R$^7$, and R$^8$ is independently selected from hydrogen, alkyl, hydroxyl, protected hydroxyl, alkoxy, alkoxy-alkyl, and dialkoxy-alkyl;

or R³ and R⁵ together form an epoxide and R⁴ and R⁶ together from an epoxide;
or R⁷ and R⁸ together from an epoxide.
2. The compound of claim 1, wherein the compound is an epoxide of Formula I having a Formula II or III:
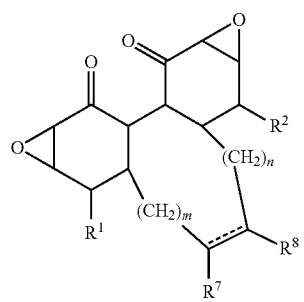
II
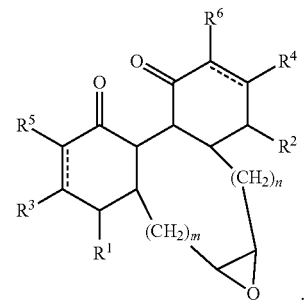
III
3. The compound of claim 1, having a formula selected from:
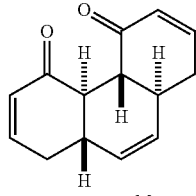 , 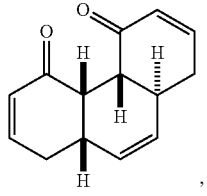 ,
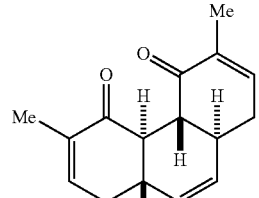 , 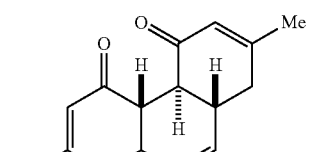 ,
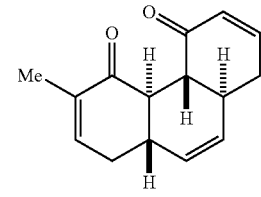 , 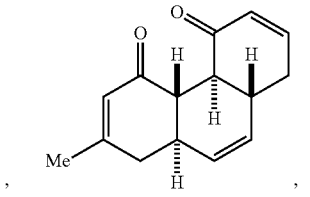 ,
-continued
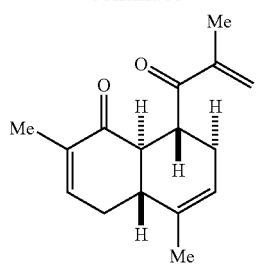
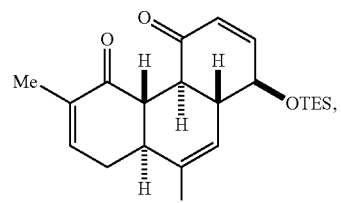
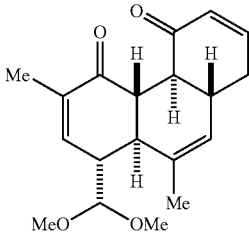
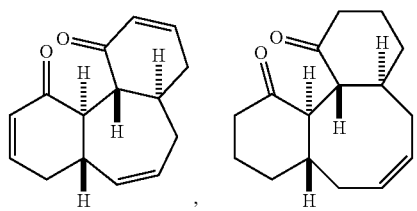 ,
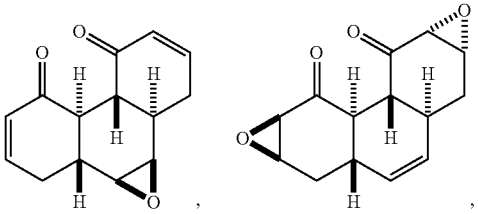 ,
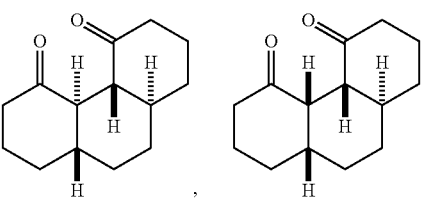 ,
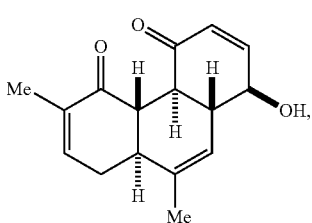

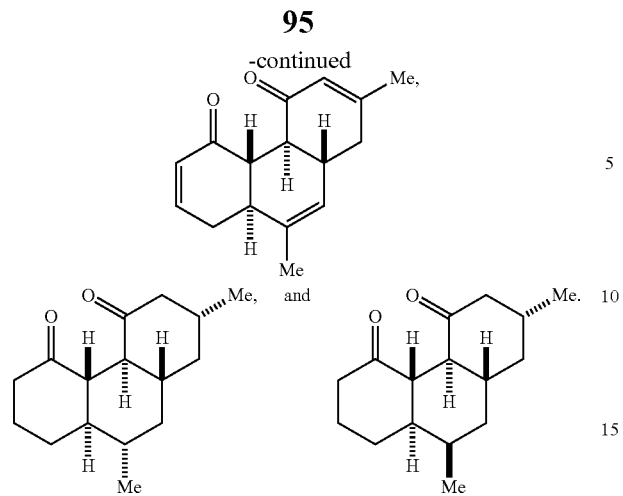

4. A pharmaceutical composition comprising the compound of claim 1 and a pharmaceutical carrier.

5. A compound or a salt, or a solvate thereof having a formula:

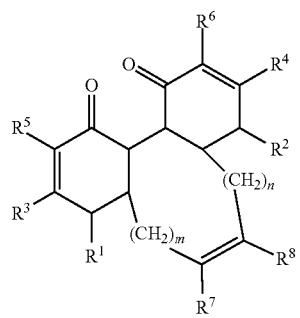

wherein:

m and n are selected from 0 or 1; and each occurrence of $R^1$, $R^2$, $R^3$, $R^4$, $R^5$, $R^6$, $R^7$, and $R^8$ is independently selected from hydrogen, alkyl, hydroxyl, protected hydroxyl, alkoxy, alkoxy-alkyl, and dialkoxy-alkyl.

6. The compound of claim 5, having a formula selected from:

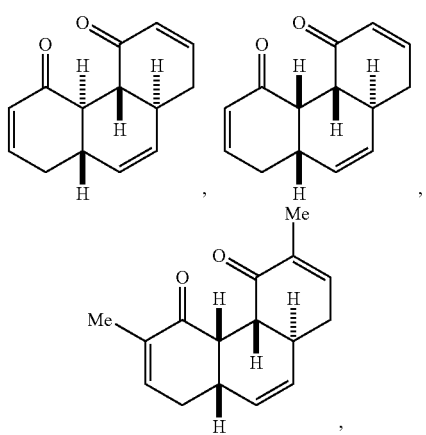

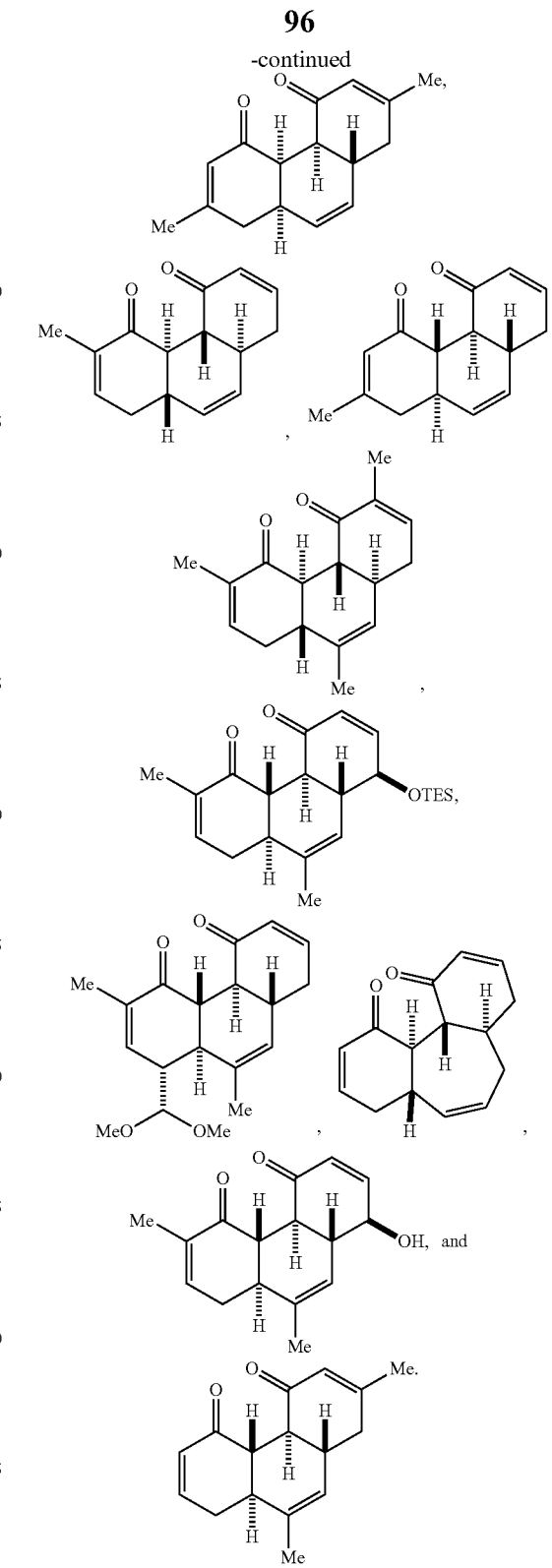

7. A pharmaceutical composition comprising the compound of claim 5 and a pharmaceutical carrier.

8. A compound or a salt, solvate, or an epoxide thereof having a formula:

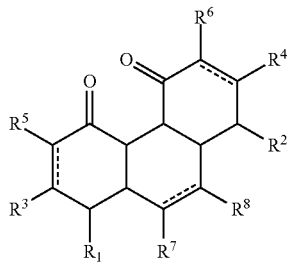

wherein:

==== is a single or double bond,
each occurrence of $R^1$, $R^2$, $R^3$, $R^4$, $R^5$, $R^6$, $R^7$, and $R^8$ is independently selected from hydrogen, alkyl, hydroxyl, protected hydroxyl, alkoxy, alkoxy-alkyl, and dialkoxy-alkyl;
or $R^3$ and $R^5$ together form an epoxide; or and $R^4$ and $R^6$ together from an epoxide;
or $R^7$ and $R^8$ together from an epoxide.

9. The compound of claim 8, wherein the compound is an epoxide of:

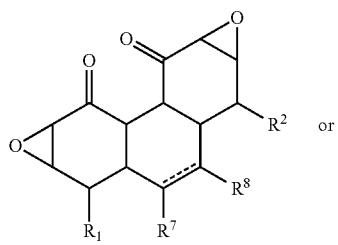

or

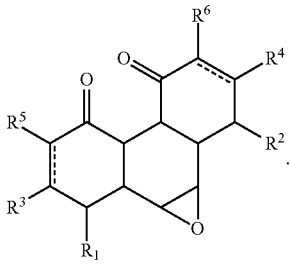

.

10. The compound of claim 8, having a formula selected from:

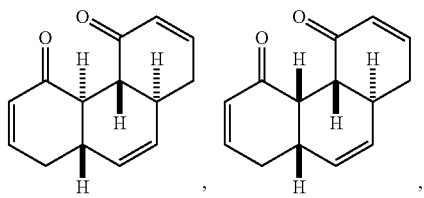

,

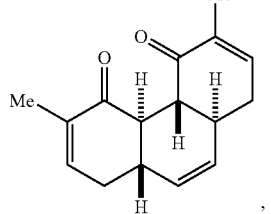

,

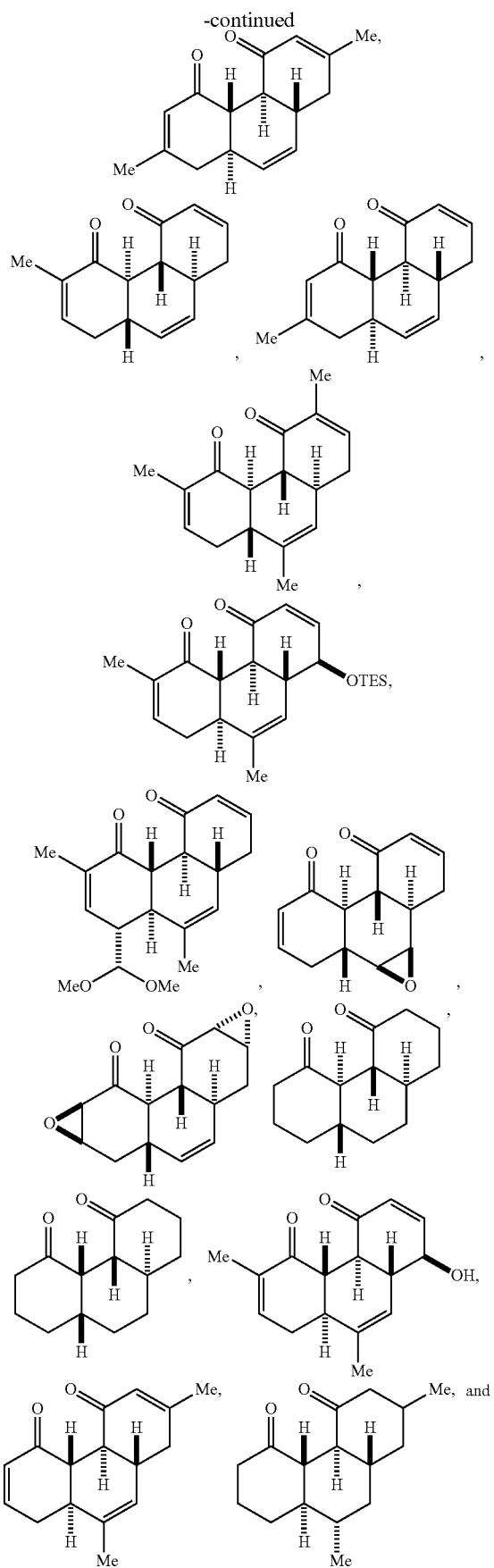

-continued
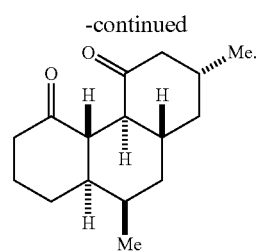
11. A pharmaceutical composition comprising the compound of claim 8 and a pharmaceutical carrier.
12. A compound having a formula:
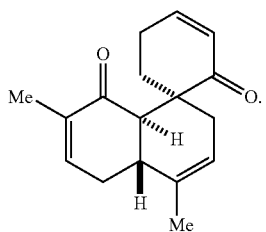
13. A compound having a formula:
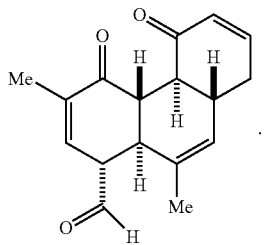
14. A compound having a formula:
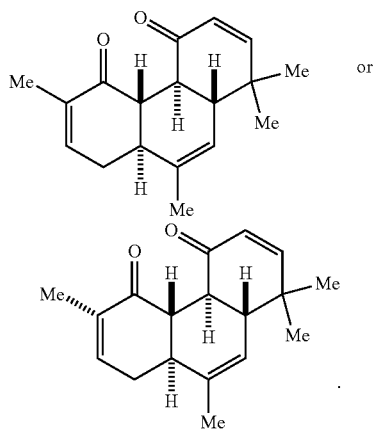
15. A compound having a formula:
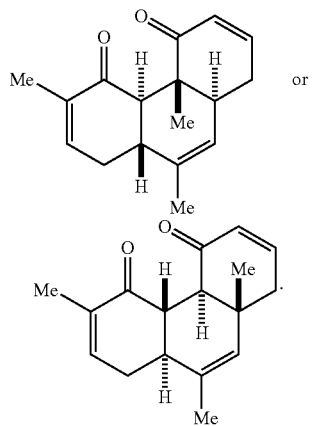
* * * * *